United States Patent
Greenhalgh et al.

(10) Patent No.: US 9,463,035 B1
(45) Date of Patent: Oct. 11, 2016

(54) MECHANICAL THROMBECTOMY APPARATUSES AND METHODS

(71) Applicant: GW Medical LLC, Pleasanton, CA (US)

(72) Inventors: E. Skott Greenhalgh, Lower Gwynedd, PA (US); Michael P. Wallace, Pleasanton, CA (US)

(73) Assignee: GW Medical LLC, Pleasanton, CA (US)

( * ) Notice: Subject to any disclaimer, the term of this patent is extended or adjusted under 35 U.S.C. 154(b) by 0 days.

(21) Appl. No.: 15/043,996

(22) Filed: Feb. 15, 2016

Related U.S. Application Data

(60) Provisional application No. 62/284,300, filed on Sep. 28, 2015, provisional application No. 62/284,752, filed on Oct. 8, 2015, provisional application No. 62/245,560, filed on Oct. 23, 2015.

(51) Int. Cl.
   *A61B 17/22* (2006.01)
   *A61B 17/00* (2006.01)
   *A61B 17/221* (2006.01)

(52) U.S. Cl.
   CPC ......... *A61B 17/22* (2013.01); *A61B 17/00234* (2013.01); *A61B 17/221* (2013.01); *A61B 2017/00292* (2013.01); *A61B 2017/00358* (2013.01); *A61B 2017/00778* (2013.01); *A61B 2017/22038* (2013.01); *A61B 2017/22079* (2013.01)

(58) Field of Classification Search
   CPC ............ A61B 17/22; A61B 17/22031; A61B 17/221; A61B 2017/22035; A61B 2017/22038; A61B 2017/22072; A61B 2017/22079; A61B 2017/2215
   See application file for complete search history.

(56) References Cited

U.S. PATENT DOCUMENTS

| | | | | |
|---|---|---|---|---|
| 4,243,040 | A * | 1/1981 | Beecher | A61B 17/22032 604/271 |
| 4,604,094 | A * | 8/1986 | Shook | A61M 25/0119 604/271 |
| 4,646,736 | A | 3/1987 | Auth | |
| 4,946,440 | A * | 8/1990 | Hall | A61B 18/08 600/569 |
| 5,364,345 | A * | 11/1994 | Lowery | A61B 1/00154 600/116 |
| 5,662,703 | A * | 9/1997 | Yurek | A61F 2/95 606/194 |
| 6,221,006 | B1 | 4/2001 | Dubrul et al. | |
| 6,238,412 | B1 | 5/2001 | Dubrul et al. | |
| 6,258,115 | B1 | 7/2001 | Dubrul | |
| 6,544,278 | B1 * | 4/2003 | Vrba | A61F 2/01 606/192 |
| 6,569,181 | B1 * | 5/2003 | Burns | A61F 2/95 606/108 |
| 6,620,179 | B2 * | 9/2003 | Boock | A61B 17/320758 606/159 |
| 6,635,068 | B1 | 10/2003 | Dubrul et al. | |
| 6,635,070 | B2 * | 10/2003 | Leeflang | A61B 17/22 606/200 |
| 6,942,682 | B2 * | 9/2005 | Vrba | A61F 2/01 606/192 |
| 7,621,870 | B2 * | 11/2009 | Berrada | A61F 2/013 600/200 |

(Continued)

OTHER PUBLICATIONS

Wikipedia; Embolectomy; retrieved from the internet: https://en.wikipedia.org/wiki/Embolectomy; 4 pgs.; retrieved/printed: Mar. 24, 2016.

(Continued)

*Primary Examiner* — Ryan J Severson
(74) *Attorney, Agent, or Firm* — Shay Glenn LLP

(57) ABSTRACT

Methods and apparatuses for mechanically removing objects from a body. In particular, described herein are thrombectomy methods and mechanical thrombectomy apparatuses for removal of blood clots from within a lumen of a blood vessel.

27 Claims, 34 Drawing Sheets

(56) References Cited

U.S. PATENT DOCUMENTS

| | | | | |
|---|---|---|---|---|
| 7,780,696 | B2* | 8/2010 | Daniel | A61B 17/221 606/200 |
| 8,057,496 | B2* | 11/2011 | Fischer, Jr. | A61B 17/221 604/508 |
| 8,070,769 | B2* | 12/2011 | Broome | A61F 2/013 606/200 |
| 8,092,486 | B2* | 1/2012 | Berrada | A61F 2/013 606/127 |
| 8,784,442 | B2* | 7/2014 | Jones | A61M 25/1002 606/127 |
| 8,795,305 | B2* | 8/2014 | Martin | A61F 2/06 606/159 |
| 8,956,384 | B2* | 2/2015 | Berrada | A61F 2/013 606/191 |
| 9,126,016 | B2 | 9/2015 | Fulton | |
| 9,155,552 | B2* | 10/2015 | Ulm, III | A61B 17/221 |
| 9,173,668 | B2* | 11/2015 | Ulm, III | A61B 17/221 |
| 9,186,487 | B2 | 11/2015 | Dubrul et al. | |
| 9,259,237 | B2* | 2/2016 | Quick | A61B 17/320725 |
| 2002/0032455 | A1* | 3/2002 | Boock | A61B 17/320758 606/159 |
| 2002/0173819 | A1* | 11/2002 | Leeflang | A61B 17/22 606/200 |
| 2003/0083693 | A1 | 5/2003 | Daniel et al. | |
| 2003/0176884 | A1* | 9/2003 | Berrada | A61F 2/013 606/200 |
| 2003/0208224 | A1* | 11/2003 | Broome | A61F 2/013 606/200 |
| 2004/0098033 | A1* | 5/2004 | Leeflang | A61B 17/22 606/200 |
| 2005/0119668 | A1* | 6/2005 | Teague | A61B 17/221 606/127 |
| 2005/0187570 | A1* | 8/2005 | Nguyen | A61B 17/221 606/159 |
| 2005/0283166 | A1* | 12/2005 | Greenhalgh | A61B 17/221 606/113 |
| 2005/0283186 | A1* | 12/2005 | Berrada | A61F 2/013 606/200 |
| 2006/0200221 | A1* | 9/2006 | Malewicz | A61F 2/966 623/1.11 |
| 2006/0293696 | A1 | 12/2006 | Fahey et al. | |
| 2007/0112374 | A1 | 5/2007 | Paul et al. | |
| 2007/0149996 | A1* | 6/2007 | Coughlin | A61F 2/013 606/200 |
| 2007/0213765 | A1* | 9/2007 | Adams | A61B 17/12136 606/200 |
| 2010/0030256 | A1* | 2/2010 | Dubrul | A61B 10/0266 606/200 |
| 2010/0042136 | A1* | 2/2010 | Berrada | A61F 2/013 606/200 |
| 2010/0087844 | A1* | 4/2010 | Fischer, Jr. | A61B 17/221 606/159 |
| 2010/0137846 | A1* | 6/2010 | Desai | A61B 17/221 606/2.5 |
| 2010/0249815 | A1* | 9/2010 | Jantzen | A61B 17/22031 606/159 |
| 2011/0288529 | A1* | 11/2011 | Fulton | A61M 25/04 604/510 |
| 2012/0083824 | A1* | 4/2012 | Berrada | A61F 2/013 606/200 |
| 2013/0046332 | A1* | 2/2013 | Jones | A61M 25/1002 606/200 |
| 2013/0317589 | A1* | 11/2013 | Martin | A61F 2/06 623/1.2 |
| 2014/0330286 | A1* | 11/2014 | Wallace | A61M 3/0283 606/127 |
| 2014/0336691 | A1* | 11/2014 | Jones | A61B 17/22032 606/194 |
| 2014/0364896 | A1* | 12/2014 | Consigny | A61B 17/3207 606/200 |
| 2014/0371779 | A1* | 12/2014 | Vale | A61B 17/12109 606/200 |
| 2015/0005781 | A1 | 1/2015 | Lund-Clausen et al. | |
| 2015/0018859 | A1* | 1/2015 | Quick | A61B 17/320725 606/159 |
| 2015/0018860 | A1* | 1/2015 | Quick | A61B 17/320725 606/159 |
| 2015/0164523 | A1* | 6/2015 | Brady | A61B 17/12109 606/200 |
| 2015/0190155 | A1* | 7/2015 | Ulm, III | A61B 17/221 600/424 |
| 2015/0190156 | A1* | 7/2015 | Ulm, III | A61B 17/221 606/200 |
| 2015/0196380 | A1* | 7/2015 | Berrada | A61F 2/013 606/200 |
| 2016/0022293 | A1* | 1/2016 | Dubrul | A61B 17/221 606/194 |
| 2016/0106448 | A1* | 4/2016 | Brady | A61B 17/12109 606/159 |
| 2016/0106449 | A1* | 4/2016 | Brady | A61B 17/12109 606/159 |
| 2016/0113663 | A1* | 4/2016 | Brady | A61B 17/12109 606/127 |
| 2016/0113664 | A1* | 4/2016 | Brady | A61B 17/12109 606/127 |
| 2016/0113665 | A1* | 4/2016 | Brady | A61B 17/12109 606/127 |

OTHER PUBLICATIONS

O'Sullivan; Thrombolysis versus thrombectomy in acute deep vein thrombosis; Interventional Cardiology; 3(5); pp. 589-596; Oct. 2011.

Capture Vascular Systems; (company website); retrieved from the internet: http://www.capturevascular.com; 3 pgs.; retrieved/printed: Mar. 24, 2016.

Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.

Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.

Penumbra, Inc.; Indigo® System (product information); retrieved from the internet: http://www.penumbrainc.com/peripheral/percutaneous-thromboembolectomy/indigo-system; 2 pgs.; retrieved/printed: Mar. 24, 2016.

Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.

Covidien; Solitaire(TM) AB Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.

\* cited by examiner

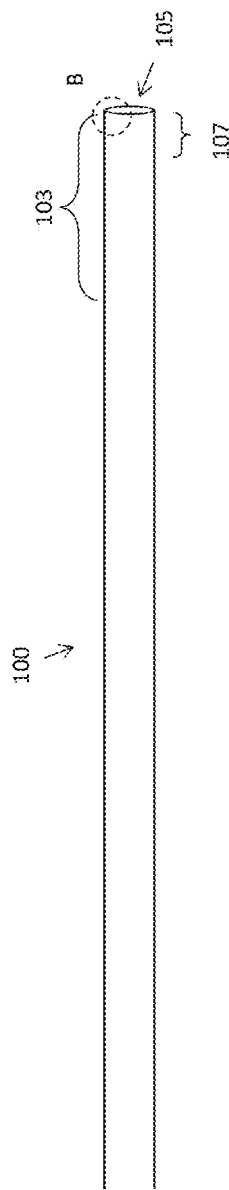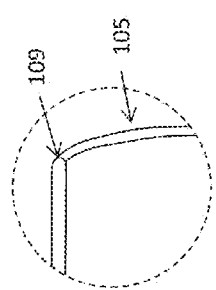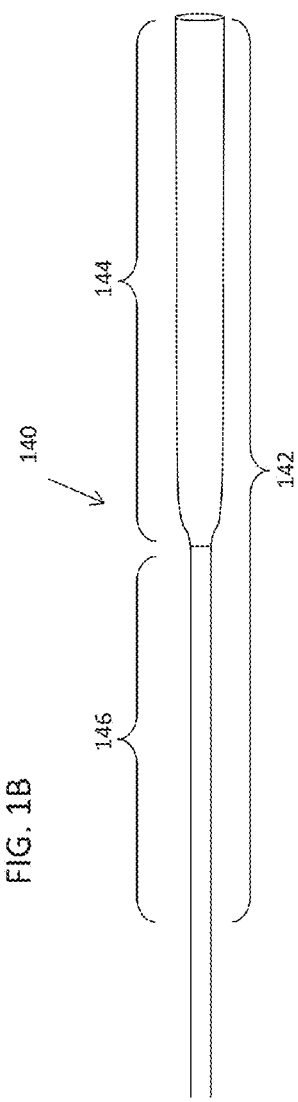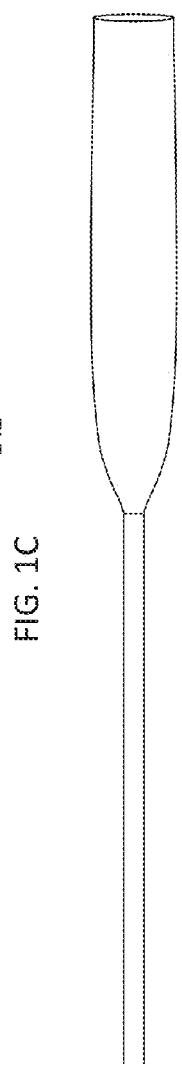
FIG. 1A
FIG. 1B
FIG. 1C
FIG. 1D

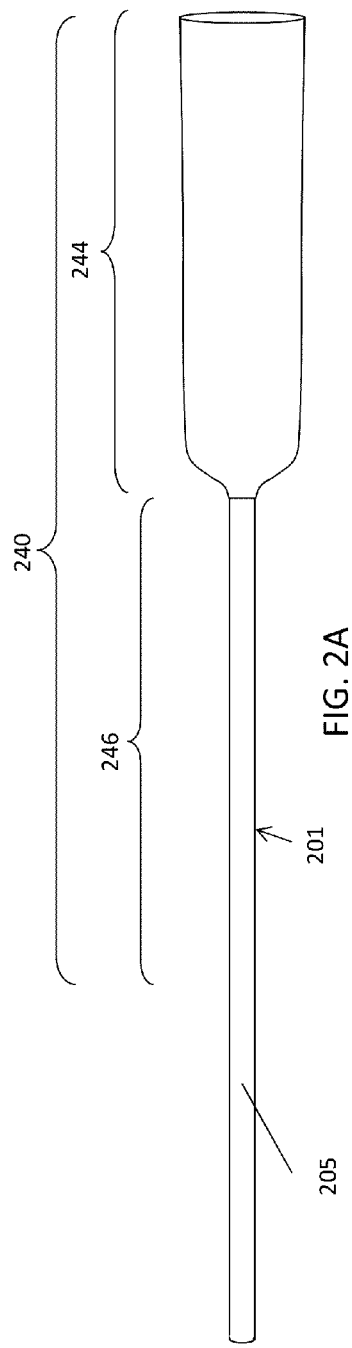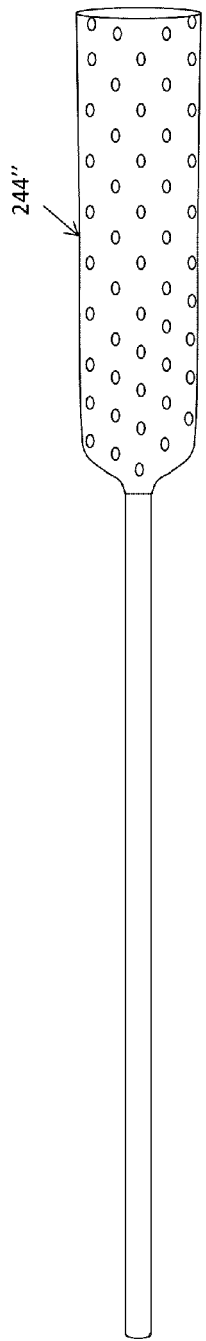

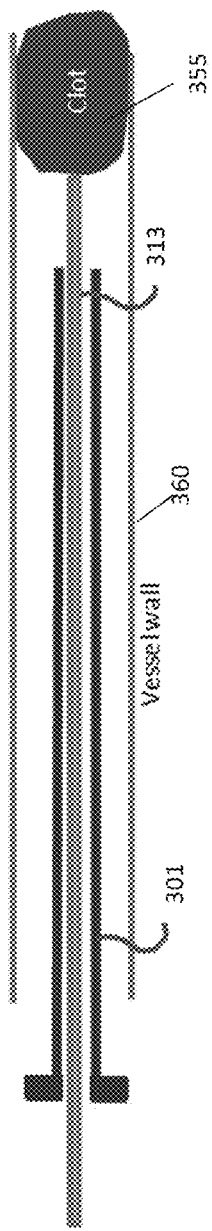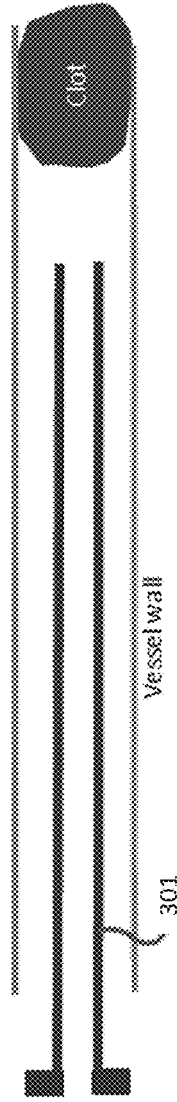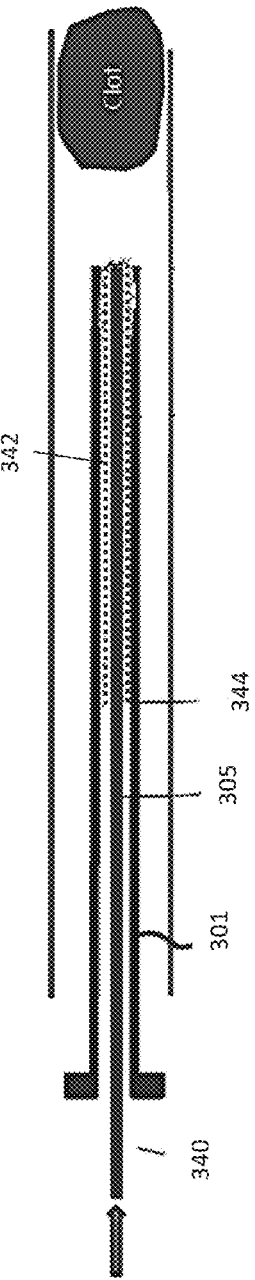
FIG. 3A
FIG. 3B
FIG. 3C

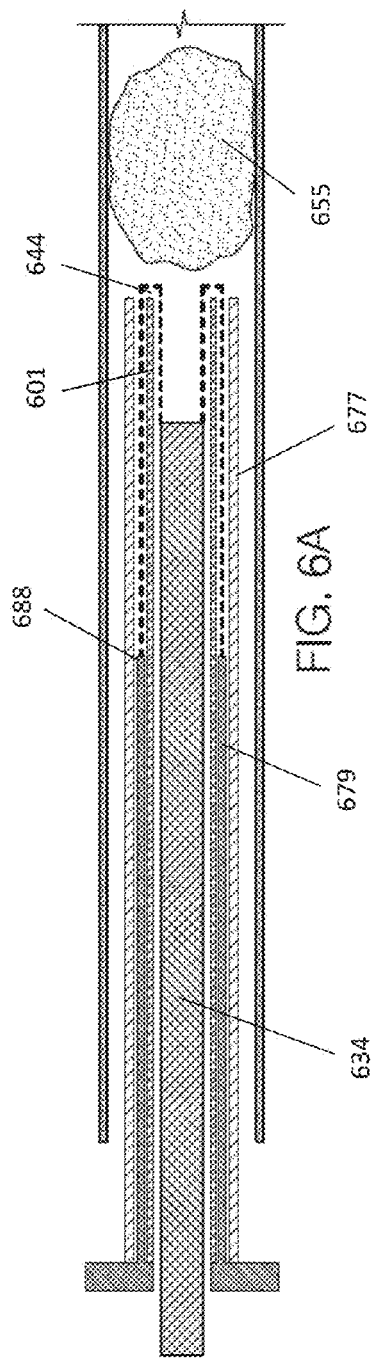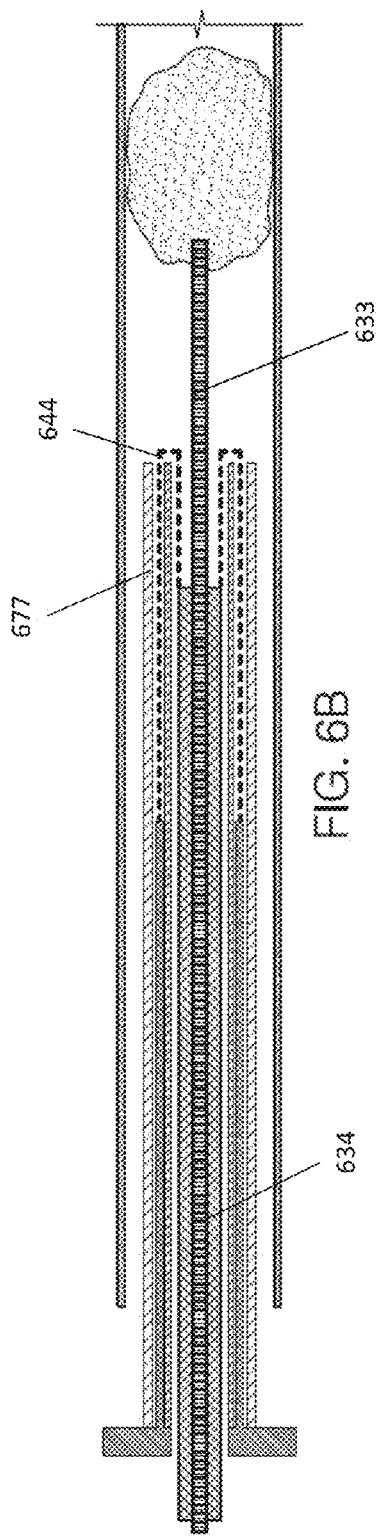

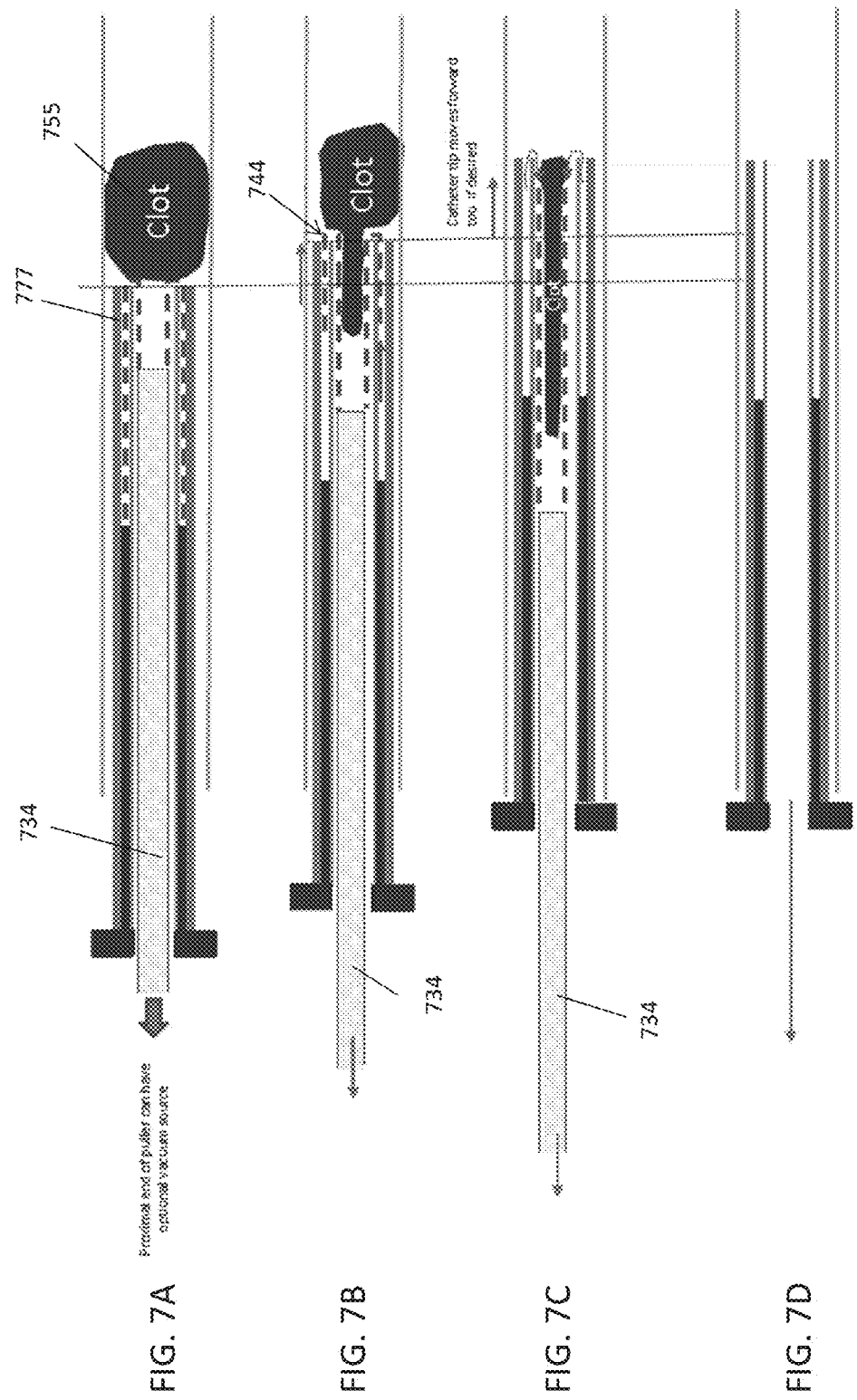

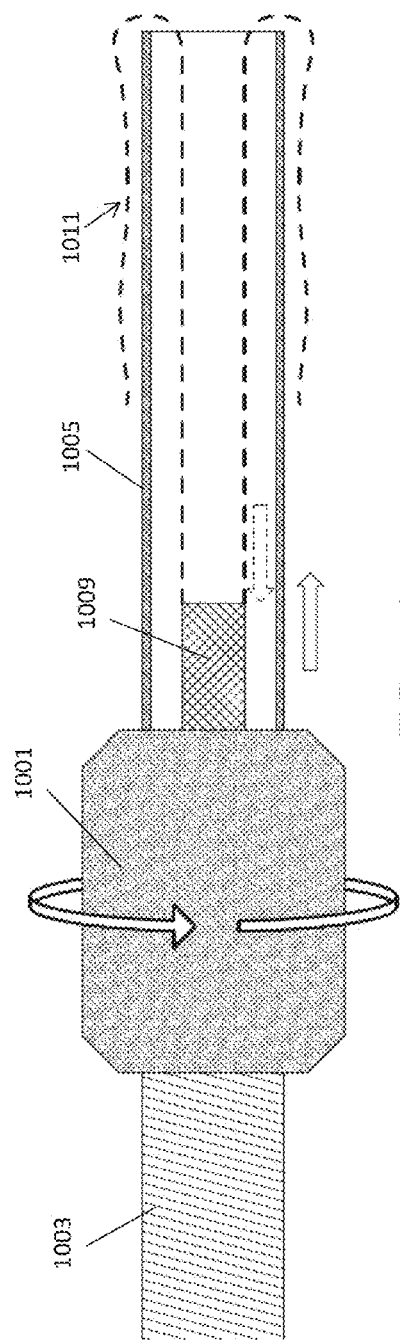
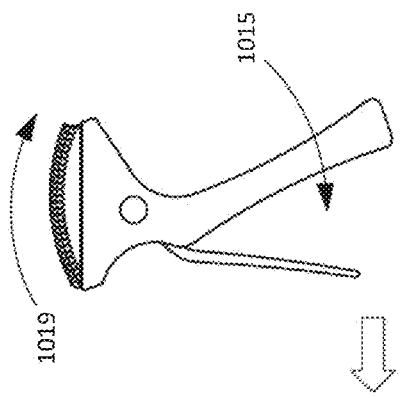
FIG. 10A
FIG. 10B

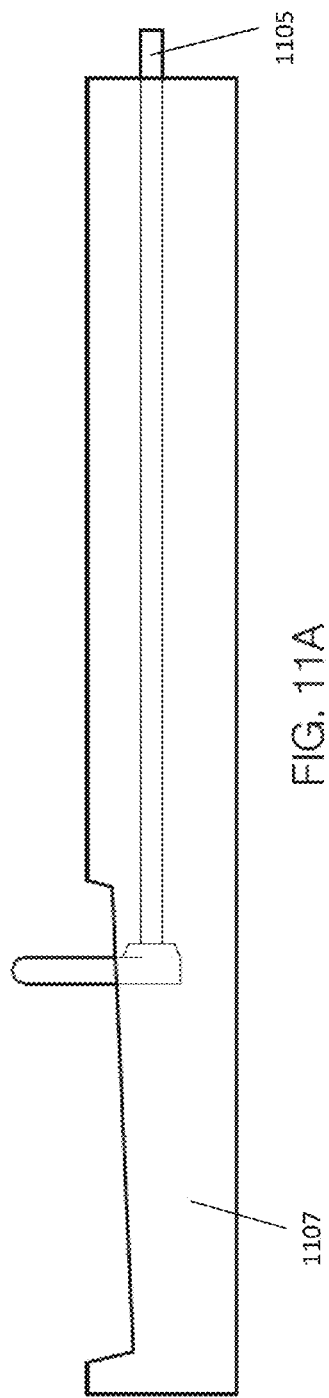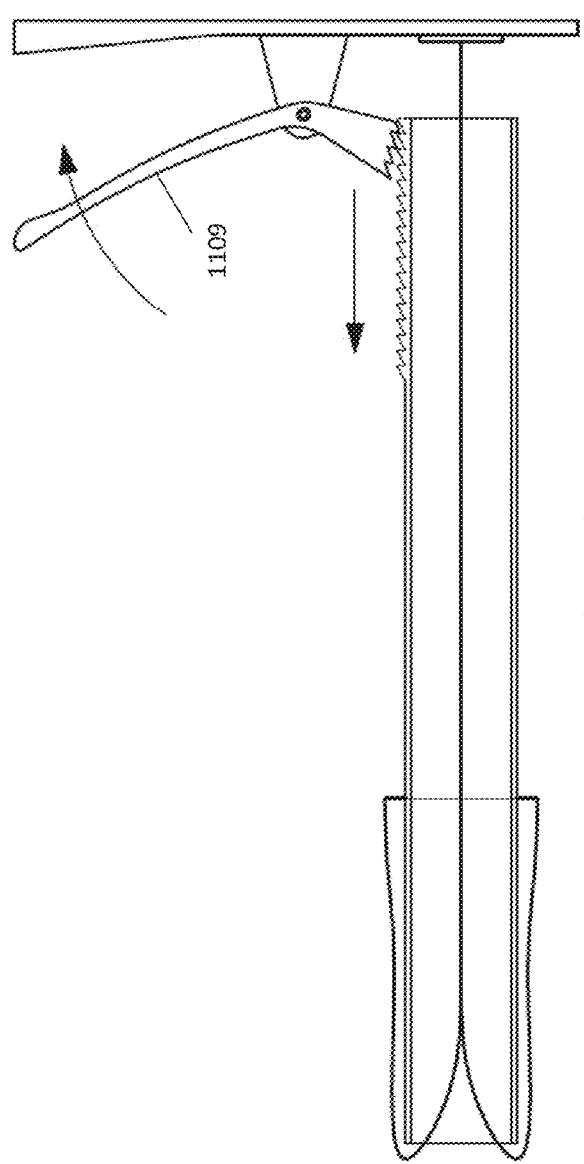
FIG. 11A
FIG. 11B

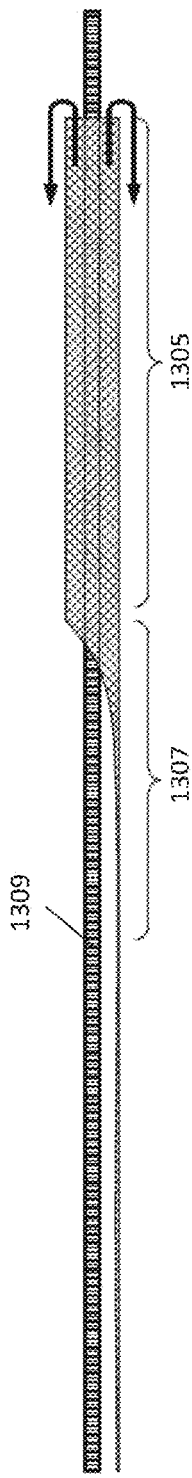
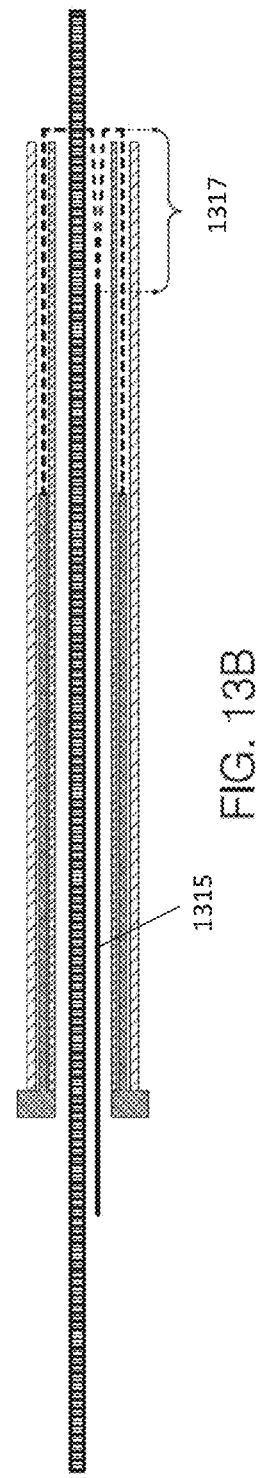
FIG. 13A
FIG. 13B

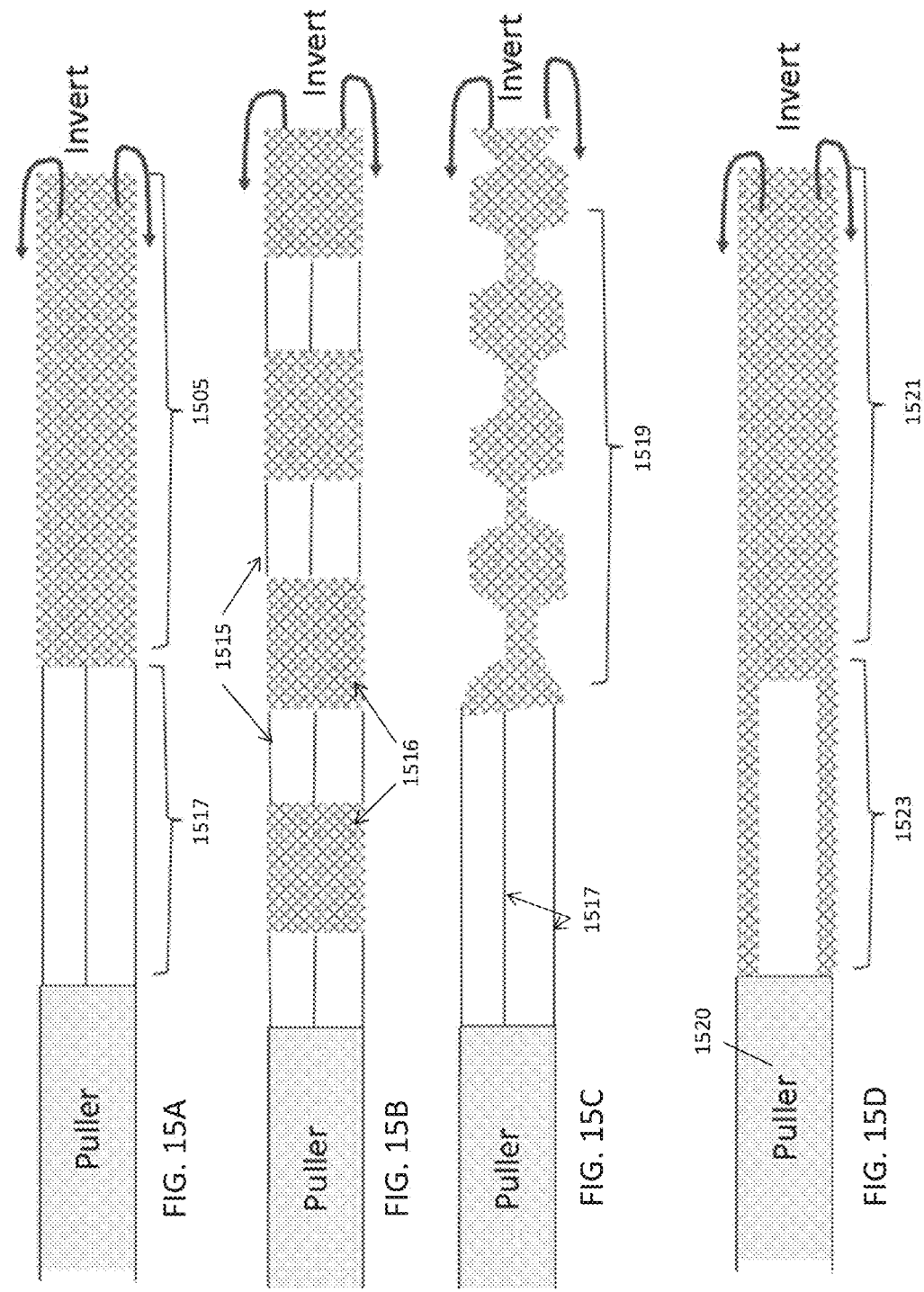

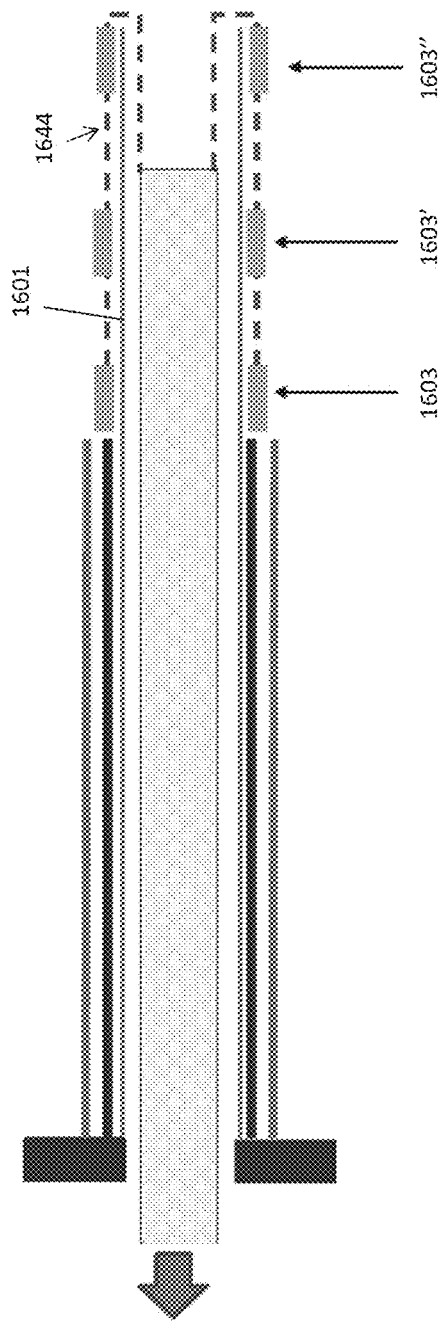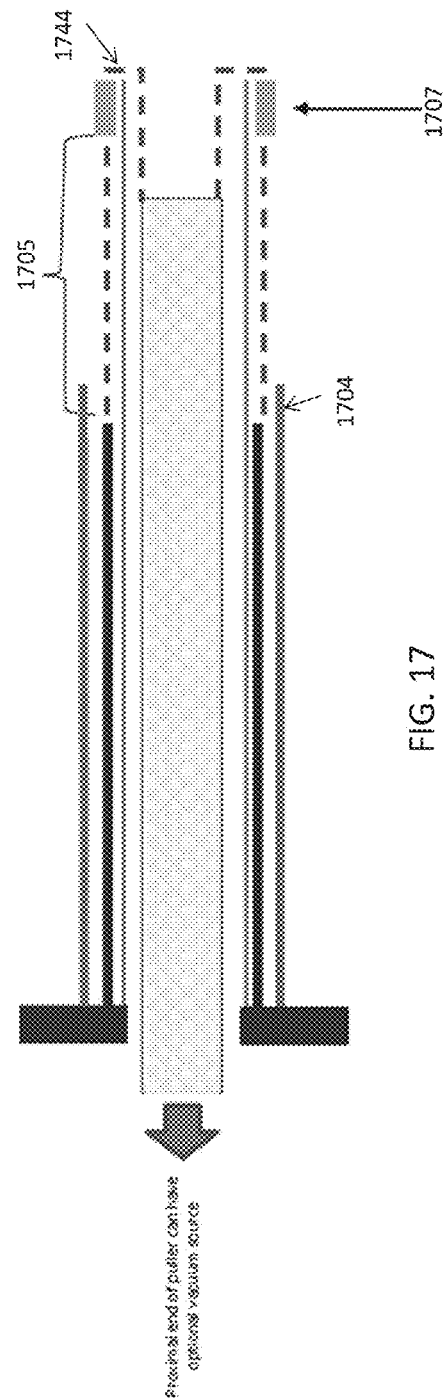

Example shape 1 (side profile); loaded either direction onto catheter & inverted Example shape 2 (side profile); loaded either direction onto catheter & inverted

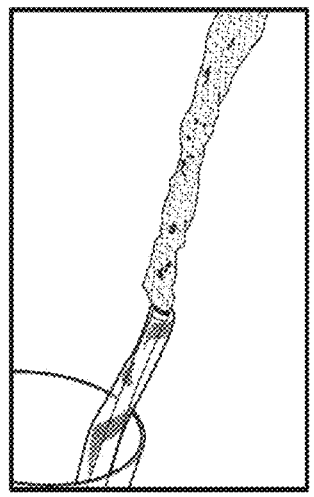
FIG.23A
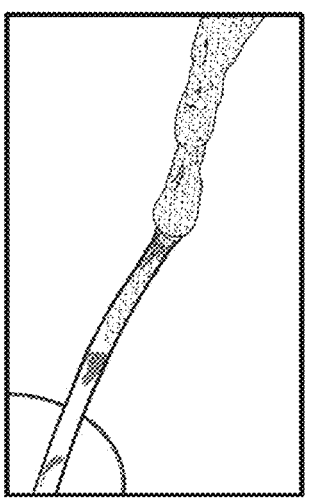
FIG.23C
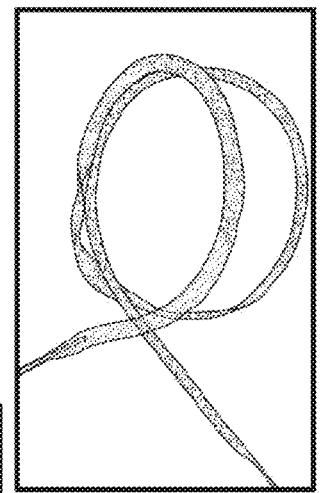
FIG.23B
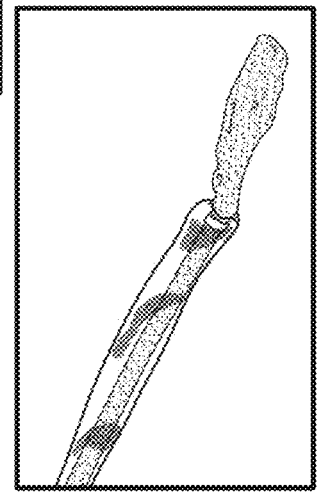
FIG.23D
FIG.23E

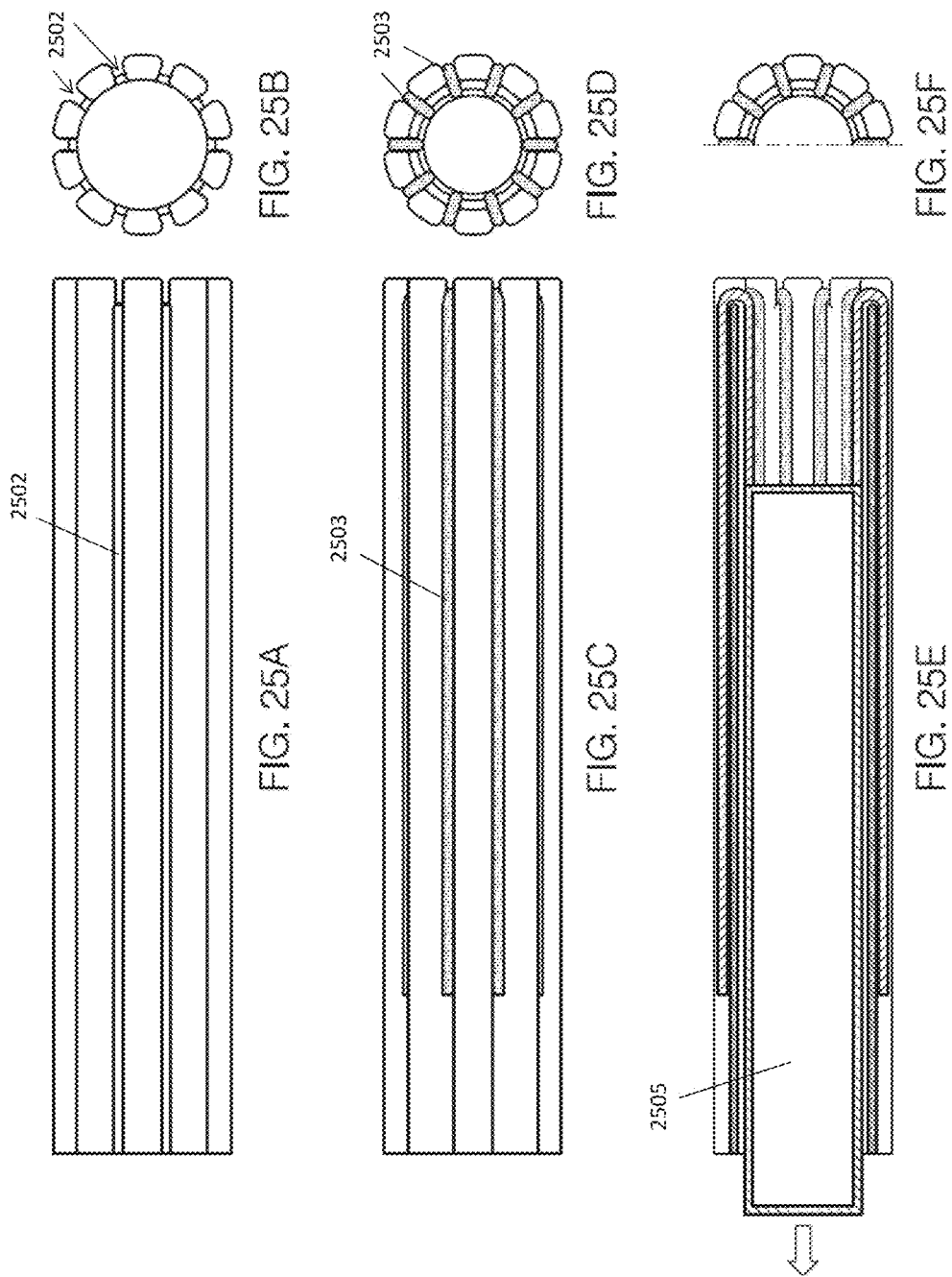

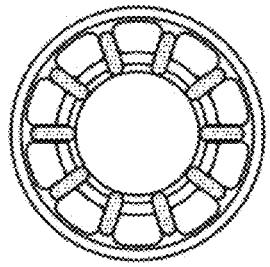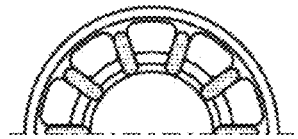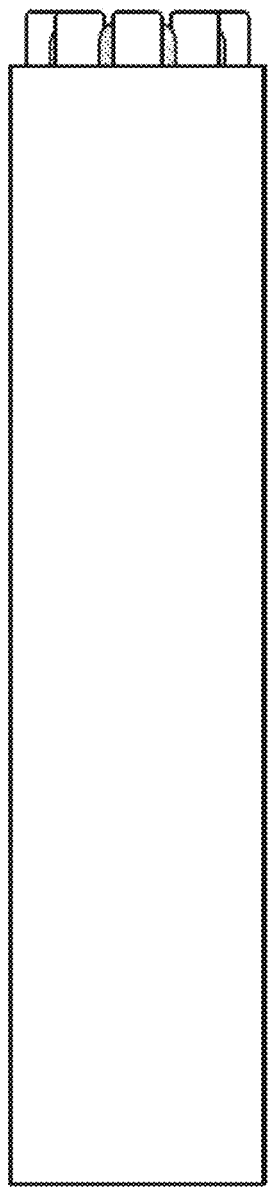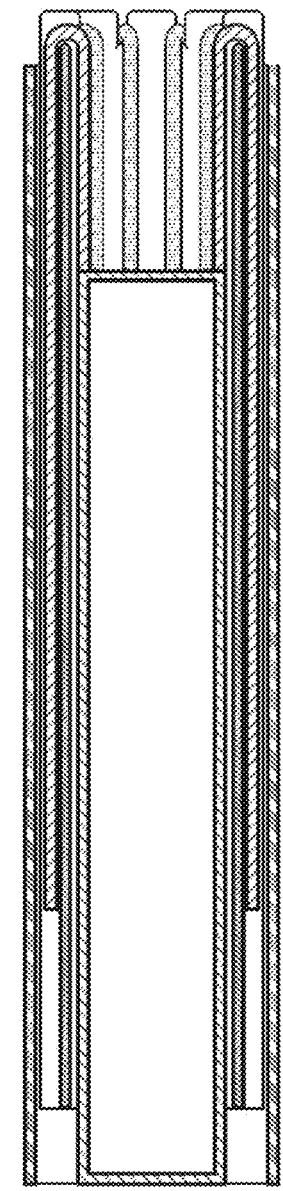

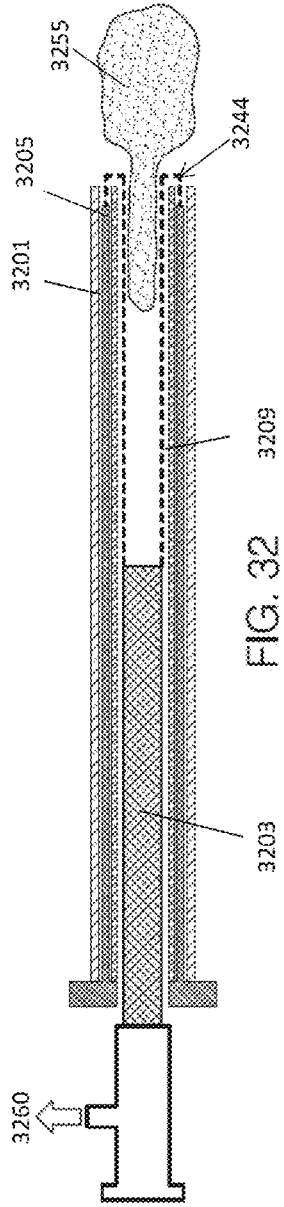
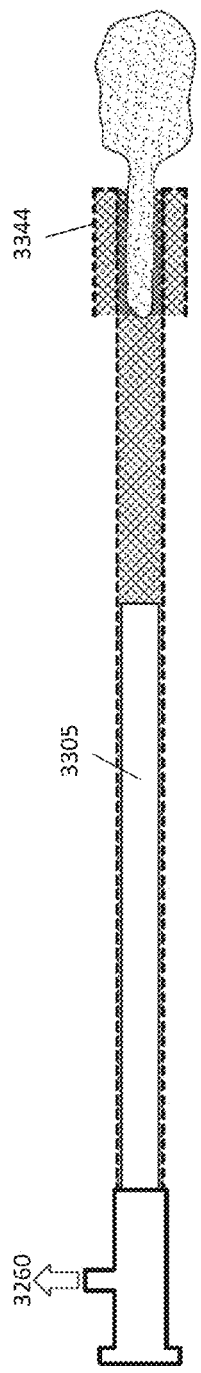
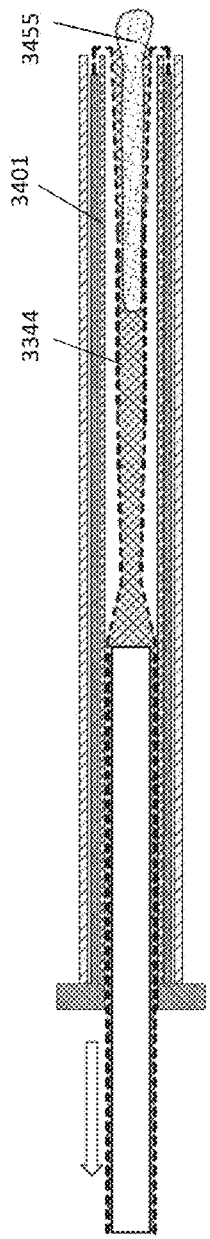
FIG. 32
FIG. 33
FIG. 34

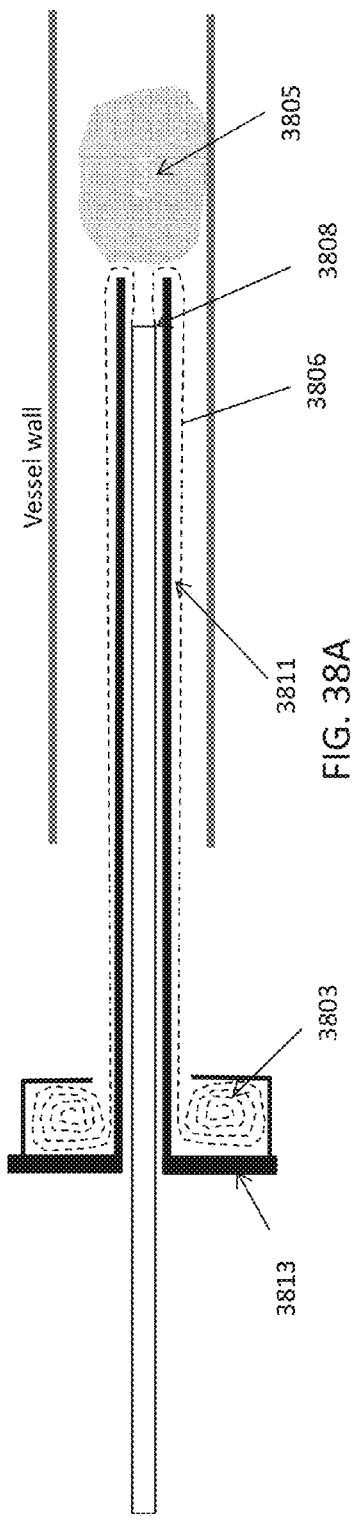
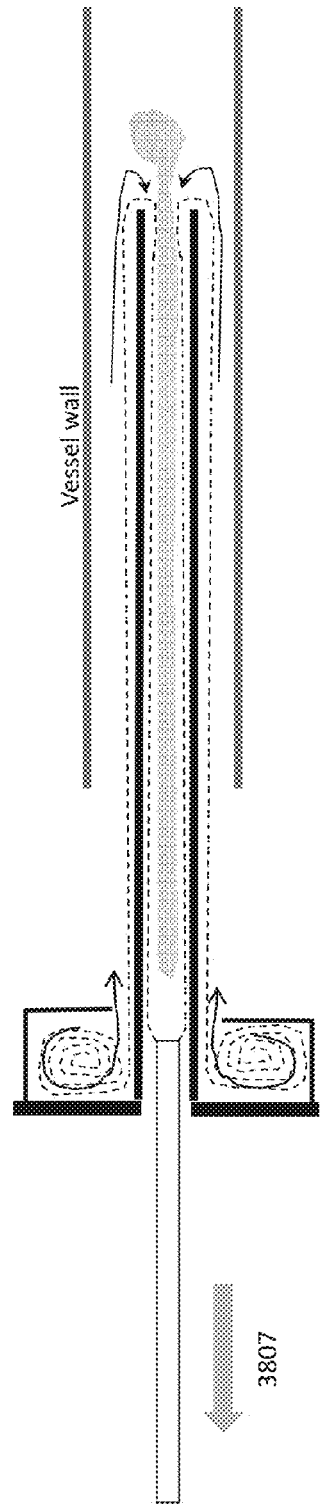

MECHANICAL THROMBECTOMY APPARATUSES AND METHODS

CROSS REFERENCE TO RELATED APPLICATIONS

This patent application claims priority to each of the following provisional patent applications, each of which is herein incorporated by reference in its entirety: U.S. Provisional Patent Application No. 62/284,300, filed Sep. 28, 2015; U.S. Provisional Patent Application No. 62/284,752, filed Oct. 8, 2015; and U.S. Provisional Patent Application No. 62/245,560, filed Oct. 23, 2015.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical removal of objects from within a body. In particular, described herein are mechanical thrombectomy apparatuses and methods.

BACKGROUND

It is often desirable to remove tissue from the body in a minimally invasive manner as possible, so as not to damage other tissues. For example, removal of tissue (e.g., blood clots) from the vasculature may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Catheter directed thrombectomy and thrombolysis are commonly perceived to be less traumatic, less likely to decrease the morbidity and mortality associated with conventional surgical techniques. In recent years, direct administration of chemical lysing agents into the coronary arteries has shown to be of some benefit to patients who have thrombosed coronary arteries. In this procedure, a catheter is placed immediately in front of the blockage and a drip of streptokinase is positioned to be directed at the upstream side of the thrombus. Streptokinase is an enzyme which is able in time to dissolve the fibrin molecule. This procedure can take several hours and is not always successful in breaking up the thrombus. Furthermore, it can lead to downstream thrombus fragments (emboli) which can lead to blockage of small diameter branches. U.S. Pat. No. 4,646,736 discloses a thrombectomy device that permits rapid removal of an obstructive thrombus. However, the device is characterized by small catheter tip size and thus is unable to exert significant total force on clot masses. Also, a clot which is not in good position of purchase on a vessel wall in the "line of fire" of the rotating wire is not fibrinectomized. This is especially true of clots floating free in the blood stream, since it is virtually impossible to revolve within these clots in the absence of a constraint such as fingers.

Further disadvantages to this thrombectomy device include the difficulty of keeping the clot in the space above the wire during all degrees of rotation as the wire is moved sideways during rotation, which is sometimes necessary to sweep the arterial lumen. In fact, sweeping out an entire arterial lumen with a rotating wire is virtually impossible in all but the smallest, i.e., less than 1.5 mm diameter, arteries. An additional and serious possible disadvantage is that fragments of the clot may be embolized downstream.

Another approach for capturing emboli is described in U.S. patent application 2015/0005781. This application describes a catheter with a basket extending from the distal end. An actuator, such as a rod or cable, can be pulled proximally to retract the basket into the catheter. Unfortunately, the basket occludes the inside of the lumen, preventing the concurrent use with a positioning and/or supporting guidewire, and the basket must be held in or near the distal end of the catheter. Depending on the stiffness of the material (e.g., clot) being removed, retrieval of the basket often collapses the distal end of the catheter, preventing its use, and the basket can be difficult to pull into the catheter, particularly when holding a clot. This may result in sheering the clot. Finally the basket must be preloaded into the distal end of the catheter prior to insertion into the vessel, and preloading may be both difficult and time consuming, and may risk disrupting the device prior to deployment.

Thus, there is a definite need for a thrombectomy device, and particularly a mechanical thrombectomy device that can be more effective in removing tissue such as clots from within a body. Described herein are apparatuses (devices, systems and kit) and methods of using them, that may address the needs and problems discussed above.

SUMMARY OF THE DISCLOSURE

In general, described herein are medical apparatuses, including medical devices and systems including these medical devices, and methods of operating these medical devices, for collecting objects, including but not limited to blood clots (thrombi), tissue (biopsies, small tumors, polyps, calcifications, kidney stones, etc.). The apparatuses described herein typically include an elongate catheter having a lumen and a distal end and with a distal end opening into the lumen. The catheter may be low-profile neurovascular catheters (e.g., microcatheters, insertion catheters, etc.) having any appropriate diameter (e.g., <1 Fr, 1Fr-6Fr, 1Fr-9 Fr, etc.). A flexible tractor assembly or portion (e.g., which may be referred to herein as a flexible tractor tube or simply a flexible tube) is typically positioned and longitudinally slideable within the catheter, and arranged so that the distal end region ("distal tractor region") doubles back over the distal end of the catheter. The flexible tube ("tractor tube") is generally elongate and hollow and configured to slide and invert over the distal end opening when a first end of the flexible tube is pulled proximally within the catheter. The distal end forming the distal tractor region may be tubular or not (e.g., it may be formed of strips of material, etc.). The combined catheter and flexible tractor assembly also forms a guidewire lumen through the catheter and the flexible tube that is configured to pass a guidewire.

In use, a guidewire may be configured to slide through the apparatus (and may form part of the apparatus) to allow positioning and in some variations support, typically without interfering with the operation of the tractor tube drawing an object such as a blood clot into the body of the catheter.

In addition to the catheter having a flexible tractor tube that is arranged within the catheter and inverted or doubled over the distal end of the catheter, the apparatuses described herein may include one or more features or elements that permit these devices to operate within a vasculature without collapsing, particularly at their distal ends, despite applying a pulling moment over the distal edge/opening of the preferably quite soft distal end. Further, these apparatuses may be adapted to minimize the force required to withdraw the distal tractor region into the catheter and invert over the distal end opening of the catheter, without damaging or weakening the distal tractor region, preventing a failure mode in which the flexible tractor tube within the apparatus breaks, binds up, jams or tangles on its self or with the catheter. For example, as will be described in greater detail below, any of these apparatuses may include a selectively lubricious region at or near the distal end of the catheter. The catheter end may be shaped to allow inverting of the flexible tractor region of the distal end of the tube. In addition, the end profile of the catheter (e.g., the distal-most 5 mm, 4 mm, 3 mm, 2 mm, 1 mm, etc.) may have an arrangement of stiffnesses (e.g., durometers) that prevent collapse/buckling of the catheter. Alternatively or additionally, the flexible tractor tube may be adapted for "sweeping" as much of the vessel around the catheter to collect objects from within the vessel while still allowing relatively low-force retraction into the catheter and inverting over the distal end of the catheter. The tractor portion of the flexible tube, which may refer to a distal portion of the tube within the catheter, may generally include a distal expandable (first) end region that is adjacent, either immediately adjacent or separated by a spacer region, to a second less-expandable (or non-expandable) end region. The second end region is proximal (when both the first end region and the second end regions are drawn into the catheter) to the first end region. The flexible tractor tube may extend all the way through the catheter to a proximal end and/or proximal handle, or it may end before the proximal end of the catheter and be connected to a puller. The puller may be another, possible less flexible tube, or a wire, rod, string, etc. The flexible tractor tube is generally configured to have a lumen through it (e.g., central lumen or radially offset lumen) through which a guidewire may be passed, passing through the apparatus, including the catheter and the flexible tractor tube. The flexible tractor tube may generally be operated (e.g., pulled proximally and in some variations pushed distally) while a guidewire is within this lumen.

The apparatus may be pre-loaded for deployment of the distal tractor region and capture of an object within a vessel, or in some variations it may be loaded in vivo, after or during positioning a guidewire and/or the catheter within a blood vessel. For example, in some variations, the apparatus may be adapted for use in vivo by holding the distal tractor region retracted into the catheter until the catheter is within the vessel, and preferably near the object to be removed. Once positioned, the distal tractor region of the flexible tube within the catheter may be distally extended from the catheter, expanded to form the capture shape that can be drawn and inverted over the distal end of the catheter either with or without advancing the catheter distally. Thus, the distal tractor portion may be safely and securely delivered to the necessary site within the lumen without risk to damage to the apparatus or the body.

For example, a method of performing a mechanical thrombectomy to remove a clot from a blood vessel may include: advancing a distal end of a catheter through the blood vessel towards the clot; exposing a distal tractor region of a tube that is within the catheter from the distal end of the catheter, wherein the distal tractor region comprises an expandable first end region and a less expandable second end region proximal to the expandable first end region; allowing the expandable first end region to expand within the blood vessel; positioning the distal end of the catheter so that a distal end region of the catheter is between the less expandable second end region and the expandable first end region of the distal tractor region while the expandable first end region is doubled over the less expandable second end region; and drawing the clot into the catheter by rolling the expandable first end region rolls over the distal end of the catheter so that the expandable first end region inverts as the expandable first end region is pulled into the catheter.

The step of advancing the distal end of the catheter through the blood vessel towards the clot may include advancing over a guidewire, as mentioned. The catheter may be slid distally over the guidewire or extended distally (or retracted proximally) with the guidewire. The inner (tractor) tube may be held within the catheter (e.g., near the distal end, a middle region, or near the proximal end) or in some variations it may be inserted after positioning the catheter within the vessel. The distal end of the catheter may be positioned at, near or adjacent the object to be removed (e.g., the clot), or it may be separated by a predetermined distance, e.g., to allow space for the apparatus to set up by extending the distal tractor region out of the distal end of the catheter and expand in preparation for withdrawing the object into the catheter.

Thus, once positioned, the apparatus may be deployed by exposing the distal tractor region and positioning the distal end of the catheter and in some variations the guidewire, to allow the object to be captured and drawn into the catheter.

The distal tractor region may be exposed by pulling the catheter proximally while either holding the flexible tube including the distal tractor region stationary (e.g., relative to the blood vessel) and/or by extending the flexible tube distally.

As mentioned, the flexible tube may include a distal tractor region that includes a first end region that is expandable. This end region is generally porous (e.g., formed of a mesh, knit, woven, or other material, including solid material having multiple openings therethrough) and adapted to grab the object (e.g. clot) to be removed. This first end region is generally expandable to between about 1.3× and about 10× the inner diameter of the catheter (e.g., between about 1.5 and about 7×, between about 1.5× and about 5×, between about 1.5 and about 4×, between about 1.5× and about 3×, etc.). This first distal end region forming the tractor portion is generally adjacent to the second end region that is less expandable (or not substantially expandable). The second region may extend proximally all the way down the catheter, or partially down the catheter. In general, the first end region of the tractor portion is exposed from out of the catheter and used to capture the clot or other object; the second end region may be exposed during positioning but may otherwise remain within the catheter during operation.

Thus, exposing a distal tractor region of a tube that is within the catheter from the distal end of the catheter may include extending or pushing the distal tractor region out of the distal end of the catheter. In some variations the distal tractor region is pre-formed so that the first expandable distal end region is doubled over the second distal end region; in other variations the first distal end region is in-line, distal to, the less expandable second distal end region. The catheter may then be moved distally so that a distal end region of the catheter (including the distal end) is extended in a gap radially between the expanded expandable first end region of the distal tractor region and the less-expandable second end region.

In any of the variations in which the distal tractor region is pushed out of the distal end of the catheter, e.g., during this initial in vivo set up phase, the flexible tube, and particularly the distal tractor region, may be configured or otherwise adapted to allow pushing out of catheter without binding up. Binding within the catheter of an expandable tube may occur if the expandable first end region in particular becomes caught on the inner walls of the catheter, preventing deployment. In some variations the expandable first end region is configured as a mesh tubular member having filaments (e.g. Nitinol, polymeric, etc.) having between about 24 to 144 stands, having a thickness of 0.0005 inches to 0.005 in diameter, wherein the mesh tubular member extends in a longitudinal axis, further wherein the mesh tubular member has a length that is greater than 5 cm, forms a braid angle between crossing strands in a direction of the longitudinal axis of about 35 degrees or less when being pulled and inverted around the distal end of the catheter and expands to a diameter of greater than 1.5 times an inner diameter of the catheter outside of the catheter when unconstrained. Within this configuration, the tubular member has been found to be pushable.

In other variations, when the expandable first distal end region is pushed or extended out of the distal end of the catheter, it may be configured (e.g., pre-shaped, shape-set, etc.) to invert over the distal end of the catheter and expand. The catheter may be moved distally, aiding in pushing this expandable first end region of the distal tractor region proximally relative to the outside of the catheter.

In any of these methods, the distal tractor region may include the expandable first end region and a less expandable second end region proximal to the expandable first end region, and the expandable first end region is permitted to expand within the blood vessel.

Thus, towards the end of the deployment phase, the distal end of the catheter is typically positioned so that the distal end region of the catheter is radially between the less expandable second end region and the expandable first end region of the distal tractor region while the expandable first end region is doubled over the less expandable second end region.

Thereafter, an object (e.g., clot) may be drawn into the catheter by rolling the expandable first end region over the distal end of the catheter so that the expandable first end region inverts as the expandable first end region is pulled into the catheter.

As mentioned, positioning may include distally advancing the distal end of the catheter so that the distal end region of the catheter is between the less expandable second end region and the expandable first end region of the distal tractor region.

A guidewire may be used with any of the methods described herein. For any of the methods described herein may include advancing a guidewire within the blood vessel to the clot, wherein advancing the distal end of the catheter comprises advancing the catheter over the guidewire through the blood vessel until the distal end of the catheter is proximate to the clot. The guidewire may be inserted into or through the clot, or it may be positioned just before the clot. The guidewire may be left in during clot removal, or it may be partially or completely withdrawn first. For example, any of these methods may include advancing a guidewire within the blood vessel to the clot, wherein advancing the distal end of the catheter comprises advancing the catheter over the guidewire through the blood vessel until the distal end of the catheter is proximate to the clot, further wherein drawing the clot into the catheter comprises advancing the catheter towards the clot over the guidewire while rolling the expandable first end region over the distal end of the catheter.

Drawing the clot into the catheter generally includes rolling the distal tractor region (e.g., the expandable first end region) over the distal end of the catheter. The apparatus may also be moved distally during actuation of the distal tractor region. For example, drawing the clot into the catheter may include withdrawing the tube proximally (to roll the distal tractor region over the distal end) and/or withdrawing the tube proximally while advancing the catheter distally.

In any of these methods, drawing the clot into the catheter may include withdrawing the tube proximally while advancing the catheter distally, wherein the tube is withdrawn at a different rate than the catheter is advanced. It may be beneficial in some configurations to advance the catheter distally more rapidly than the tube (distal tractor region) is drawn proximally. In some variations, the catheter may be advanced more slowly than the tube (distal tractor region) is withdrawn proximally. Alternatively in some variations, they are moved at the same rate. The rate of motion may be determined for the flexible tube by looking at the proximal motion (e.g., of the second end region) within the catheter.

In general the expandable first end region of the distal tractor region is expandable and may form a distal-facing mouth or lip that can engage with an object such as a clot. The mouth of lip of the expandable tractor region may form a tangent angle or roll angle (as described below in greater detail in reference to FIGS. 18 and 21D) with respect to the long axis of the catheter outer diameter (OD) in the range of 5-60 degrees and preferable at least 10 degrees (e.g., 10°-60°, 10°-50°, 10°-45°, etc.). As long as the roll angle is at least 10 degrees with the tube is retracted into the catheter, the tube should not bind or jam on the catheter tip. The mesh tube may be constructed by modifying is stiffness to ensure the roll angle in greater than 10 degrees. Alternatively or in combination to maintaining a minimum roll angle it may be desirable to maintain a physical space or gap between the tube material ID and the O.D of the catheter (as described in greater detail in FIG. 18, below) at the catheters most distal tip. The gap may need to be greater than, e.g., 0.1, mm 0.2 mm, 0.3 mm, 0.4 mm, 0.5 mm, 0.7 mm, 0.8 mm, 0.9 mm, 1.0 mm, etc. to ensure the tube rolls around the distal end of the catheter when the tube is retracted. The expanded material (e.g., a mesh, woven, braided, kitted, perforated, etc. material) may be allowed to expand within the blood vessel by itself. Thus the expandable first region may be self-expandable. The expandable first end region of the distal tractor region may be pre-biased to expand. In some variation a shape memory material (e.g., shape memory alloy) is used. In some variations a biasing element is included in or integral to the expandable first end region to expand so that the distal tractor region. The expandable first end region may expand to make contact with an intima of the blood vessel. In some variations the apparatus may be configured (e.g., sized, including sizing the expandable first end region) so that the distal-most end of the distal tractor region makes contact with the vessel lumen. Thus, any of the variations described herein may additionally or alternatively include a biasing element such as a loop, ring, scaffold, or the like to push the expandable distal end region open so that it can make contact with the vessel by applying an increased radial force to expand it open. In some variations this opening bias (loop, helix, ring, etc.) is located at or near the distal end of the expandable first end region of the distal tractor region.

Any of the variations described herein may include an expandable catheter tip. For example, in some variation the durometer of the catheter tip may be sufficiently soft to compress proximally when the distal tractor region is drawn proximally into the catheter; compressing the distal tip axially may expand it slightly (e.g., so that it may flare out) at the distal end.

As mentioned, exposing the distal tractor region of the tube that is within the catheter from the distal end of the catheter may comprise pushing the distal tractor region out of the distal end of the catheter. Alternatively or additionally, exposing the distal tractor region of the tube that is within the catheter out of the distal end of the catheter may comprise pulling the catheter proximally. For example, exposing the distal tractor region of the tube that is within the catheter from the distal end of the catheter may comprise pushing the distal tractor region out of the distal end of the catheter to expose the expandable first end region already inverted over the less expandable second end region.

In some variations, exposing the distal tractor region of the tube that is within the catheter from the distal end of the catheter comprises extending the expandable first end region out of the distal end of the catheter so that the expandable first end region inverts over the distal end of the catheter as the expandable first end region is extended.

The expandable first end region of the distal tractor region may be any appropriate length, and any portion of this length (all of it, 90%, 80%, 70%, 60%, 50%, 40%, etc.) may be exposed during this set-up period. For example, in some variations, exposing the distal tractor region of the tube may comprise exposing at least 5 mm of the expandable first end.

The expandable first end region may be, e.g. 5 mm or greater (e.g., 6, 7, 8, 9, 10, 11, 12, 13, 14, 15, 16, 17, 18, 19, 20, 25, 30, 35, 40, 45, 50, 55, 60, 70, 80, 90, 100, 110, 120, 130, 140, 150, 200, 300, 400, 500 mm, etc. between about 5 mm and 500 mm, between about any lower value of 5, 6, 7, 8, 9, 10, 11, 12, 13, 14, 15, 16, 17, 18, 19, 20, 25, 30, 35, 40, 45, 50, 55, 60, 70, 80, 90, 100, 110, 120, 130, 140, 150, 200 mm and any larger value of 10, 11, 12, 13, 14, 15, 16, 17, 18, 19, 20, 25, 30, 35, 40, 45, 50, 55, 60, 70, 80, 90, 100, 110, 120, 130, 140, 150, 200, 300, 400, 500 mm, where the lower value is always lower than the larger value). In any of these variations, when exposing the distal tractor region, either just the expandable first distal end region may be exposed out of the catheter (e.g., when pushing the expandable distal end region out distally and allowing it to invert over the distal end of the catheter) or both the expandable first distal end region and the less expandable second distal end region may all or partially exposed. For example, exposing at least 1 cm of the expandable first end region and at least 1 cm of the less expandable second end region. The expandable first end region may be inverted (doubled back) over the less expandable second end region.

As mentioned, the expandable first end region may comprise any appropriate material that is both expandable and able to grip the object (e.g., clot). For example the expandable first end region of the distal tractor region may comprise a mesh that is coupled adjacent to the less expandable second end region. For example the expandable first end region may be one or more of: a woven material, a mesh braided material, a knitted material, or a film material with multiple openings therethrough. The less expandable second end region may be made of the same material or it may be made of a different material. The less expandable second end region may have the same structure (e.g., woven, etc.) or it may have a different structure, including a less-expandable variation of the structure of the expandable first end region. For example the less expandable second end region may be a non-porous (e.g. non-woven, non-knitted, etc. or solid material) or less porous (e.g., tightly woven, small pore size knitted holes, tight braid). In some variation the less expandable second end region may include a transition region between the expandable first end region (e.g., having an intermediate expandability) and a non-expandable portion of the second end region. In general, the less expandable second end portion of the distal tractor region include non-expandable structures and materials.

A method of performing a mechanical thrombectomy to remove a clot from a blood vessel may include: advancing a distal end of a catheter through the blood vessel towards the clot; exposing a distal tractor region of a tube that is within the catheter from the distal end of the catheter, wherein the distal tractor region comprises an expandable first end region and a less expandable second end region proximal to the expandable first end region and configured so that the expandable first end region is inverted over the less expandable second end region; allowing the expandable first end region to expand within the blood vessel so that the distal end region of the catheter is between the less expandable second end region and the expandable first end region of the distal tractor region; and drawing the clot into the catheter by advancing the catheter distally and withdrawing the tube proximally within the catheter so that the expandable first end region rolls over the distal end of the catheter and inverts as the expandable first end region is pulled into the catheter.

As mentioned, the expandable first end region may be inverted over the less expandable second end region before exposing the distal tractor region. Alternatively, exposing the distal tractor region may include inverting the expandable distal end region over the less expandable second end region as the distal tractor region is exposed. In general, exposing the distal tractor region of the tube that is within the catheter from the distal end of the catheter may include pushing the distal tractor region out of the distal end of the catheter. Exposing the distal tractor region of the tube that is within the catheter out of the distal end of the catheter may include pulling the catheter proximally.

A method of performing a mechanical thrombectomy to remove a clot from a blood vessel may include: advancing a distal end of a catheter through the blood vessel towards the clot; exposing a distal tractor region of a tube that is within the catheter out of the distal end of the catheter, wherein the distal tractor region comprises an expandable first end region and a less expandable second end region, wherein exposing comprises extending the expandable first end region out of the distal end of the catheter so that the expandable first end region inverts over the distal end of the catheter as the expandable first end region is extended; allowing the expandable first end region to expand within the blood vessel as it is extended out of the distal end of the catheter so that a distal end region of the catheter is between the less expandable second end region and the expandable first end region; and drawing the clot into the catheter by withdrawing the tube proximally within the catheter so that the expandable distal end region rolls over the distal end of the catheter, collapses, and inverts as the expandable distal end region is pulled into the catheter. Exposing the distal tractor region of the tube that is within the catheter from the distal end of the catheter may include pushing the distal tractor region out of the distal end of the catheter. Alternatively or additionally, exposing the distal tractor region of the tube that is within the catheter out of the distal end of the catheter may include withdrawing the catheter proximally relative to the distal tractor region of the tube.

Also described herein are mechanical thrombectomy devices for removing a clot from a vessel, the device comprising: a catheter having a distal end and a distal end opening, wherein the catheter has an inner diameter and an outer diameter; a distal tractor region of a tube within the catheter, wherein the distal tractor region comprises an expandable distal end region and a less expandable distal end region proximal to the expandable distal end region, the distal tractor region configured so that the expandable distal end region is inverted over the less expandable distal end region; a guidewire lumen through the catheter and the tube, including the distal tractor region, wherein the guidewire lumen is configured to pass a guidewire; and a proximal handle coupled to the tube and configured to cause relative motion between the catheter and the tube such that the distal tractor region is released from within the inner diameter of the catheter so that the expandable distal end region may expand to a diameter that is greater than the outer diameter so that the catheter may be advanced between the expandable distal end region and the less expandable distal end region and the tube may be drawn proximally to pull the expandable distal end region over the distal end of the catheter so that the expandable distal end region rolls into the distal end of the catheter, inverts, collapses and is drawn into the catheter.

For example, a mechanical thrombectomy device for removing a clot from a vessel may include: a catheter having a distal end and a distal end opening, wherein the catheter has an inner diameter and an outer diameter; a tube having a distal tractor region within the catheter, wherein the distal tractor region comprises an expandable distal end region and a less expandable distal end region that is proximal to the expandable distal end region, further wherein the expandable distal end region is biased to invert over the less expandable distal end region as it is exposed from the distal end of the catheter; a guidewire lumen through the catheter and the tube, including the distal tractor region, wherein the guidewire lumen is configured to pass a guidewire; and a proximal handle coupled to the tube and configured to cause relative motion between the catheter and the tube such that the distal tractor region is released from within the inner diameter of the catheter so that the expandable distal end region may expand to a diameter that is greater than the outer diameter and the tube may be drawn proximally to pull the expandable distal end region over the distal end of the catheter so that the expandable distal end region rolls into the distal end of the catheter, inverts, collapses and is drawn into the catheter.

Also generally described herein are mechanical thrombectomy apparatuses. For example, described herein are mechanical thrombectomy apparatus for removing a clot from a vessel, including: a catheter having a distal end and a distal end opening; a flexible tube extending within the catheter and doubling back over the distal end of the catheter, wherein the flexible tube is configured to slide and invert over the distal end opening when a first end of the flexible tube is pulled proximally within the catheter; and a guidewire lumen through the catheter and the flexible tube that is configured to pass a guidewire.

A mechanical thrombectomy apparatus for removing a clot from a vessel may include: a catheter having a distal end and a distal end opening, wherein the distal end opening has a durometer that is greater than a durometer of a region immediately proximal to the distal end, further wherein the distal end opening has a rounded lip profile; a flexible tube extending within the catheter and doubling back over the distal end of the catheter, wherein the flexible tube is configured to invert over the distal end opening when a first end of the flexible tube is pulled proximally within the catheter; and a guidewire lumen through the catheter and the flexible tube configured to pass a guidewire. The catheter distal end durometer may be greater than 60A shore hardness or greater than 40D shore hardness.

A mechanical thrombectomy apparatus for removing a clot from a vessel that include: an inner catheter having a distal end and a distal end opening; a flexible tube extending though the catheter and doubling back over the distal end of the inner catheter, wherein the flexible tube is configured to invert over the distal end opening when a first end of the flexible tube is pulled proximally within the inner catheter; an outer catheter extending over the inner catheter and flexible tube; a lubricious region of the flexible tube extending between a distal end of the outer catheter and the distal end opening of the inner catheter, wherein the majority of the flexible tube is not lubricious; and a guidewire lumen through the catheter and the flexible tube configured to pass a guidewire.

A mechanical thrombectomy apparatus for removing a clot from a vessel may include: an inner catheter having a distal end and a distal end opening; a flexible tube extending though the catheter and doubling back over the distal end of the inner catheter, wherein the flexible tube is configured to invert over the distal end opening when a first end of the flexible tube is pulled proximally within the inner catheter; a releasable attachment between the flexible tube and an outer surface of the catheter, configured to release when the flexible tube is pulled with a predetermined force (e.g., that is greater than 0.01 N); and a guidewire lumen through the catheter and the flexible tube configured to pass a guidewire.

A mechanical thrombectomy apparatus for removing a clot from a vessel may include: a catheter having a distal end, a distal end opening and an inner diameter; a flexible tube extending through the catheter and doubling back over the distal end of the catheter, wherein the flexible tube is configured to invert over the distal end opening when a first end of the flexible tube is pulled proximally within the catheter, the flexible tube having a low Poisson's ratio, such that the flexible tube has a diameter of greater than half the inner diameter of the catheter when pulled proximally within the catheter with sufficient force to invert over the distal end opening; and a guidewire lumen through the catheter and the flexible tube configured to pass a guidewire. The flexible tubes having a low Poisson's ratio may be less than 0.5 or in the range of 0.05 to 0.5 or 0.1 to 0.3.

As already mentioned above the flexible tube typically includes the distal tractor region having an expandable first end region and a less- (or non-) expandable second end region proximally adjacent to the first end region. Thus, the flexible tube may comprise a mesh tube.

In general, the catheters forming part of the apparatuses described herein are highly flexible, as would be appropriate for the tortious paths taken, e.g. by neurovascular catheters. In some variations, the aggregate stiffness of the assembled apparatus (having the flexible tube wrapped over the distal end and ready for operation) is within a predetermined percentage (e.g., within 10%, within 12%, within 15%, within 16%, within 17%, within 18%, within 19%, within 20%, within 25%, within 30%, etc.) of the original stiffness of the catheter without the flexible tube. For example, the flexible tube extending through the catheter and doubling back over the distal end of the catheter may increases the stiffness of a distal 5 cm of the catheter by less than a predetermined percentage (e.g., 15%) of the stiffness of the distal 5 cm of the catheter without the flexible tube extending therethrough and doubling back over the distal end of the catheter.

In any of the variations described herein, the distal tractor region of the flexible tube is adapted to grab an object, e.g., clot. In particular, the flexible tube may be porous or have at least one porous section having a pore pattern having a longitudinal separation between pores of less than a predetermined distance (e.g., about 0.005 inches) in width. As used in this example "pores" includes windows, openings, gaps, etc. between strands of mesh (weave, etc.) as well as pores formed through a solid sheet of material. In general, for woven (and particularly braided) expandable first end region materials, smaller filaments may be better at grabbing, and therefore smaller pore sizes may be preferred. The optimal sizing may depend on the material, including filament size, pore percentage, size of the spacing of pores, pore diameters, etc. For example, in some variations it is beneficial to have a porosity of greater than >60% (greater than 70%, greater than 75%, greater than 80%, greater than 85%, etc., between 60-95, 65-95, 70-95%, etc.) and a fiber diameter (for woven materials) that is <0.005. The effective pore size of the flexible tubular member required to make sure the clot or foreign body is grabbed may range from 50 to 1000 micrometers (μm), or in the range of 100-200 μm, 100-300 μm, 100-500 μm or 500-1000 μm. The flexible tubular member may have a variety of pore sizes along its length.

In general, as used herein a woven material includes any material formed by weaving multiple strands of material in an interlacing pattern (e.g., interlacing strands, filaments, lengths of material, etc.). A mesh is one type of woven material. A woven material is typically more stretchable/expandable in certain directions (on the bias directions) depending on the elasticity of the material forming the weave. Woven materials are typically run in parallel or nearly parallel paths. A knitted material may be more flexible and generally refers to a single path or course that is meandering, forming loops that may be symmetrically arranged and interlocking. Woven material may be highly stretchable/flexible. Knitted constructs tend to be less stretchable but yet still highly flexible.

In any of the apparatuses described herein, and particularly the pre-loaded or pre-formed versions, the apparatus may include a releasable attachment between the flexible tube and an outer surface of the catheter, configured to release when the flexible tube is pulled with a force that is greater than a predetermined force threshold. For example, the releasable force threshold may be greater than about 0.001 N, greater than about 0.005 N, greater than about 0.01 N, greater than about 0.03 N, greater than about 0.05 N, greater than about 0.08 N, greater than about 0.1 N, greater than about 0.3 N, greater than about 0.5 N, etc.).

In any of the apparatuses described herein, the flexible tube may comprise a plurality of strips of flexible material, wherein the strips are arranged in parallel with the long axis of the flexible tube. Alternatively or additionally, in any of these variations, the distal end opening may comprise a plurality of notches or channels into which fibers or strips forming the flexible tube are drawn as the flexible tube inverts over the distal end opening.

In any of the apparatuses described herein, the flexible tube may comprise a polymeric tube having a plurality of holes therethrough. For example, the flexible tube may comprise a distal end, a proximal end and a body region there between, wherein the body region transitions from a more flexible distal end to a stiffer proximal end.

As mentioned above, in any of the variations described herein, the distal end of the catheter (e.g., the distal opening region) may be adapted to prevent collapsing when inverting the distal tractor region over the catheter opening but still be soft enough to provide appropriate use for neurovascular applications. For example, any of the apparatuses described herein may have a durometer at the distal end (e.g., at the distal end opening/rim) that is greater than a durometer of a region immediately proximal to the distal end. Any of these distal end openings may have a rounded lip profile. In general, though the durometer of the distal end region may decrease (becoming 'softer') the durometer of the very distal end (the opening) may be high. This, along with a rounded end shape, may reduce the force needed to invert the distal tractor region (e.g., the expandable first end region) as it is drawn into the catheter, while preventing collapse of the distal end region of the catheter.

Any of the apparatuses described herein may also include a handle adapted to draw the flexible tube proximally relative to the catheter. The handle may be attached or attachable to the catheter and/or the flexible tube and may include separate controls for actuating each independently or, more preferably, in a coordinated manner (or toggle between these two modes). For example, any of these apparatuses may include a drive handle coupled to a proximal end region of the catheter, wherein the drive handle comprises a control configured to coordinate advancing of the catheter distally while retracting the flexible tube proximally when actuated.

Any of these apparatuses may also include an outer catheter extending over the catheter and flexible tube. The outer catheter may extend over the catheter and the flexible tube and may keep an external portion of the distal tractor region (outside of the catheter) collapsed until it has been delivered. Any of these apparatuses may include a lubricious region of the flexible tube extending between a distal end of the outer catheter and the distal end opening, wherein the majority of the flexible tube is not lubricious. This lubricious region may reduce the initial force required to start actuating the apparatus.

In any of the apparatuses described herein, the flexible tube may be configured to invert over the distal end opening when a first end of the flexible tube is pulled proximally within the catheter and the flexible tube may have a low Poisson's ratio such that the flexible tube (which may be a mesh tube) may have a diameter of greater than half the inner diameter of the catheter when pulled proximally within the catheter with sufficient force to invert over the distal end opening.

Any of these apparatuses may include a puller (e.g., an elongate puller) within the catheter and coupled to a distal end of the flexible tube. The puller is typically configured to draw the flexible tube proximally, though in some variation it may also move it distally. For example, any of these apparatuses may also include an elongate puller within the catheter and coupled to a distal end of the flexible tube, wherein the elongate puller comprises a hypotube having an inner lumen that is continuous with the guidewire lumen though the flexible tube.

As mentioned, in some variations, the flexible tube comprises a soft outer mesh that is pushable. For example the distal tractor region (and particularly the expandable first end region) may be formed from 24 to 144 stands, having a thickness of 0.0020 inches or less in diameter, wherein the mesh tubular member extends in a longitudinal axis, further wherein the mesh tubular member has a length that is greater than 5 cm, forms a braid angle between crossing strands in a direction of the longitudinal axis of about 35 degrees or less when being pulled and inverted around the distal end of the catheter and expands to a diameter of greater than 1.5 times an inner diameter of the catheter outside of the catheter when unconstrained.

When the flexible tube is formed of strands (e.g., woven, braided, etc.) the strands may be formed of any of the following; monofilament polymer, multifilament polymer, NiTi filament, NiTi tube with radiopaque metallic center, Cobalt chromium alloy filament, Cobalt chromium alloy tube with radiopaque metallic center, Nylon, Polyester, Polyethylene terephthalate, and Polypropylene.

As mentioned, any of these apparatuses may be configured so that the flexible tube (e.g., expandable distal end region) are releasably held onto the catheter. For example any of these apparatuses may include a retaining ring around a distal end region of the flexible tube configured to releasably hold the flexible tube against the catheter.

In any of these variations, the flexible tube may be shape set to have different diameter when within the catheter after being pulled proximally into the catheter. In general, the flexible tube may include a plurality of woven or one (or more) knitted filaments. In some variations the entire (or majority of the) flexible tube is formed of a woven or knitted filament(s), and the proximal end of the flexible tube may form a tapered opening opposite from a filament or bundle of filaments forming a pull wire. Alternatively or additionally, the flexible tube may be formed from a sleeve of polymer having a thickness less than 0.020 inches, wherein the sleeve comprises a perforation pattern in which the perforations extend through the polymer. The perforation pattern may comprise perforations having a shaped consisting of one or more of: round holes, rectangular holes and zig-zag shapes.

Any of these apparatuses may include a pull wire coupled to one side of a proximal end of the flexible tube configured to be drawn proximally to pull the flexible tube within the catheter.

In general, the flexible tube may be any appropriate length. For example, the flexible tube may be between 3 to 200 cm (e.g., between 3 to 150 cm, 3 to 100 cm, 3 to 50 cm, etc.).

In any of the apparatuses described herein, the flexible tube of the apparatus may be configured so that the flexible tube may be retracted into the catheter by applying less than a predetermined amount of force (e.g., 500 grams of force, 450 grams of force, 400 grams of force, 350 grams of force, 300 grams of force, 250 grams of force, 200 grams of force, 150 grams of force, etc.) to a distal end of the flexible tube.

In any of these variations, the flexible tube may include a taper between the first end and a second end of the flexible tube. In some variations, the flexible tube may extend within the entire length of the catheter so that a proximal end of the flexible tube is configured to be pulled proximally away from the proximal end of the catheter to slide and invert the flexible tube over the distal end opening.

Any of the apparatuses described herein may also include a vacuum source. For example any of these apparatuses may include a guidewire vacuum pump coupled to a proximal end of the guidewire lumen and configured to apply vacuum therethrough. For example, any of these apparatuses may include an outer catheter vacuum pump coupled to a space between the catheter and the flexible tube and configured to apply a vacuum within a lumen of the catheter between an inner wall of the catheter and the flexible tube.

As mentioned, the apparatus may include a puller, wherein a distal end of the flexible tube is coupled to a distal end of the puller. An outer catheter may be arranged over the catheter adjacent to a proximal end of the flexible tube. Any of these apparatuses may also include a handle having a control configured to coordinate advancing of the outer catheter to push the proximal end of the flexible tube distally and pulling the puller proximally to drawn the proximal end of the flexible tube into the catheter. For example, an apparatus as described herein may include: a puller, wherein a distal end of the flexible tube is coupled to a distal end of the puller; an outer catheter slideably arranged over the catheter coupled to a proximal end of the flexible tube; and a handle having a control configured to coordinate advancing of the outer catheter distally to push the proximal end of the flexible tube distally while pulling of the puller proximally to drawn the proximal end of the flexible tube into the catheter or pulling the outer catheter proximally to pull the proximal end of the flexible tube proximally while pushing of the puller distally to push the proximal end of the flexible tube out of the catheter.

Also described herein are methods of mechanically removing a thrombectomy including: advancing a guidewire at least to the proximal end of a clot in a blood vessel; advancing a thrombectomy (e.g. clot removal) apparatus distally over the guidewire, wherein the thrombectomy apparatus comprises a catheter having a distal end and a distal end opening and a flexible tube extending along an outer diameter of the catheter and over the distal end of the catheter, so that the guidewire passes through a lumen of the catheter and the flexible tube; pulling the flexible tube proximally from off of the outer diameter of the catheter and into the catheter lumen so that the flexible tube slides and inverts over the distal end opening; and drawing a clot into the inverted flexible tube as the flexible tube is drawn into the catheter.

A method of mechanically removing a thrombectomy may include: advancing a guidewire adjacent a clot in a blood vessel; advancing a thrombectomy apparatus distally over the guidewire, wherein the thrombectomy apparatus comprises a catheter having a distal end and a distal end opening and a flexible tube extending along an outer diameter of the catheter and over the distal end of the catheter, so that the guidewire passes through a lumen of the catheter and the flexible tube; pulling the flexible tube proximally from off of the outer diameter of the catheter and into the catheter lumen over a rounded lip of the distal end opening of the catheter so that the flexible tube slides and inverts over the distal end opening, wherein the distal end opening has a durometer that is greater than a durometer of a region immediately proximal to the distal end; and drawing a clot into the inverted flexible tube as the flexible tube is drawn into the catheter.

A method of mechanically removing a thrombectomy may include: advancing a guidewire adjacent a clot in a blood vessel; advancing a thrombectomy apparatus distally over the guidewire, wherein the thrombectomy apparatus comprises an inner catheter having a distal end and a distal end opening, a flexible tube extending along an outer diameter of the inner catheter and over the distal end of the catheter, and an outer catheter securing a distal end region of the flexible tube against the outer diameter of the inner catheter, so that the guidewire passes through a lumen of the catheter and the flexible tube; pulling the flexible tube proximally from off of the outer diameter of the catheter and into the catheter lumen so that a lubricious proximal leader region of the flexible tube slides and inverts over the distal end opening, until a non-lubricious distal region of the flexible tube is drawn into the inner catheter; and drawing a clot into the inverted flexible tube as the flexible tube is drawn into the catheter.

A method of mechanically removing a thrombectomy may include: advancing a guidewire adjacent a clot in a blood vessel; advancing a thrombectomy apparatus distally over the guidewire, wherein the thrombectomy apparatus comprises a catheter having a distal end and a distal end opening and a flexible tube extending along an outer diameter of the catheter and over the distal end of the catheter, so that the guidewire passes through a lumen of the catheter and the flexible tube; pulling the flexible tube proximally from off of the outer diameter of the catheter and into the catheter lumen so that the flexible tube slides and inverts over the distal end opening; pulling or pushing the flexible tube distally out of the distal end of the catheter so that the flexible tube slides and inverts over the distal end opening and over the outer diameter of the catheter; and drawing a clot into the inverted flexible tube as the flexible tube is drawn into the catheter.

In any of the methods described herein, the guidewire may be positioned at least partially within the clot in the blood vessel.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1H illustrate one variation of an apparatus for mechanically removing an object such as a clot form a body region. FIG. 1A shows a catheter portion of the apparatus; FIG. 1B shows an enlarged view of a distal end (opening) of the catheter; FIG. 1C shows an example of a distal tractor region of a flexible tube (tractor tube), showing the expandable first end region of the flexible tube in a collapsed (non-expended) configuration, while FIG. 1D shows the same distal tractor region with the expandable first end region expanded. FIG. 1E shows an assembled mechanical thrombectomy apparatus with the flexible tube extending through the catheter and doubling back over the distal end of the catheter so that the expandable first end region of the flexible tube (forming part of the distal tractor region) is at least partially outside of the catheter and in a non-expanded state. FIG. 1F shows the apparatus of FIG. 1E with the expandable first end region expanded. FIGS. 1G and 114 illustrate the use of the apparatus of FIGS. 1E and 1F to remove a clot by drawing the flexible tube proximally and/or advancing the catheter distally towards the clot so that the expandable first end region inverts as it is drawn into the distal end of the catheter, pulling the clot into the catheter.

FIGS. 2A-2D show variations of flexible tubes (tractor tubes) that may be part of the apparatuses described herein. FIG. 2A shows the distal end of the flexible tube including the distal tractor region comprising the expandable first end region at the distal end, adjacent to a less-expandable second end region. In FIG. 2B the expandable first end region is formed of a plurality of woven fibers. In FIG. 2C the expandable first end region is formed of a sheet of material having a plurality of small pores throughout. In FIG. 2D the expandable first end region is doubled over the less-expandable second end region.

FIGS. 3A-3F illustrate the in vivo deployment and operation of one example of a mechanical thrombectomy apparatus. In this example, the distal tractor region is pushed through the catheter after positioning the catheter near a clot until the distal tractor region is exposed from the distal end of the clot (FIGS. 3A-3D) so that the expandable first end region expands to the intima of the vessel; the catheter is then advanced between the expandable first end region and the less-expandable second end region (FIGS. 3D-3E), and the expandable first end region is drawn into the catheter so that it inverts and pulls the clot into the catheter (FIGS. 3E-3F).

FIGS. 6A and 6B illustrate a mechanical thrombectomy apparatus including a catheter and flexible tube (tractor tube) extending through the catheter and doubling back over the distal end of the catheter (forming the distal tractor region) and an outer catheter or release protector catheter over the distal tractor region. FIG. 6A shows the apparatus positioned near a clot; FIG. 6B shows the apparatus used with a guidewire through the guidewire lumen of the apparatus for positioning and operating the apparatus.

FIGS. 7A-7D illustrate operation of a thrombectomy apparatus as shown in FIGS. 6A-6B, showing positioning the distal end/distal tractor region adjacent to the clot (FIG. 7A), then pulling the clot into the catheter (FIGS. 7B-7C) and finally removal of the clot and flexible tractor tube (FIG. 7D).

FIG. 10A shows one variation of a handle (proximal) handle for actuating an apparatus such as the thrombectomy apparatuses described herein. The handle may be coupled and may, separately or in a coordinated fashion, actuate movement of the catheter and flexible (tractor) tube, including the distal tractor region.

FIG. 10B shows another example of a proximal handle for an apparatus as described herein, which includes controllers for controlling (separately or together) actuation of the catheter and/or inner flexible tractor tube.

FIG. 11A shows another example of a proximal handle for an apparatus including a thrombectomy apparatus as described herein.

FIG. 11B is a mechanical schematic illustrating operation of a handle for an apparatus as described herein.

In FIG. 12A an outer tubing (e.g., an outer catheter or release protector catheter over the distal tractor region) covers at least the end of the expandable distal end region. In FIG. 12B the expandable first end region of the distal tractor region may include a band, adhesive, weld (e.g., frangible adhesive or other attachment), clap, grasper, or the like, releasably securing the expandable first end region to the outer diameter of the catheter.

FIGS. 13A and 13B illustrate examples of the proximal end region (puller region) of the flexible (e.g., tractor) tube of the apparatuses described herein. FIG. 13A shows an example in which the proximal end of the tractor tube forms a pull wire that is radially offset from the lumen of the tube; a guidewire may still pass through the lumen of the tube (and catheter) for operation of the device, as shown. FIG. 13B shows an example in which the pull wire (or rod, member, etc.) is formed of a separate material than the rest of the flexible tractor tube.

FIGS. 15A-15D illustrate flexible (tractor) tubes having shaped expandable first end regions. In particular, these different expandable first end regions may be pre-set to different diameters which may help draw in and/or break the clot up within the catheter. FIG. 15A shows a first example in which the expandable first end regions is coupled to a puller portion by a plurality of pull wires. The expandable first end regions is shown not inverted over the more proximal portion of the flexible tubular member (tractor tube) in these examples. FIG. 15B shows a plurality of expandable end regions connected by a plurality of pull wires that may not be radially expandable. FIG. 15C shows an expandable first end region having a plurality of pre-set diameters. FIG. 15D shows an expandable first end region coupled to a more proximal puller portion of the tractor tube by two or more bundles of the filaments forming the expandable first end region.

FIG. 16 illustrates another example of an expandable first end region that includes a plurality of releasable attachments to the outer diameter of the catheter; these releasable attachments (which may be frangible, elastic, etc.) can be released by applying sufficient force to allow the distal tractor region to be pulled into the catheter for actuating the apparatus.

FIG. 17 illustrates an example in which the expandable first end region is loaded (e.g., spring loaded, compressed, etc.) over the outer diameter of the distal end region of the catheter and releasably locked or otherwise held in place, e.g. by a reliable attachment; this releasable attachment may prevent deployment of the apparatus until actuation, and the loading of the expandable first end region may make it easier for the distal tractor region to invert over the distal end of the catheter to draw a clot into the apparatus.

FIGS. 19A and 18B illustrate assembly methods for assembling an apparatus as descried herein.

FIG. 21A shows an example of an expandable first end region prior to coupling to a catheter. FIG. 21B illustrates the expandable first end region within a vessel (glass tube) being drawn into a catheter by pulling the proximal end of the flexible (tractor) tube. FIG. 21C shows the distal end region of the apparatus including the expandable first end regions doubled over the distal end region of the catheter. FIG. 21D illustrates the apparatus of FIG. 21C drawing a clot into the catheter.

FIGS. 23A-23D illustrate a mechanical thrombectomy apparatus as described herein capturing a blood clot and drawing it into the apparatus.

FIG. 23E illustrates the clot held within the flexible tractor tube after the flexible tractor tube has been removed from the catheter (e.g., proximally).

FIGS. 25A-25F illustrate another variation of a distal tractor region of a flexible tractor assembly in which the expandable first end region (e.g., the distal end region of the distal tractor region) is formed of a plurality of filaments or strips, similar to that shown in FIG. 24; the distal end of the catheter includes channels, as shown in FIGS. 25A-24B; the strips may fit within these channels, as shown in FIGS. 25C-25D. FIGS. 25E and 25F show sectional views through FIGS. 25C and 25D.

FIGS. 26A and 26B show a variation of the apparatus of FIGS. 25A-25F with an outer sleeve (e.g., an outer catheter or release protector catheter or other outer sleeve/protector)

FIGS. 27A and 27B show a sectional view through the apparatus of FIGS. 26A-26B.

FIG. 32 illustrates another example of an apparatus as described herein in which the distal-most end of the expandable first end region is fixed to a portion of the distal end of the catheter; the rest of the expandable first end region is sufficiently elastic/flexible to be drawn into the catheter (pulling a clot with it). The flexible tractor assembly may then be left retracted and the entire apparatus withdrawn. This example may include an optional vacuum.

FIG. 33 is another example of an apparatus in which the puller portion of the flexible tractor assembly is formed of the same material as the distal tractor region but may be laminated or otherwise reinforced to have less flexibility/stretchability than the distal tractor region.

FIG. 34 illustrates another example in which the distal tractor region is adapted to compress the clot when draw into the catheter.

FIGS. 38A and 38B illustrate another variation of an apparatus and method of using the apparatus to remove material from within a vessel, wherein the apparatus is an "infinite" tractor mechanism, in which a large amount of tractor material (e.g., mesh) is stored in an external holding region, wound-up but dispensable over an extended use.

DETAILED DESCRIPTION

Figure 1E:
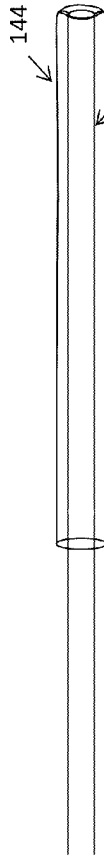

In general, described herein are methods and apparatuses for mechanically removing objects from a body. Although these methods and apparatuses may be adapted for use to remove a variety of objects from a variety of regions of the body, they may be particularly well suited for removal of blood clots from within a lumen of a blood vessel. Thus described herein are mechanical thrombectomy apparatuses (e.g., device and systems).

The apparatuses described herein (e.g., mechanical thrombectomy apparatus for removing a clot from a vessel) may be assemblies including an elongate catheter having a distal end and a distal end opening, and a flexible tractor assembly at least partially within the catheter, where the distal end region of the tractor assembly is configured as a distal tractor region that at least partially extends within the catheter and doubles back over the distal end of the catheter. The tractor assembly may include a proximate pusher region which is connected to the distal tractor region. The flexible tractor assembly includes an elongate lumen that is configured to allow passage of a guidewire. The flexible tractor assembly is also configured to slide along the long axis within the catheter lumen and invert over the distal end opening of the catheter when the proximal end region is pulled proximally. The tractor assembly may be referred to herein as a flexible tractor assembly, flexible tractor portion, flexible tractor tube, or simply a flexible tube, and is typically positioned and longitudinally slideable within the catheter, and arranged so that the distal end region ("distal tractor region") doubles back over the distal end of the catheter.

For example, FIG. 1A shows one variation of a catheter that may form part of the apparatuses described herein. In this example, the catheter 100 includes a distal end region 103 that includes a distal end 105. The distal end region may have an increasing softness (measured by durometer, e.g., shore durometer) except that the very distal tip (distal end 105) may be substantially less soft than the region immediately proximate to it. Thus, although the distal tip region (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

The catheter 100 may also be referred to as the inner catheter or the tractor catheter. Any appropriate type of catheter may be used, including microcatheters appropriate for neurovascular use.

In some variations the distal end 105 of the catheter is adapted so that the distal tractor region may slide and invert over the distal end of the catheter without being caught (binding) or without substantial friction. For example, in some variations the distal tip (end) may be curved or radiused 109 as shown in FIG. 1B, particularly on the outer surface (e.g., the transition from outer diameter to inner diameter). In some variations the distal tip includes one or more channels, as shown and described in FIGS. 25A-28, including channels around the distal-facing edge, to guide the sliding of the distal tractor region.

FIG. 1C shows an example of a flexible tractor tube 140. In FIG. 1C, the tube is flexible and elongate (having a generally greater length than the catheter 101), and includes a distal tractor region 142 that includes a distal-most expandable first end region 144 that is configured to fold over the immediately proximal region 146, which may be a less-expandable second end region. In general the expandable distal end region is configured to expand to a radial diameter that is between 1.3 and 10 times the diameter of the inner diameter of the catheter when unconstrained. FIG. 1D shows the expandable distal end region of FIG. 1C in an expanded configuration. Thus the expandable distal end region may be biased to expand open. The expandable distal end region may be formed as a mesh, woven or sheet of material and is generally adapted to grasp the object to be removed (e.g., blood clot).

Figure 1F:
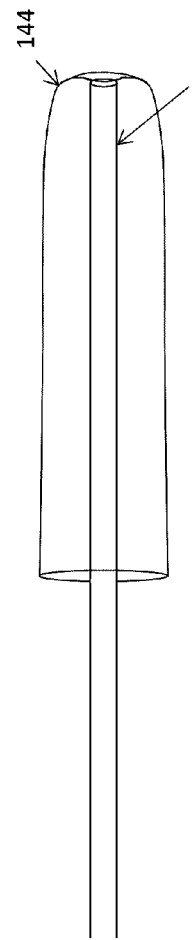

The flexible tractor tube shown generically in FIG. 1C is shown with the expandable distal end region doubled back over itself (e.g. over the more proximal less-expandable second end region) in FIG. 1E. In FIG. 1E, the expandable distal end region is collapsed, while in FIG. 1F the expandable distal end region is expanded. In general, the expandable distal end region may be distinguished from the proximal less-expandable second end region, however in some variations the entire flexible tractor tube may comprise and expandable material (e.g., mesh, weave, etc.) that is pushed and/or pulled within the catheter and does not include a proximal less-expandable distal end region.

Figure 1G:
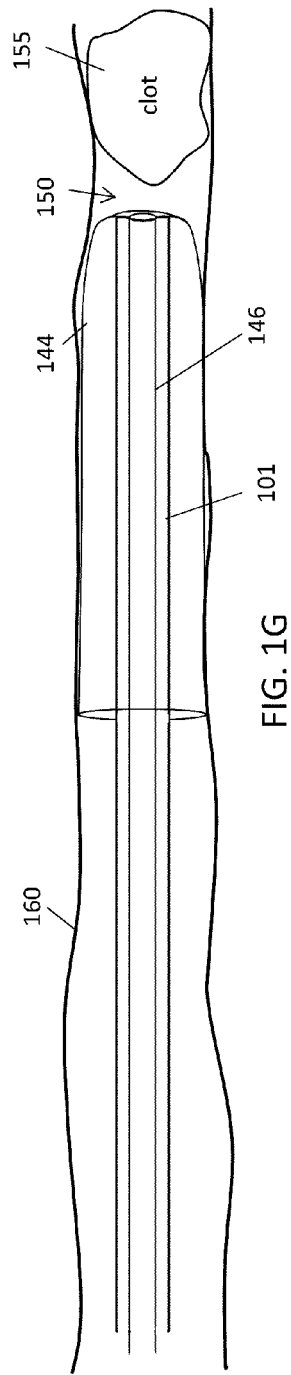
Figure 1H:
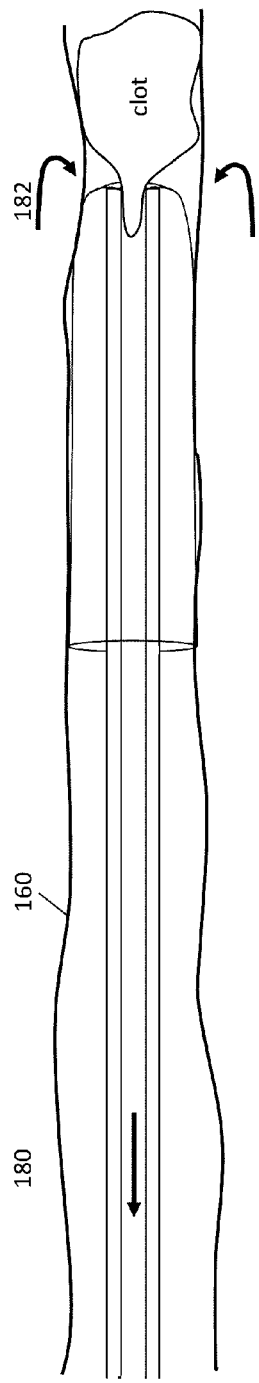

FIGS. 1G and 1H illustrate the removal of a clot using an apparatus such as the apparatus assembled from the components of FIGS. 1A and 1E. In this example the apparatus is configured as a thrombectomy apparatus including a catheter 101 and a flexible tractor tube that includes an expandable distal end region 144 that extends over the distal end region of the catheter and doubles-over the distal end of the catheter so that the expandable distal end region is continuous with an inner proximal less-expandable (in this example, less-expandable includes non-expandable) second distal end region 146 that extends proximally within the catheter and forms an inner lumen that may pass a guidewire. The proximal end of the flexible tractor tube (not shown) may include a pusher/puller member that may be a rod or other member that is continuous with the distal end region (distal tractor region 140). In FIG. 1G the apparatus is shown positioned and deployed within the vessel 160 near the clot 155. The clot may be drawn into the catheter by withdrawing the distal tractor region 140 into the catheter 101, as indicated by the arrow 180 showing pulling of the inner portion of the flexible tractor tube (e.g., using a handle, not shown) resulting in pulling the expandable distal end region into the catheter distal end and inverting the expandable distal end region so that it is pulled into the catheter, shown by arrows 182. The distal end of the expandable distal end region may be "loose" relative to the outer wall of the catheter, or it may removal attached or in some variations permanently attached.

In general, positioning these apparatuses and actuating them may be challenging because they must be highly flexible, both before actuating and during operation. For example, in general, the flexible tractor tube must not increase the stiffness/flexibility of the catheter, and particularly the distal end region of the catheter too much, or it may be too difficult and/or dangerous to maneuver, particularly within tortious vessels of the neurovasculature. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

For example, FIG. 2A shows a flexible tractor tube 201. In this example, the flexible tractor tube includes a distal tractor region 242 with an expandable first end region 244 and a less-expandable second end region 246 that is distal to a proximal pusher region 201. The entire flexible tractor tube is hollow and may pass a guidewire (not shown). The various regions of the flexible tractor tube may be made of the same material (e.g., a woven, braided, etc. filament or filaments) or they may be made of different materials.

FIG. 2B shows a flexible tractor tube having a distal tractor region, or at least the expandable first end region 244' formed of a plurality of woven fibers. Alternatively the expandable first end region may be formed of one (or more) knitted fibers, or a combination of woven and knitted fibers. The expandable first end region may be biased open (as shown) by a shape-setting property of the fibers or woven/knitted pattern or by the inclusion of one or more biasing members (e.g., rings, springs, bands, filaments, etc.) that tend to bias at least the distal end region of the expandable first end region open.

FIG. 2C illustrates another variation of an expandable first end region formed of a sheet of material that includes a plurality of openings (e.g., pores, perforations, passages, windows, etc.). These openings may be any sizes, including non-uniform sizes (e.g. a range of sizes) or uniform sizes. The sizing of these opening through the sheet may depend on the material used, e.g., polymeric material (PTFE), silicone materials, polyurethanes, shape memory alloys, etc. In some variations it is beneficial to have a porosity of greater than >60% (greater than 70%, greater than 75%, greater than 80%, greater than 85%, etc., between 60-95, 65-95, 70-95%, etc.) of the sheet.

Figure 2D:
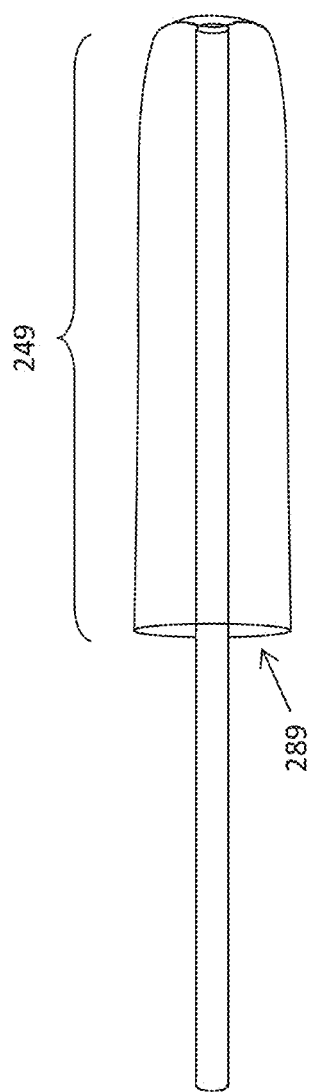

In any of these variations, the distal tractor region is configured so that it may be inverted (e.g., doubled over) itself, as shown in FIG. 2D. In some variations the apparatus may be performed so that the expandable first end region is inverted over the itself and/or over the distal end region of the catheter, or it may be configured so that it can be deployed and inverted over the distal end of the catheter in vivo (e.g., within the blood vessel). In general, before the apparatus can be actuated the catheter may be inserted between the expandable first end region and the region proximal to the expandable first end region on the flexible tractor tube, which may, in some variations, be the less-expandable second distal end region. This space 289 may be held open by a biasing member at or near the distal end of the expandable first end region. As mentioned, this expandable first end region opening biasing member may be a ring, band, spring, coil, or the like, and may be made of a biasing element (e.g., shape-set material, such as a shape memory alloy), rubber or other polymeric material, or the like.

Figure 3D:
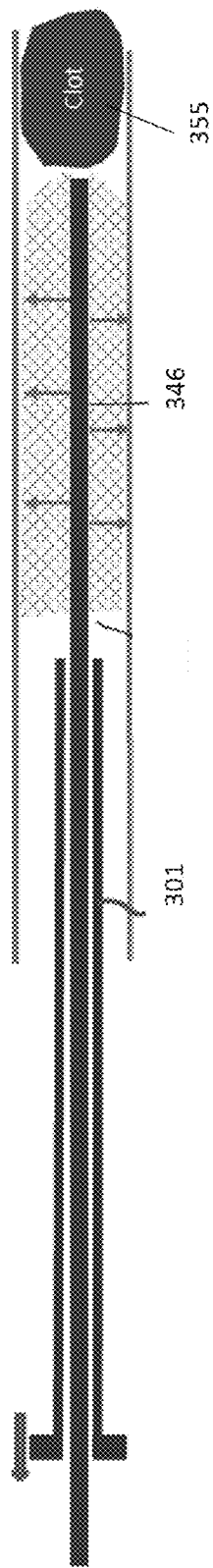
Figure 3E:
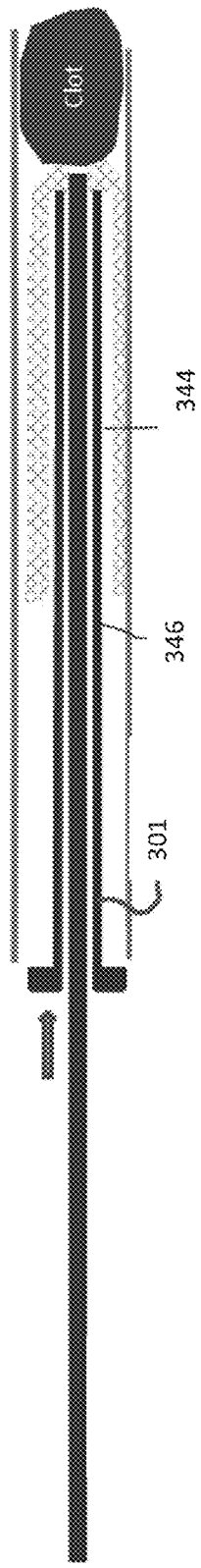

In vivo deployment of the apparatuses described herein may provide a number of advantages for users operating the apparatus, despite associated challenges. FIGS. 3A-3F illustrates one example of a thrombectomy apparatus that is configured for in vivo deployment. In this example, the apparatus includes a catheter 301 that may be positioned (as with any of the variations described herein) using a guidewire 313. The guidewire may be extend to or into (or through) the object to be removed, shown as clot 355 in FIG. 3A within a blood vessel 360. The catheter of the apparatus may be inserted with or after the guidewire, and the catheter may be positioned near (e.g., adjacent to or immediately adjacent to) the clot with or without the flexible tractor tube at or near the distal end of the catheter. In FIG. 3A the catheter is positioned after the guidewire has been positioned, and, as shown in FIG. 3B, is removed from the vessel. The guidewire may be a wire, smaller catheter or combination of devices that may be positioned (e.g., steered) to and/or through the clot. Following positioning of the catheter, the inner flexible tractor tube 340 including the distal tractor region 342 is pushed through the catheter to the distal end region of the catheter, as shown in FIG. 3C. In this example the distal end of the flexible tractor tube forming the distal tractor region includes an expandable first end region shown as a mesh 344 that is connected to a proximal less-expandable second end region that is continuous with the rest of the flexible tractor tube, at the proximal end (pusher region 305). The braided mesh 344 of the expandable first end region is pre-inverted over the outside of the tubular second end region/pusher region in a collapsed (non-expanded) configuration, and can be slide through the inner lumen of the catheter, and (when the guidewire is left in position or used adjust the position) over the guidewire (not shown). As shown in FIG. 3D, the distal tractor region of the flexible tractor tube may then be exposed to the outside of the catheter by extending (in this example either pushing the flexible tractor tube distally and/or pulling the catheter proximally, allowing the expandable first end region of the distal tractor region (shown as mesh) 344 to expand along the length of the first end region. In FIG. 3D this is shown as a stent-like structure that may expand fully to the intima of the vessel forming a separation between the expandable first end region and the less-expandable (in this case non-expandable) second end region 346. In particular the expansion of the first end region may be greater than 1.3 times the diameter of the inner lumen of the catheter (e.g., greater than 1.5×, greater than 2×, greater than 2.2×, greater than 2.5×, greater than 3×, greater than 3.5×, greater than 4×, greater than 5×, greater than 6×, greater than 7×, greater than 8×, greater than 9×, greater than 10×, etc.).

In FIG. 3D, the catheter is slid distally between the first and second end regions of the distal tractor region. The clot may then be removed by withdrawing the expandable first end region proximally into the catheter either or both by pulling the flexible tractor tube (e.g., proximal puller region) proximally and/or advancing the catheter distally. In some variations it may be beneficial to both advance the apparatus and particularly the catheter, while withdrawing the expanded first end region and inverting it into the catheter. The catheter may be advanced more quickly than the flexible tractor tube is withdrawn.

Figure 3F:
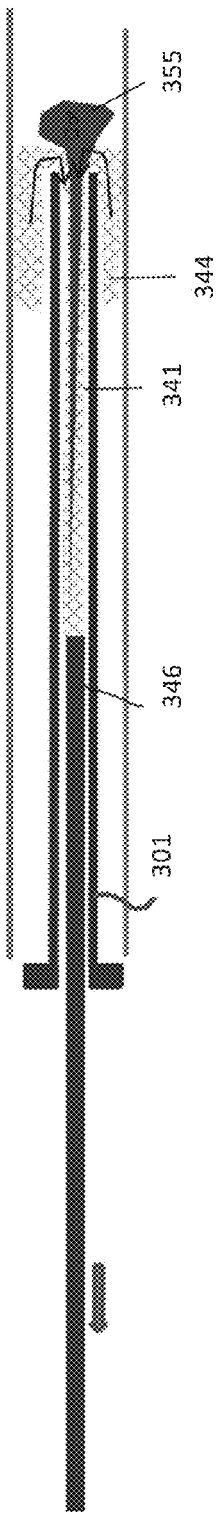

As shown in FIG. 3F, the clot 355 may be drawn in to the catheter with the expandable first end region.

Figure 4A:
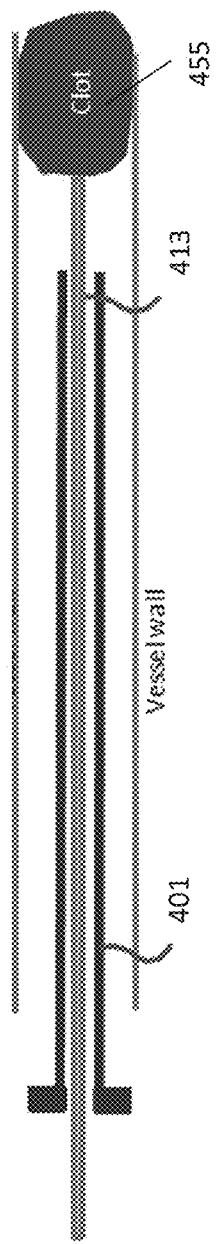
FIGS. 4A-4F illustrate in vivo deployment and operation of another example of a mechanical thrombectomy apparatus. In this example, the expandable first end region of the flexible (tractor) tube is deployed after positioning the catheter portion (FIGS. 4A-4B) by extending the expandable first end region out of the distal end of the catheter so that the expandable first end region double-back over the distal end region of the catheter (FIGS. 4C-4D). Once exposed and deployed, the expandable first end region may be drawn back into the catheter with or without advancing the catheter distally to pull the clot into the catheter (FIG. 4F).
Figure 4B:
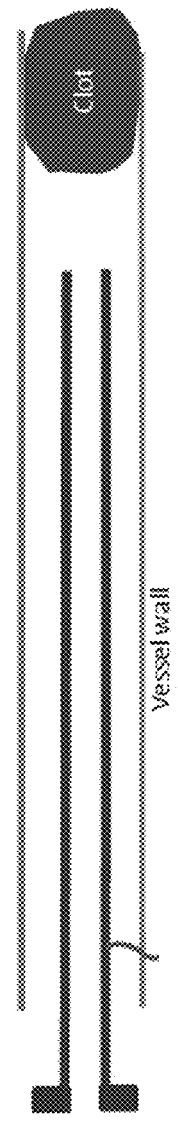
Figure 4C:
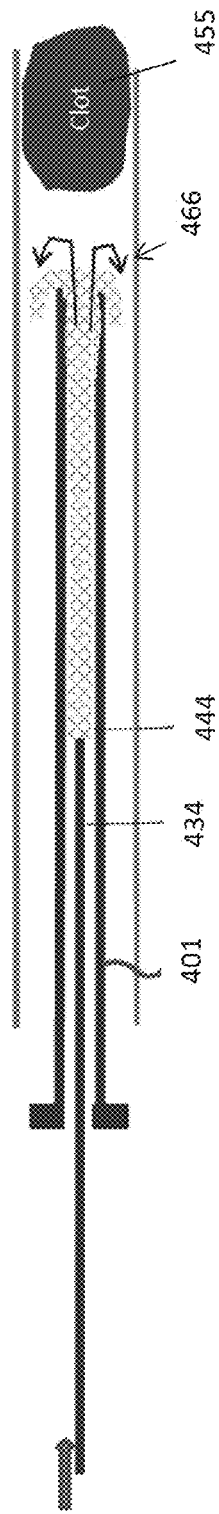
Figure 4D:
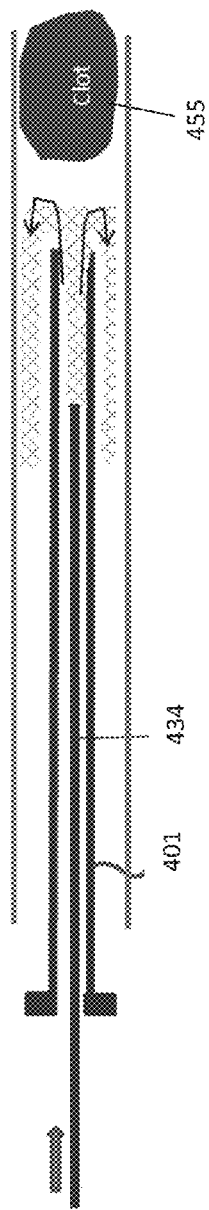
Figure 4E:
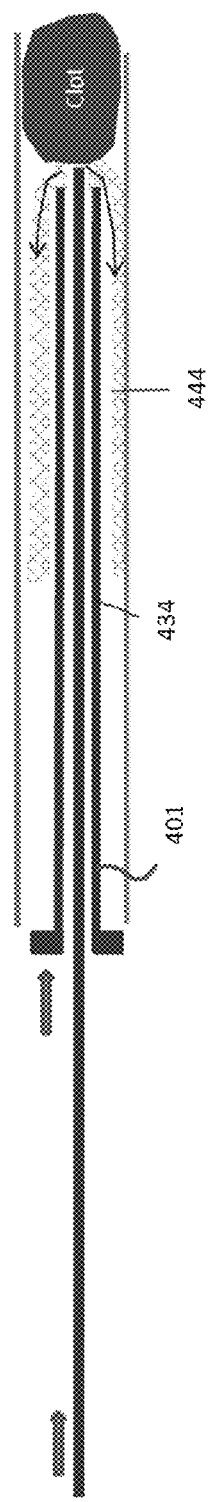
Figure 4F:
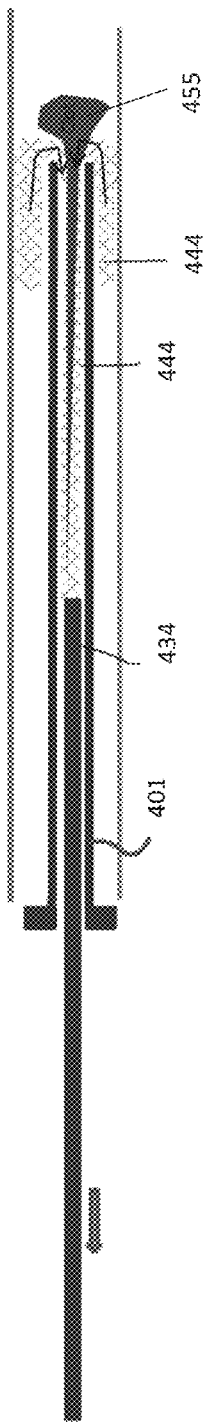

Another variation of an in vivo deployment method and apparatus is shown in FIGS. 4A-4F. In this example, the self-expanding first end region of the flexible tractor tube is configured to self-expand over end of the catheter as it is pushed out of the catheter so that it will slide over the distal end of the catheter. As described above for FIGS. 3A-3B, the apparatus may be positioned using a guidewire 413 or the like. In FIG. 4A, the catheter 401 is positioned over the guidewire 413 adjacent to the clot 455 to be removed. In FIG. 4B the guidewire may be (optionally) removed, or (preferably) left in place. The flexible tractor tube 434 including the distal tractor region may then be moved distally within the catheter and extended with the expandable first end region 444 out of the distal end so that it inverts 466 over the distal end and slide proximally over the distal end region, as shown in FIG. 4C. This process may be aided by pushing the apparatus distally within the lumen of the vessel, as the expansion of the first end region 444 may help secure it against the wall of the vessel, as shown in FIGS. 4D-4E. Once exposed, the expandable first end region may be withdrawn into the apparatus by pulling the flexible tractor tube 434 proximally and/or advancing the assembly (or at least the catheter) distally, as shown in FIG. 4F. The clot 455 may then be drawn into the apparatus.

Figure 5A:
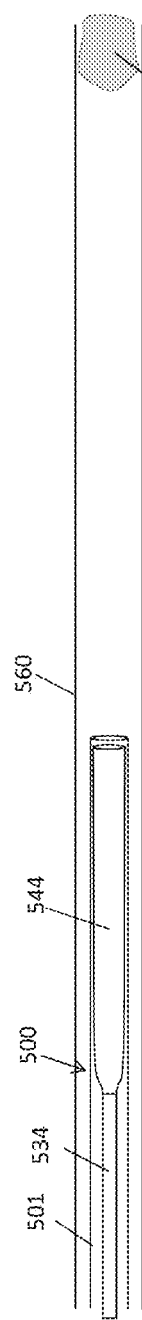
FIGS. 5A-5E illustrate in vivo deployment and operation of another example of a mechanical thrombectomy apparatus in which the expandable first end region is extended distally out of the end of the catheter after it has been positioned within the vessel near the clot (FIGS. 5A-5C). Once the expandable first end region has been extended and allowed to expand within the vessel, the catheter and the rest of the flexible tube within the catheter may be advanced distally (FIG. 5D) so that the expandable first end region doubled over the distal end as shown. Thereafter the expandable first end region may be drawn back into the catheter with or without advancing the catheter distally to pull the clot into the catheter (FIG. 5E).
Figure 5B:
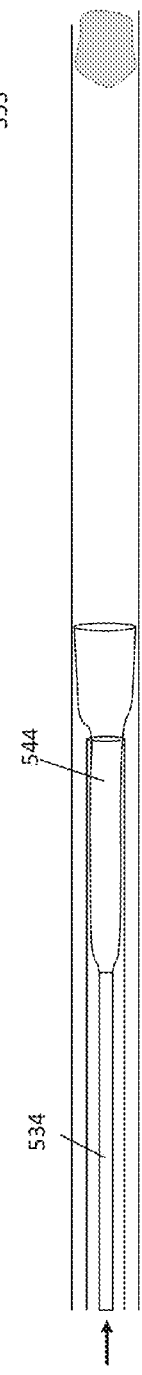
Figure 5C:
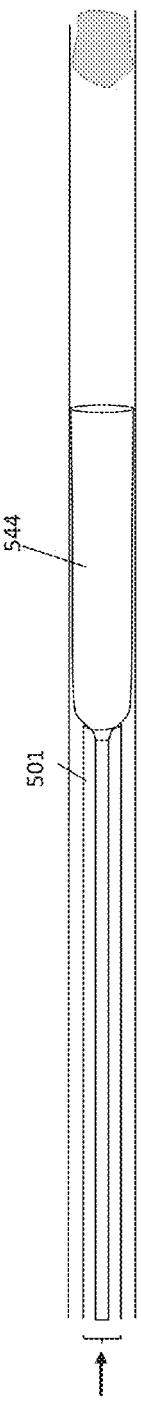
Figure 5D:
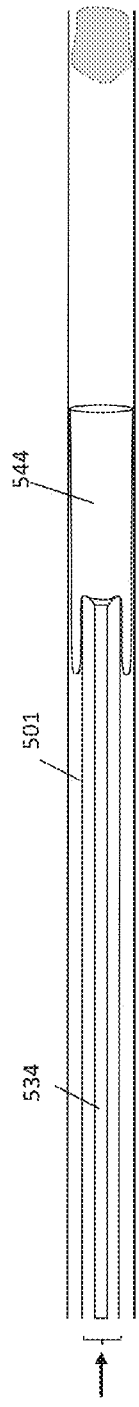
Figure 5E:
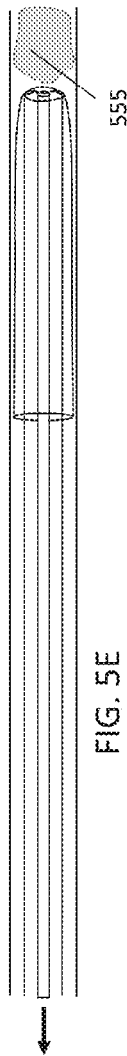

FIGS. 5A-5E illustrate another variation of an in vivo deployment and thrombectomy (clot removal) method using a mechanical thrombectomy apparatus. In FIG. 5A, the apparatus 500 including a catheter 501 and an inner flexible tractor tube 534 is advanced (e.g., over a guidewire, not shown) to be near a clot 555. In this example (which may be relevant to any of the methods described herein) the apparatus is positioned with the flexible tractor member having the un-deployed distal tractor region already positioned distally near the distal end region of the apparatus. As shown in FIG. 5B, the expandable first end region 544, which is in a collapsed configuration within the catheter 501 in FIG. 5A, is pushed out of the distal end of the catheter and expands to the walls of the lumen as shown in FIGS. 5B-5C. Once pushed out and expanded, the catheter and the portion of the flexible tractor tube within the catheter may be advanced distally, as shown in FIG. 5D, causing the expandable first end region 544 to invert, doubling over the distal end region of the catheter 501. By FIG. 5E, the apparatus has been deployed near the clot 555 and may be actuated as already described to remove the clot, but pulling the expandable first end region of the distal tractor region into the catheter, so that it inverts and draws the clot into the catheter. The catheter may optionally be simultaneously advanced. Note that the method of in vivo deployment described above may also be used to load an apparatus for insertion into a body in order to position the catheter radially between the expandable first end region and the more proximal portion of the flexible tractor tube.

FIG. 6A illustrates an example of another variation of a thrombectomy apparatus having a flexible tractor tube 634 with a flexible first (distal) end region 644 formed in this example of a braided (e.g., woven) or knitted material, where the flexible first end region (tractor region) is inverted over the distal end of a catheter 601 and attached to the proximal end region of the flexible tractor tube 634. As in any of the apparatuses described herein this proximal end region of the flexible tractor tube may be a hypotube, catheter, or laminated weave/mesh or woven material that is pushable/pullable within the catheter and is attached at its distal end to the flexible tractor region (e.g., distal tractor region), including in some variations an expandable first end region. Note that in some variations the distal tractor region (the first end region) may not be expandable but may be just flexible.

In FIG. 6A, the first end region of the distal tractor region attached to the flexible tractor tube is covered by an outer catheter or sleeve (protector) 677. In this example, the apparatus also includes a mid-catheter 679 between the inner catheter 601 and the protector catheter or sleeve 677. In some variations the flexible first end region 644 may be attached to this mid catheter, including removably attached so that pulling the flexible tractor tube 634 proximally will disengage it and allow the mesh (the flexible first end region 644) to deploy in the vessel. In the variation shown in FIG. 6A the flexible first end region 644 is not attached to the middle catheter 679.

Any of the apparatuses described herein, including the apparatus shown in FIG. 6A may be used with (and may include) a guidewire 633 as shown in FIG. 6B. FIGS. 7A-7D illustrate the operation of the apparatus shown in FIGS. 6A-6B to remove a clot 755. In this apparatus the proximal end of the flexible tractor tube 734 may be coupled to a vacuum source (not shown) which may be actuated when withdrawing the tractor tube 734 proximally to invert the distal tractor region over the end of the catheter. In FIG. 7A the apparatus is positioned near the clot 755. In FIG. 7B, the distal tractor region is inverted and pulled into the catheter by pulling the flexible tractor tube 734 as shown by the arrow. In this example the distal tractor region is not expanded because it remains covered by the outer sleeve 777, as shown in FIGS. 7B and 7C. The apparatus may be advanced distally toward/over the clot either or both by pushing or by the action of pulling the distal tractor end region (shown in this example as a mesh 744) proximally to invert it over the distal end of the catheter. Once the clot is removed, the apparatus may be withdrawn and pulled out of the vessel, as shown in FIG. 7D.

Figure 8:
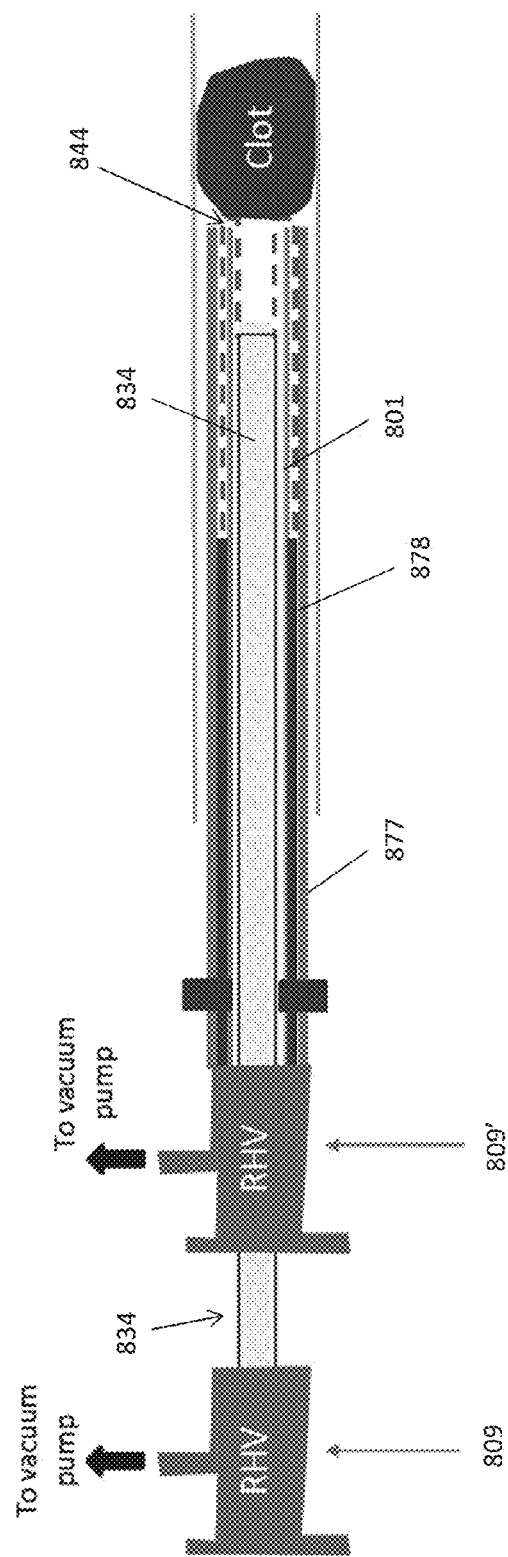
FIG. 8 shows a thrombectomy apparatus including an optional vacuum source.

As mentioned above, any of these variations may include one or more vacuum sources. FIG. 8 illustrates one example including a vacuum source showing a first optional vacuum source at the proximal end coupled to the lumen of the flexible tractor tube 834. For example, the coupling with the vacuum and the tractor tube 834 may be a rotating hemostatic value (RHV) as shown. In FIG. 8 a second (optional) vacuum connection is made between the (optional) outer catheter 877 and the inner catheter 801 or an (optional) middle catheter 878. Vacuum may be applied at any appropriate portion of the method, including during retraction of the flexible tractor rube 834 to remove the clot.

Figure 9A:
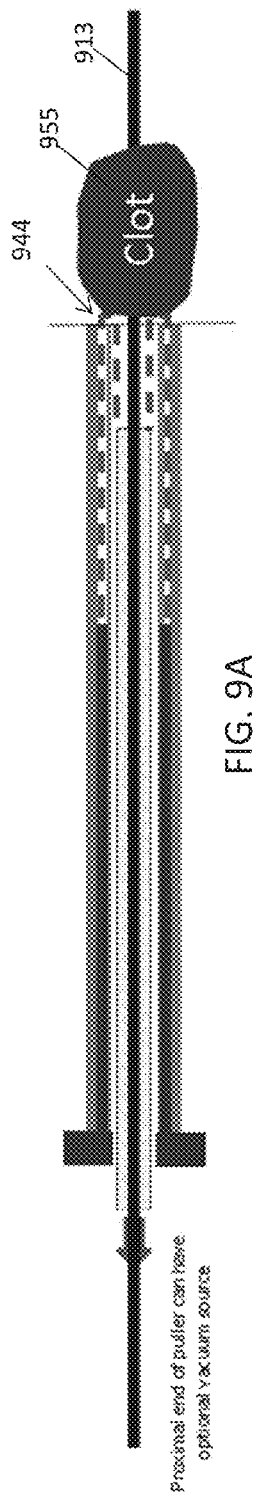
FIGS. 9A-9D illustrate operation of a thrombectomy apparatus as described herein in combination with a guidewire. The guidewire may pass through the clot completely or partially and the apparatus may be actuated over the guidewire, providing enhanced stability and efficacy.
Figure 9B:
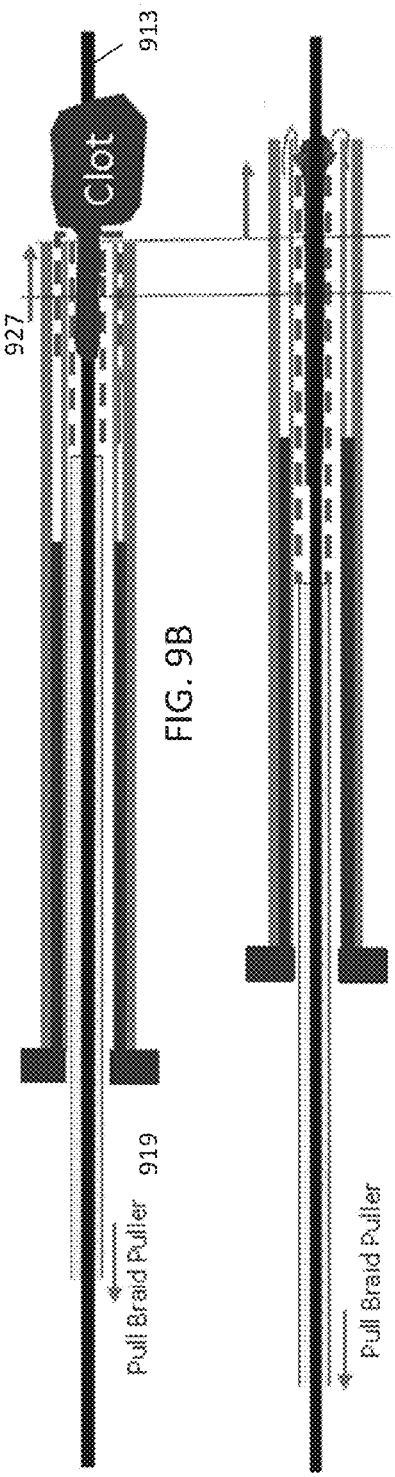
Figure 9C:
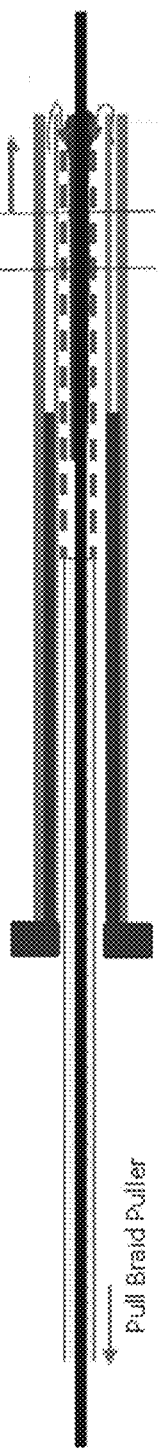

As mentioned, any of the apparatuses described herein may include a guidewire and may leave the guidewire in position during the procedure. FIGS. 9A-9D illustrate a method of removing an object (e.g., clot) when leaving a guidewire 913 in position. In this example, the apparatus is similar to the apparatus shown in FIGS. 6A-6B, and may include an optional vacuum source. In FIG. 9A the distal end of the catheter including the inverting portion of the flexible first end region 944 of the distal tractor region 944 is placed adjacent to the clot and actuated by pulling proximally to draw the clot into the catheter as shown in FIG. 9B. In this example the clot has been penetrated by the guidewire 913, thus the catheter tip with the inverting tractor region may be advanced forward over the guidewire by pushing on the catheter 927 and/or by pulling the tractor tube proximally 919. This may be continued until the entire clot is within the catheter, as shown in FIG. 9C.

In any of the variations described herein, the apparatus may include one or more markers or may be configured for use with one or more contrast agent to assist in visualizing the methods described. Further any of these methods may include visualization. Visualization may be indirect (e.g., using fluoroscopy or equivalent techniques) or direct, e.g., using one optical fibers for direct visualization down the apparatus (e.g., thought the lumen of the apparatus).

Figure 9D:
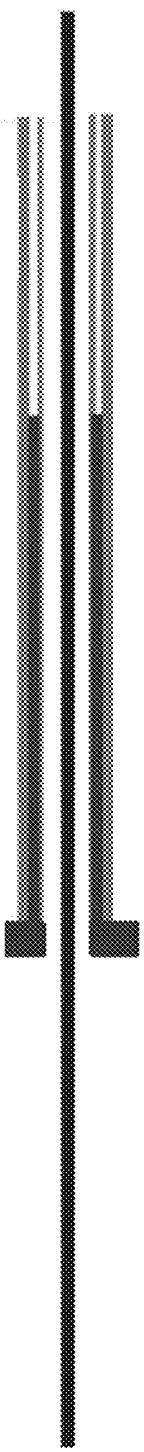

In FIG. 9D, the tractor tube with the captured object (e.g. clot) may be removed proximally from the apparatus and the removed material may be examined (e.g., via histological/cytological examination). The catheter may be subsequently or simultaneously removed. As mentioned above, when removing the object (e.g., clot) it may be desirable to pull back (proximally) the guidewire at the same time that the flexible tractor tube is pulled back proximally (not shown).

In some variations, the distal tractor region (e.g., braided/woven or knitted region) may grab onto the guidewire within the catheter and which may also help propel the apparatus distally over/toward the clot, as described in more detail in FIGS. 36 and 37A-37C, below.

In general, the rolling effect of the grabber (the distal tractor region) is activated by the motion of the catheter relative to the distal tractor region. If the distal tractor region is fixed proximally and the catheter is advanced, the distal tractor region may have a 1:1 grab ratio. If the distal tractor region is pulled though the catheter, the grabbing effect may be amplified. For example when the distal tractor region is pulled back (by pulling the tractor tube) and inverted into the inner catheter 1 unit to proximally within the catheter as the inner catheter is pushed 1 unit to distally, the grabbing effect is approximately 2×. If the distal tractor region is withdrawn into the inner catheter proximally two units as the inner catheter is advanced distally one unit, the grabbing effect may be approximately 3×. The concurrent motion of the distal tractor region and the catheter may be coordinated by a handle.

In general, any of the apparatuses described herein may include a handle. The handle may couple with the flexible tractor tube and/or the catheter (e.g., inner catheter) and/or any outer catheter (e.g., protector, sleeve, etc.). The handle may be configured to allow selective, separate actuation of the flexible tractor tube and/or the catheter and/or coordinate motion of these components. FIGS. 10A and 10B illustrate examples of handles that may be used. In FIG. 10A, the handle includes a drive mechanism to pull back the tractor tube, and therefore invert the distal tractor region over the distal end of the catheter and/or advance the catheter relative to the distal tractor region. In FIG. 10A, the handle include rotatable handle 1001 couled to a catheter drive 1003. The handle connects to both the catheter 1005 and the inner flexible tractor tube 1009 having a distal tractor region 1011. The handle may be configured so that the ratio of the advancing (distally) of the catheter versus the pull (proximally) of the tractor tube may be selected and/or may depend on a thread pitch of the catheter drive thread or other mechanical mechanism.

Another variation of a handle is shown in FIG. 10B. In this example the handle may be attached to the tractor tube to pull (or push) 1017 the tractor tube and therefore invert the distal tractor region over the distal end of the catheter, and another portion of the handle may be coupled to the catheter to push/pull the catheter 1015.

FIG. 11A shows another variation of a handle mechanism 1107 configured to pull the grabber (distal tractor region) of any of the apparatuses described herein by coupling to the proximal end of the tractor tube at an attachment site 1105, and/or advance the catheter by coupling to the proximal end of the catheter. Another example of a handle mechanism is shown schematically in FIG. 11B, showing a levering mechanism 1109 and a coupling to the inner tractor tube that may be fixed or adjustable.

In any of the apparatuses (e.g., mechanical thrombectomy apparatuses) described herein, the distal tractor region may be preloaded in/on the catheter so that it can be actuated by pulling the tractor rube coupled to the distal tractor region proximally and/or advancing the catheter distally. In preloaded variations in which the distal tractor region includes a flexible and/or expandable first end region (e.g., formed of a mesh and/or weave of material) that is doubled over the distal end of the catheter, the apparatus may be adapted to prevent inadvertent dislodging and/or expansion of the first end region before it has been positioned at or near the clot.

Figure 12A:
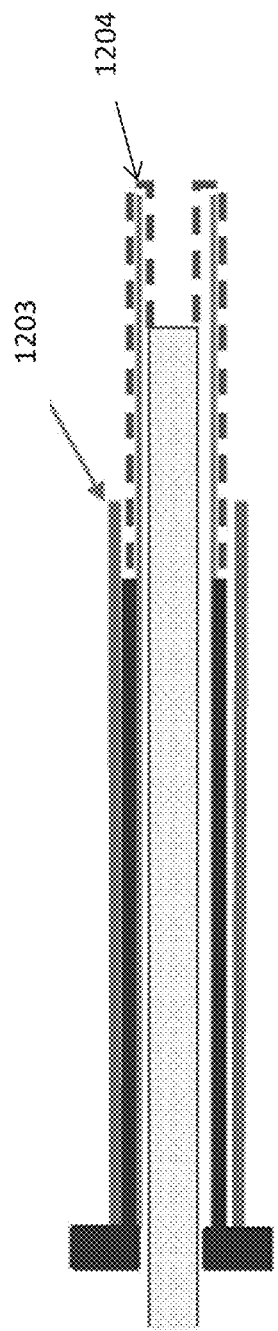
FIGS. 12A and 12B illustrate variations in which the expandable first end region of the flexible tractor tube of the apparatus is releasably secured to an outer surface of the catheter; prior to actuation of the apparatus, so that the distal tractor region can be drawn into the distal end of the catheter, the releasable attachment may be detached.
Figure 12B:
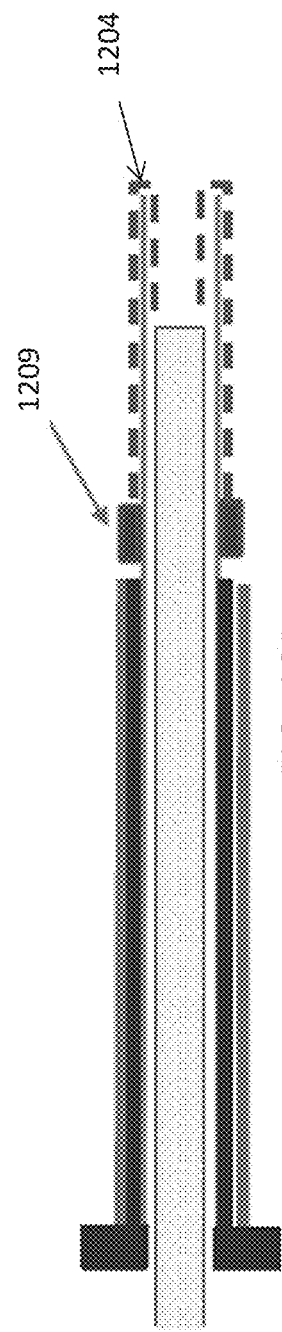

FIGS. 12A and 12B illustrate examples of releasable attachments for the distal tractor regions attached to the outside of the catheter. Any of these attachments may be released by the application of an appropriate amount of force (e.g. pulling force) applied to the proximal end of the flexible tractor tube. For example in FIG. 12A, the outer distal end of the distal tractor region (shown as mesh 1204) is covered by a shoulder or sock extending from an outer catheter or tubing 1203). Similarly in FIG. 12B, the outer distal end of the distal tractor region (shown as mesh 1204) is covered by a separate band, ring, or sock 1209. The distal tractor region may be prevented from collapsing or reducing in diameter when tension (e.g. pulling proximally on the tractor tube) by adding filaments (e.g., in braided or woven variations, additional braid filaments), by adding a coating, by heat setting to a larger diameter, and/or by adding an axial inter-braiding pull wire.

Any of the variations described herein may include a proximal pull rod or pull wire as part of the flexible tractor tube. Further, the proximal end region of tractor tube may be less flexible than the distal end (distal tractor region). FIGS. 13A and 13B illustrate examples of flexible tractor tubes. In FIG. 13A, the tube includes a proximal taper region in which the distal tractor region 1305 is formed of a material (e.g., mesh/woven material) that tapers proximally 1307 into a pull wire, leaving room for a guidewire 1309 and permitting the distal tractor region to invert over a catheter. The proximal pull-wire portion may be formed of the filaments forming the distal tractor region, e.g., in variations in which the distal tractor region is woven or braided. These filaments may be reinforced, e.g., by other materials such as polymers that help make it stiffer or more compliant. FIG. 13B shows another example in which the proximal end of the flexible tractor tube is formed of a pull wire 1315 that may be a separate material or an extension of the braid wire bundle attached to the distal end of the pull wire and forming the distal tractor region 1317.

Figure 14:
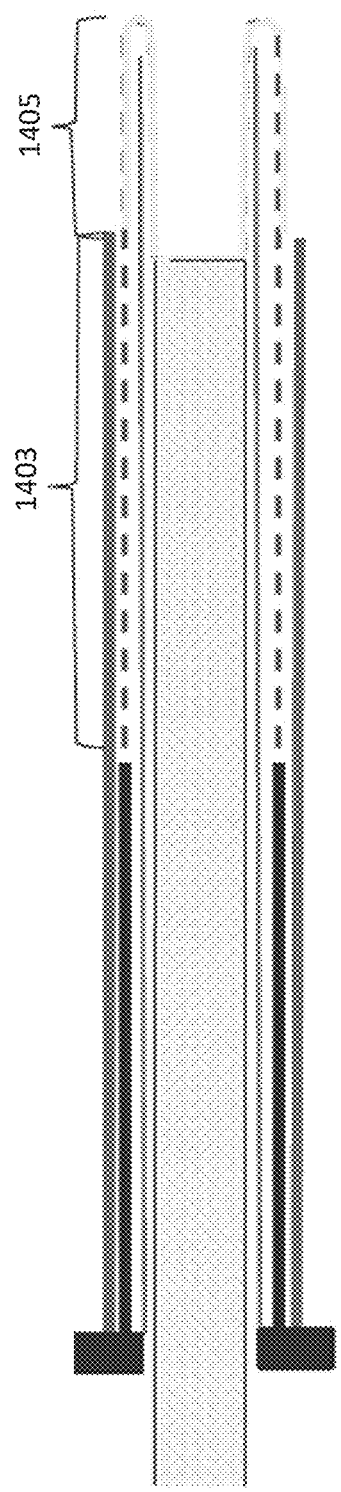
FIG. 14 illustrates a distal tractor region including a limited lubricious region near a proximal end region of the expandable first end region of the distal tractor region; other portions of the expandable first end region may not be lubricious, nor may other portions of the rest of the distal tractor region.

Any of the apparatuses described herein may be treated or adapted to reduce the force required to invert the distal tractor region over the end of the catheter. For example in some variations either the distal end may be treated to be lubricious, or all or a portion of the distal tractor region may be treated to enhance laboriousness. For example, in some variations only a portion of the distal tractor region, e.g., the portion that initially interacts/inverts over the distal end of the catheter is treated; the rest of the distal tractor region is not treated. FIG. 14 shows an example of such an apparatus. In FIG. 14, the proximal-most end 1405 of the expandable and/or flexible first end region (that is positioned outside of the catheter) is treated with a lubricous coating or formed of a lubricious material. The remaining portion (not shown to scale) of the first end region is not as lubricous 1403. Since the more proximal region 1405 is exposed to the vessel and the distal end of the catheter, it may more effectively track the target or allow the apparatus to track the target as well as start inverting over the distal end more effectively. This region may be made lubricious in any appropriate manner, including but not limited to coatings such as hydrophobic/hydrophilic coatings, and forming or including a more lubricious polymeric material (e.g. PTFE).

In general, any of the distal tractor regions described herein may be adapted to include different profiles, including pre-set to have (e.g., shape-set) profiles that may more readily slide/move over the distal end and/or grab a clot or other target object for removal. For example, FIGS. 15A-15D illustrate tractor tubes having different distal end profiles forming different distal tractor regions. In FIG. 15A for example, the distal tractor region includes a distal-most expandable and/or flexible first end region 1505 that is formed of a braided/mesh or woven material that is connected to proximal end of the tractor tube by a plurality of pull wires. These pull wires 1517 may be formed by the same wires or filaments forming the braided/mesh or woven distal end region. FIG. 15B shows another variation in which a plurality of discrete braided/mesh or woven distal end regions are connected by pull wires 1515; these pull wire regions 1515 may be less-expandable and/or flexible than the braided/mesh or woven regions 1516. In FIG. 15C, the distal end regions are braided/mesh or woven but pre-set to have different diameters. Thus these regions may have different shapes along their length; these shapes may be heat set to better grab or break up clot as they are pulled into the catheter. FIG. 15D illustrates an example of a braid or stent-like first end region 1521 that is connected to hypotube or other more proximal end region of the tractor tube 1520 by the same filaments or bundles of the same filaments forming the braided/mesh or woven distal tractor region 1523.

Any of the apparatuses described herein may also or alternatively include a plurality of releasable attachments to the outer surface of the catheter securing the distal tractor region (and particularly the distal end portion) to the outer surface. In FIG. 16, three rings 1603, 16.3', 1603" forming releasable attachment are shown securing the distal end of the distal tractor region 1644 to an outside of a catheter 1601. In this example, a polymer coating/film is attached or integrated with the braid forming the distal tractor region to help prevent it from sliding or slipping off of the catheter prematurely (e.g., until pulled by a user). The apparatus can include multiple attachments, as shown, radially positioned along the length of the catheter to help it stay secure to the outer diameter of the catheter delivery system. In some variations these releasable attachments are elastic member (e.g., a urethane ring) but may be frangible, and allowed to break to free the distal tractor region.

FIG. 17 shows another variation in which the releasable attachment is positioned so that a portion of the distal tractor region is spring-loaded (biased) to drive it in rolling over the distal end of the catheter and into the catheter lumen. In FIG. 17, The distal end of the distal tractor region 1704 may be secured (fixed, attached or loose but constrained) and a more proximal end region near the distal end of the catheter may be releasably secured to the catheter 1707. For example, a polymeric coating or film may be attached to the distal tractor region (shown as a braid 1744 in FIG. 17) and coupled to hold a portion of the distal tractor region 1705 between the distal end 1704 and releasable attachment site 1707 in tension (e.g., compressed). Release of the releasable attachment 1707 may then apply a force driving the distal tractor region around the distal end of the catheter, helping pull the clot into the apparatus, and reducing the force necessary to invert the distal tractor region.

As mentioned above, the material forming the distal tractor region may, and in particular the distal-most flexible and/or expandable first end region may be formed of any appropriate material. For example, the material may comprise a fabric, a weave, a knit, a braided, a sewn, a tube, and/or a flat sheet. The material may have any appropriate thickness, e.g., between 0.0005 to 0.015" wall thickness, and may have pores of any appropriate spacing/dimension (porosity) from low to high porosity. All or a portion of the distal tractor region may be radiopaque or radio transparent. In woven, knitted, braided or sewn variations, the material may be formed of multi- or mono-filaments. Different size filaments can be mixed together (e.g., big and/or small) to change gripping effect by increasing or decreasing fabric surface texture. In some variations the material (including the filaments forming the material) may be polymer based (e.g., PET, Nylon, Polypropylene, PTFE, ePTFE), elastic and non-elastic (e.g., PU, Silicone, rubber, Lycra), metal filaments (e.g., Niti, drawn filled Niti including DFT, i.e., Niti with Pt inner core, steel, stainless steel, cobalt chrome, etc.), and mix of metallic and polymer filaments. The ends of the fabric can be laser cut/welded or free cut. In some variations all or part of the distal tractor region includes a film or sheet. The film may be between 0.0005 to 0.008" thick. The film may be formed by tube extrusion or sheet and rolled into a tube. In some variations the film is yarn reinforced. The film may be slotted (e.g., may include holes and/or slits cut to improve gripping or sliding into the catheter. In some variations the film has a textured surface (e.g., textured inner surface that is exposed when inverted). The film may form a tube having ridges and/or rings (radial rings) and/or lines down the length, and/or a saw tooth pattern. A textured inner surface my include a mix of big and small filaments, and/or may be formed of more porous, less dense fabrics.

In some variation, the visibility of the grabber element is desirable but not required throughout. For example, as mentioned above markers may be located on the device. In some variations it may be desirable to see the entire structure or proximal and distal end of structure. For example, the material could be Nitinol or Nitinol drawn over platinum material (DFT) to enhance visibility.

Any of the variations may include a rotational auger element in the inside of any of the braid constructs to assist in pulling the clot back to the hub. As mentioned, any of these apparatuses may include a vacuum source. The addition of the vacuum to the system may aid the ability of the distal tractor region to pull clot/emboli into the catheter. The vacuum applied may be stead/constant, ramped or pulsatile.

In some variations the apparatus and methods for using them may include a flow stopping proximal balloon (e.g., to be positioned proximal to clot), that may reduce pressure on clot during the procedure.

The apparatuses and methods described herein may be used to capture biopsy samples (e.g., from breast or any other organs). For example, these apparatuses can be used to remove bigger tissue segments (e.g., cancer, gallbladders, etc.) when a laproscopic procedure is performed.

When the material forming the distal tractor region is a woven/braided material, the resulting mesh structure may have a braid length ranging from 1 to 100 cm long to around the outer diameter (O.D.) of the catheter, with a preferred length of between about 3-30 cm.

In any of these variations, the tractor tube and/or catheter (including the distal tractor region) may be constructed so the distal tractor region may be pulled so that the distal tractor region is drawn (inverted) around the outer diameter of the catheter distal end with a minimal force so the catheter tip does not buckle or significant deform (e.g., snake) in the blood vessel, wherein the pull forces are less than about: 50 grams, 100 grams, 300 grams, 500 grams, 800 gram, 1000 grams, 2 kg, 3 kg, 5 kg, 8 kg, 10 kg, 15 kg, 20 kg, etc.

In variations in which the grabber (distal tractor region) is constructed as a woven (e.g., braided) structure at least on a distal end (e.g., the expandable and/or flexible first end region), examples of the filaments forming the woven structure may include: NiTi, NiTi-PT DFT wire (NiTi tube over Pt inner), PET, PP, Nylon, Algiloy, SS, hybrid materials. When used, NiTi may be etched to make is very smooth. The number of filament ends may be about: 16, 24, 36, 48, 77, 96, 144 or any number between these integers. Any braid construction may be used. For example, an exemplary braid construction may include 1 over 1 (1×1), 1×2, 2×2, etc. In some variations the filaments forming the woven and/or knitted material comprises a monofilament, e.g., having an outer diameter (O.D.) size of about: 0.0005", 0.00075", 0.001", 0.0015", 0.002", 0.003" or an combination of sizes or diameter size which is between the integers list herein. As mentioned, these apparatuses may be adapted for neuro vasculature used, e.g., assuming 2-3 mm vessel inner diameter (ID). For example, an apparatus appropriate for neurovascular applications as described herein may include between 36 to 72 ends of a 0.001" to 0.002" polymer braid annealed to 3-7 mm OD. In some variations, the distal tractor region includes 24 braided wires having an OD of 0.0005" by 0.0015" or 0.002" of flat Niti wire, annealed on a 2 mm mandrel, braided at a 45 degree angle. Alternatively in one variation the distal tractor region comprises a braided material formed from 24 wires of a 0.002" thickness Niti wire, annealed on a 2 mm mandrel, braided at a 45 degree angle. In one example, the distal tractor region comprises a braided material including 24 wires 0.002" DFT Niti wire, annealed on a 2 mm mandrel, braided at a 45 degree angle. In one example, the distal tractor region comprises a braided material including 8 ends of 0.003" wire mixed with 8 additional ends of 0.002" Niti wire on a 2 mm mandrel. In one example, the distal tractor region comprises a braided material including 16 ends of 0.002" platinum iridium wire, annealed on a 2 mm mandrel. In one example, the distal tractor region comprises a braided material including 24 ends of PP monofilament, having an outer diameter of 0.002" diameter. In one example, the distal tractor region comprises a braided material including 12 ends of 0.003" PP monofilament. In one example, the distal tractor region comprises a braided material including 16 ends of 0.003" PP mono. In one example, the distal tractor region comprises a braided material including 72 ends, 0.001" PET or PP, 8 mm mandrel, 90 degree braid angle, 1×1. In one example, the distal tractor region comprises a braided material including 36 ends, 0.001" PET or PP, 6 mm mandrel, 75 deg braid angle, 1×1. In one example, the distal tractor region comprises a braided material including 48 ends, 0.002" PET or PP, 8 mm mandrel, 90 degree braid angle, 1×1. In one example, the distal tractor region comprises a braided material including 24 ends, 0.002" PET or PP, 6 mm mandrel, 70 degree braid angle, 1×1.

In variations in which the distal tractor region comprises a mesh, the tubular mesh may be formed from a knit or alternative structure that is constructed so it's radially compression (change in tubular mesh inner diameter, ID) experiences a 5-20% reduction in diameter when the mesh tractor is pulled axially and around the outside of the catheter tip and into the catheter ID. This 5-20% mesh diameter reduction, may aid in grabbing the clot or foreign object when pulling the mesh into the catheter, without generating so much radially compression force that the tubular mesh binds on the catheter tip when pulled and does not easily roll around the catheter tip. In contrast a woven mesh may collapse between 20-60% within the catheter when drawn proximally, which may provide a substantial amount of compression of a clot of other removed material.

In variations in which the apparatus is configured for use in the peripheral vessels (e.g., having between a 4 to 8 mm vessel ID), the distal tractor region may be configured for this application. For example, the distal tractor region may include a braided material having 24 ends of PP, 0.009" PP monofilament formed on a 4 mm mandrel and annealed. The distal tractor region may include a braided material having 48 ends of PP 0.008" mono, 4 mm mandrel annealed. The distal tractor region may include a braided material having 72 ends 0.006" PP mono 4 mm mandrel annealed. The distal tractor region may include a braided material having 36 ends of 0.004" Niti, 4 mm mandrel annealed. The distal tractor region may include a braided material having 48 ends of 0.004" DFT Niti mandrel annealed.

In variations in which the apparatus is configured as a biopsy device (e.g., having a 4-12 mm sample size), the apparatus may be a woven material including 72 ends of PP 0.007" mono formed on a 10 mm mandrel. In some variations, the apparatus (e.g., the distal tractor region) may include 48 ends of 0.004" Niti formed on a 1 mm mandrel. In some variations, the apparatus (e.g., the distal tractor region) may include 48 ends of PP 0.008" mono on a 12 mm mandrel.

In any of the variations described herein the apparatus may be configured to have a relatively low friction. In particular the distal tractor region may have a low friction to allow it to be more easily and/or reliably pulled through the catheter when retracting a clot. As already mentioned above, any of these variations may include a lubricous material and/or coating including using or coating one or more of the following materials on the grabber (distal tractor region): PET, PP, PTFE, ePTFE. When the material forming the apparatus is a small diameter filament metallic structures, the filaments may be between 0.0005 to 0.003" in diameter. The material may be Niti, Stainless, MP35n, Ti, Platinum, Platinum Iridum, cobalt chromium alloy etc.

In variations in which the distal tractor region is a mesh (e.g., woven and/or kitted material), the diameter of the distal tractor region relative to the catheter diameter may be depended on the woven/knitted structure. For example, when braided, the ratio may be between 2 to 1 or greater; when warp knit, the ratio is between: 1.5 to 1 or greater. When formed as a lasered tube, the ratio is between 1.1 to 1 or greater. Similarly for braided tube or tape structures, the braid angle inside of the catheter should be between 0 to 45 degrees of the braid angle inside catheter, and between about 20 to 90 degrees of the braid angle outside catheter. In variations in which the distal tractor region includes a knit braid (e.g., a warp knit) tube, the apparatus may include 12 to 16 ends per inch. For an apparatus having a 0.0035" ID catheter: 12 to 16 ends of 20-40D PET multifilament may be used, or 12 to 16 ends of 0.0007 to 0.003" PET or Polypro or PTFE monofilament, or 12 to 16 ends of 0.0007 to 0.002" NITI, stainless, MP35n, etc.

As mentioned above, in some variations the distal tractor region is formed of ePTFE as a sheet (e.g., formed into a tube or tape). This material may be thin walled (e.g., between 0.0005 to 0.003" thick), think walled (between 0.0005 to 0.002"), and may fold/role over catheter tip. The material may include a 0.001 to 0.004" with lasered pattern that is stent-like.

Other examples of designs for apparatuses including distal tractor region of different shapes may be a function of catheter ID. For example, in some variations the apparatus may select the catheter ID, number of filaments, diameter/length of filaments, stiffness of bending/rolling stiffness, Poisson's ratio, friction (and/or texture) of the inner surface of the grabber, etc. Smaller diameter catheters may require less mesh filaments or smaller ePTFE tube IDS's than larger diameter catheters. For example, in some variations in which the distal tractor region is braided, the apparatus may include a 0.072" ID catheter having a distal tractor region with 24 to 72 ends of 0.0008" to 0.002 Niti wire, braided on a 6 mm mandrel at a 90 degrees braid angle. In some variations the distal tractor region is formed of 24 to 72 ends of 0.0008" to 0.002 PP monofil, braided on a 6 mm mandrel at a 90 degrees braid angle. In some variations the distal tractor region is formed of a knit braid (assume 0.072" catheter) and may include 16 ends or 40D PET multifil free warp-knitted, annealed on a 3 mm mandrel. In some variations the distal tractor region is formed of 16 ends of 0.002" PP monofil warp-knitted, annealed on a 3 mm mandrel. In variations having a distal tractor region formed of ePTFe tubes (again, assuming a 0.072" catheter), the distal tractor region may be 0.002" thick, 3 mm tube. Alternatively, the distal tractor region may be a 0.002" thick, 3 mm tube laser slotted to collapse and grab clot.

As mentioned, in some variations the apparatus is configured to include a gripping inner mesh surface in the distal tractor region. For example the apparatus may include a laser slotted ePTFE tube having larger diameter braid filaments and/or mixed diameter filaments. In some variations a gripping inner mesh surface may be formed with a knit braid that is a warp knit formed tube. Such a structure may have a natural macro structure to allow mesh rolling and gripping of clot, since filaments do not enter catheter ID parallel to catheter, but rather they are perpendicular or looped relative to catheter long axis. For examples in which the distal tractor region is formed of an ePTFE laser slotted (sheet of) material, the structure may include slots cut to allow Poisson ratio to effect tube diameter while creating grippy texture to grab clot.

Figure 18A:
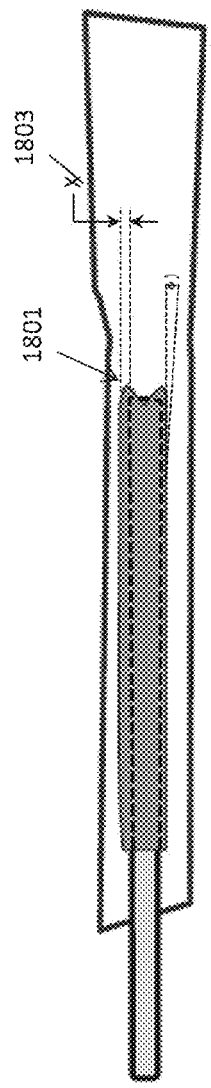
FIGS. 18A-18C illustrate examples of expandable first end regions having different stiffnesses.
Figure 18B:
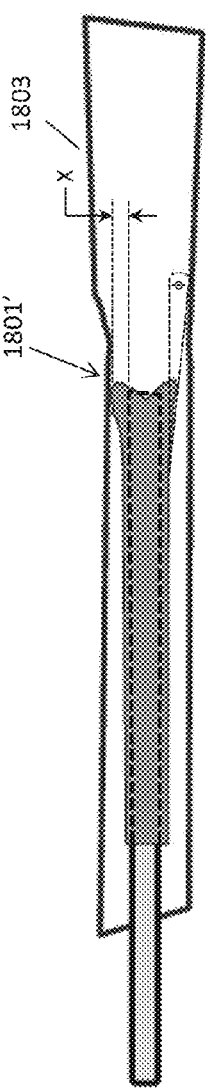
Figure 18C:
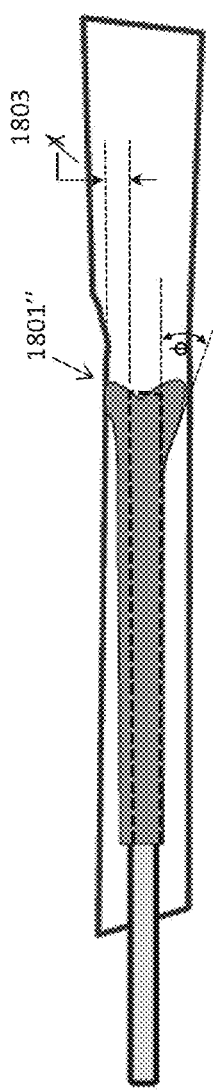

In general, the effectiveness of the distal tractor region in grabbing a clot may be enhanced by using self-expanding and/or stiffer distal tractor region (e.g., self-expanding and/or flexible first end regions of the distal tractor region). When the first end region of the distal tractor region is formed of a braid, stiffer filaments (e.g., formed of bigger diameter filaments, stiffer materials, larger number of fibers, etc.) may result in more expanded first end regions of the distal tractor region, as illustrated in FIGS. 18A-18C. In FIG. 18A a softer distal tractor region does not expand out beyond the OD of the catheter any substantial distance. FIG. 18B shows a slightly stiffer/more expandable first end region of the distal tractor region. FIG. 18C shows the most expandable distal tractor region 1801, which may optimally expand to the intima of the vessel 1803.

As shown in FIGS. 18A-18C, the mouth of lip of the expandable tractor region may form a tangent angle or roll angle ($\Phi$) with respect to the long axis of the catheter OD. This angle may be in the range of approximately 5° to 60° degrees (e.g., 10°-60°, 10°-50°, 10°-45°, 10°-40°, etc., and preferable at least 10 degrees). The inventors have surprisingly found that, in some variations, having a roll angle of at least about 10 degrees (e.g., 10°-60°, 10°-50°, 10°-45°, 10°-40°) with the tube as the tractor region is retracted into the catheter may prevent binding or jamming on the catheter tip. The mesh tube may be modified (e.g., at the distal tip or end region), including by modifying the stiffness and/or shape of the distal tip, to ensure the roll angle in greater than 10 degrees. Alternatively or in combination to maintaining a minimum roll angle it may be desirable to maintain a physical space or gap between the tube material ID and the O.D of the catheter (see, e.g., FIGS. 18A-18C) at the catheters most distal tip. The gap may need to be greater than 0.1 mm, 0.2 mm, 0.3 mm, 0.4 mm, 0.5 mm, 0.7 mm, 0.8 mm, or 1.0 mm to ensure the tube rolls around the distal end of the catheter when the tube is retracted.

In any of these variations, the distal tractor region may be lubricious (e.g., hydrophilic coating, silicone coating, thin urethane or other thin elastomeric coating) as mentioned above. One or more polymeric braid ends may be included to enhance lubricity (e.g., polypropylene, nylon, etc.). Further, the braid angle may be kept small (e.g., less than 70 degrees, 50 degrees, 45 degrees, etc.) to allow better pulling. This angle may be measured when the distal tractor region is rolling around/over the tip of the catheter. Increasing the number of ends of the weave may also prevent locking of the first end region within the catheter, so that gaps/spaces between the braid elements are smaller and less likely to snag on the catheter tip when rolling the distal tractor region over the end of the catheter. Any of these apparatuses may also include an axial element when formed as a braided element that is less likely to collapse or reduce in diameter when pulled, and therefore less likely to hang up on the catheter opening when rolling over the tip. It may also be advantageous to use slightly larger braid filaments when using Niti (e.g., >0.0001" diameter); the greater the diameter, the less likely the braid may deform to lock onto the catheter tip. As mentioned above, in some variations the distal tractor region may be heat set to automatically roll over the distal end of the catheter when advanced distally.

Figure 19A:
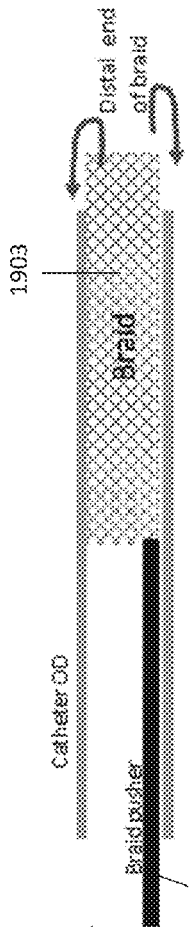
Figure 19B:
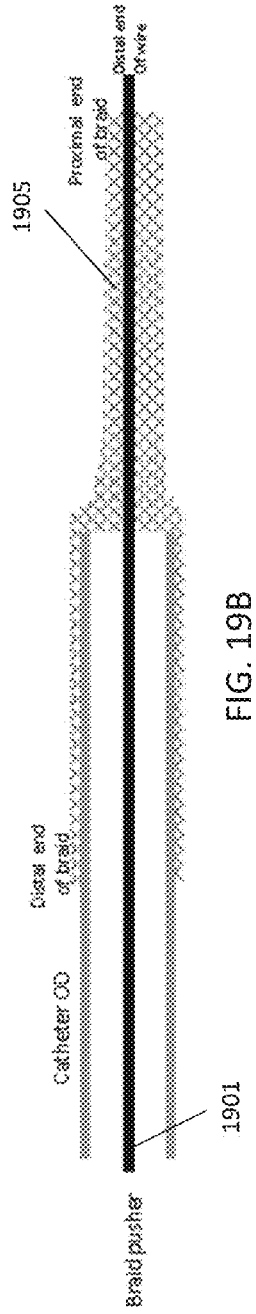

FIGS. 19A and 19B illustrate alternative methods for forming the doubled-back configuration of the distal tractor region. In FIG. 19A, the tubular distal tractor region 1903 may be coupled to a puller/pusher 1901 and then inverted over the catheter tip as mentioned above. In FIG. 19B, the tubular braid 1905 is attached distally through the braid to a wire/puller 1901 and pulled to invert it over the distal end of the catheter.

Figure 20A:
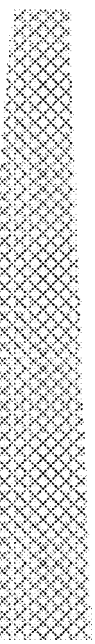
FIGS. 20A and 20B illustrate exemplary profiles of expandable first end regions that may be used as part of a distal tractor region of an apparatus as described herein.
Figure 20B:
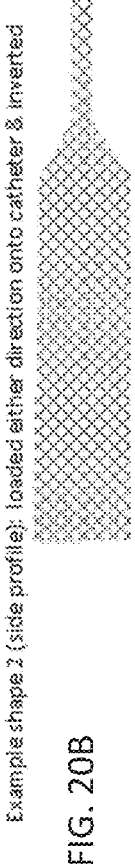

In general, the first end region of the distal tractor region may have any appropriate shape (refer to FIGS. 15A-15D). FIGS. 20A and 20B illustrate examples of tapered woven braids that may form the distal tractor region. In. FIG. 20A, the braid has a tapered side profile that may be attached to a puller (proximal end of the flexible tractor tube) and inverted. Any of the braids described herein may include a marker wire (e.g., DFT, gold, Pt, Pt iridium, etc.) to help with visualization (e.g., fluoroscopically). In FIG. 20B, the mesh is tapered more abruptly than in FIG. 20A.

As described above, in general, any of the catheters described herein may be adapted for use with these apparatuses. For example an appropriate catheter may be highly flexible with a good column stiffness (e.g., will not shorten in length when advanced distally). The catheter can have a high angle braid reinforcing element. For example, the catheter may have a high angle braid through proximal to distal end (70-85 degrees, small wire Niti, Stainless, cobalt chrome, MP35N, flat or round wire), and a lower braid angle for the distal 1 to 5 cm of the catheter. This will allow the id of the catheter to expand when axial compression is applied, and/or under an internal expanding force (e.g., clot).

In general, any of these catheters may include a changing stiffness/compliance. For example, the proximal third (⅓) may be stiffer; the middle section may be less stiff, and the distal 20% (⅕) may be the least stiff. Further, the distal tip of the catheter may have an appropriate radius (curve) as described in FIGS. 1A and 1B. In general, the radius should be smooth and round, and not square. In addition, the distal tip of the catheter may be made of a hard enough material (~72D or harder) to allow braid to roll and not grab onto tip. For example, the catheter tip may have a hard metallic structure to reduce friction (e.g., stainless steel, Pt, etc.). The less the catheter tip compresses/buckles when pulling the distal tractor region, the better. In some variations the catheter includes an additional reinforcement such as a braid reinforcement rather than a coil reinforcement, to prevent braid buckling for the last 5-10 cm of the catheter. Thus, as described herein, in some variations, the tip of the catheter may be made of a lubricous and/or hard material to help reduce the braid to catheter tip friction when the braid is pulled or pushed around the catheter tip. Lubricous materials may include flour-polymers like PTFE, FEP and/or hydrophilic coatings. Hard materials like Nylons, or metallics like stainless steel, Platinum and PT iridium alloys could be used at the tip and fused/attached to softer materials proximally. If a hard tip is put on the distal end of the catheter tip it may be short in length (e.g., <5 mm and preferably <3 mm) so it does not adversely affect catheter tracking.

Figure 21A:
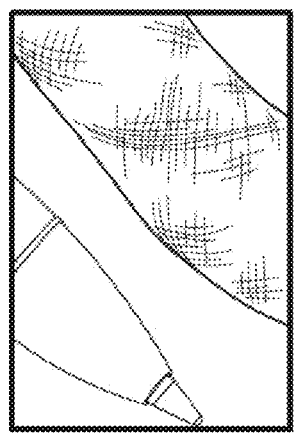
FIGS. 21A-21D show examples of apparatuses used to remove clots.
Figure 21B:
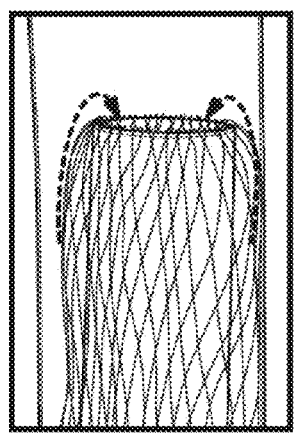
Figure 21C:
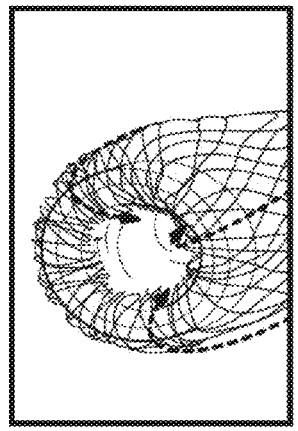
Figure 21D:
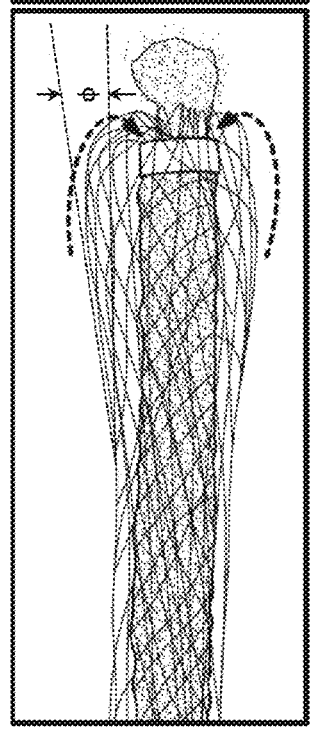

FIGS. 21A-21D show examples of apparatuses used to remove clots. In this example, the distal tractor region was formed of a fine Denier PET mesh of approximately 72 ends that is 10 mm (expanded) diameter pulled down onto a 0.071" catheter, as shown in FIGS. 21A and 21B. FIG. 21A shows an example of an expandable first end region prior to coupling to a catheter. FIG. 21B illustrates the expandable first end region within a vessel (glass tube) being drawn into a catheter by pulling the proximal end of the flexible (tractor) tube. FIG. 21C shows the distal end region of the apparatus including the expandable first end regions doubled over the distal end region of the catheter. FIG. 21D illustrates the apparatus of FIG. 21C drawing a clot into the catheter.

Figure 22:
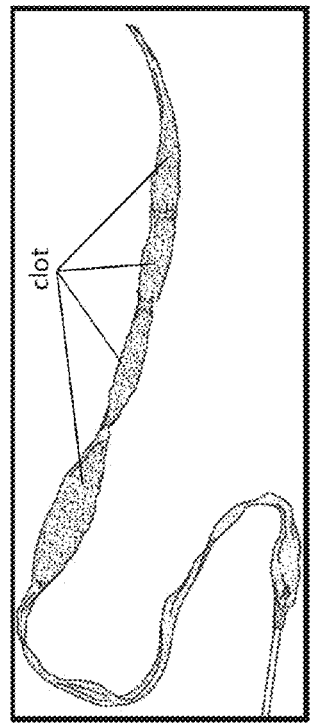
FIG. 22 shows the expandable first end region of FIG. 21D with the captured clot after drawing it proximally out of the catheter.

Another example examined a distal tractor region formed from a 6 mm braid having 72 ends and 0.001" diameter filaments rolling into and doubled over a 0.071" ID catheter. A 'medium hard' 5 mm clot that was 20 cm long was successfully removed. FIG. 22 shows the expandable first end region of FIG. 21D with the captured clot after drawing it proximally out of the catheter.

FIGS. 23A-23D illustrate a mechanical thrombectomy apparatus as described herein capturing a blood clot and drawing it into the apparatus. FIG. 23E illustrates the clot held within the flexible tractor tube after the flexible tractor tube has been removed from the catheter (e.g., proximally).

Figure 24:
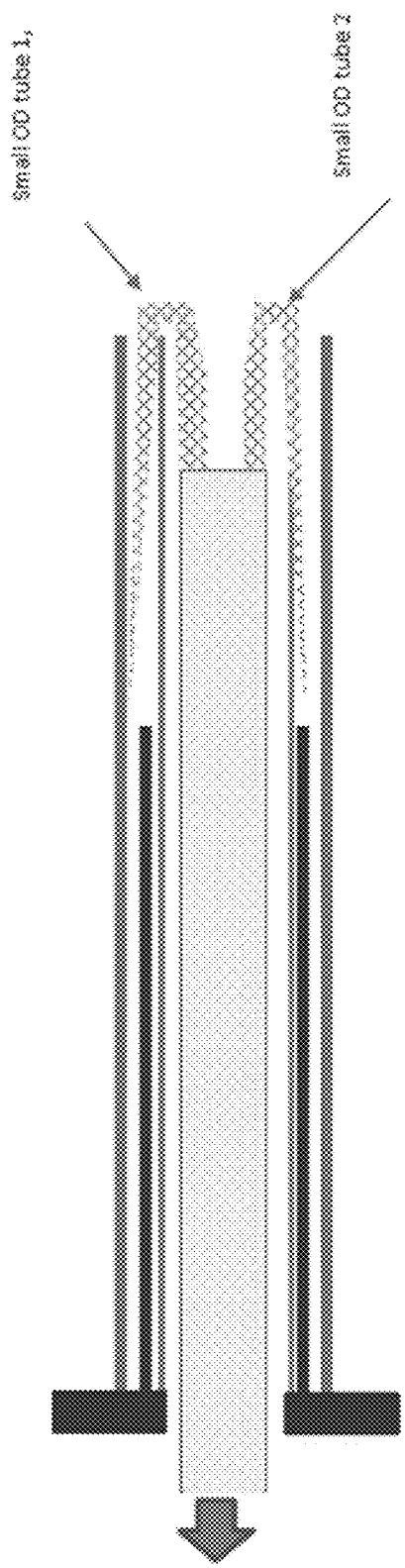
FIG. 24 is another example of an apparatus including a flexible tractor member in which the distal tractor region is formed of a plurality of filaments that are arranged as strips of material (longitudinally parallel) that are not woven or braided. These strips may be filaments, or tubes, etc.

In some variations described herein the distal tractor region is not formed of a woven or knitted material, but is instead composed of strip or bundles of longitudinally arranged (e.g., in parallel or near-parallel arrangement). For example, FIG. 24 is another example of an apparatus including a flexible tractor member in which the distal tractor region is formed of a plurality of filaments that are arranged as strips of material (longitudinally parallel) that are not woven or braided. These strips may be filaments, or tubes, etc.

FIGS. 25A-25F illustrate another variation of a distal tractor region of a flexible tractor assembly in which the expandable first end region (e.g., the distal end region of the distal tractor region) is formed of a plurality of filaments or strips, similar to that shown in FIG. 24; the distal end of the catheter includes channels, as shown in FIGS. 25A-24B; the strips may fit within these channels, as shown in FIGS. 25C-25D. FIGS. 25E and 25F show sectional views through FIGS. 25C and 25D. FIGS. 25A, 25C and 25E show side views and FIGS. 25B, 25D and 25F show axial views. In this example, the catheter tip includes channels 2502 into which the filaments/strips 2503 run. The strips forming the distal tractor region are attached to the more proximate puller region of the flexible tractor tube 2505, shown in FIG. 25E.

FIGS. 26A and 26B show a variation of the apparatus of FIGS. 25A-25F with an outer sleeve (e.g., an outer catheter or release protector catheter or other outer sleeve/protector)

FIGS. 27A-27B show a sectional view through the apparatus of FIGS. 26A-26B.

Figure 28:
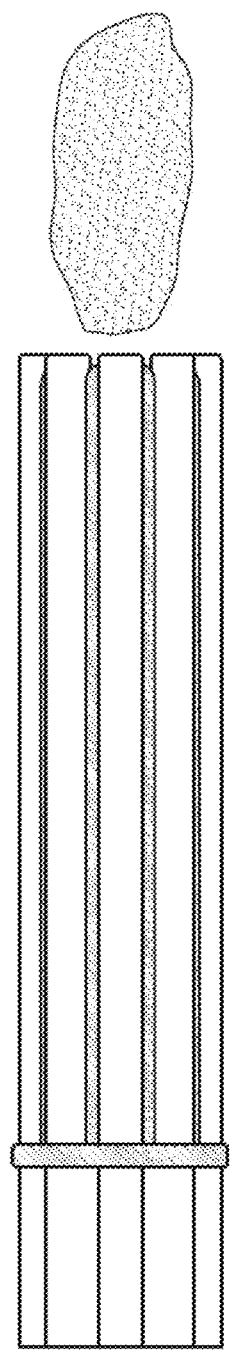
FIG. 28 is an apparatus including a distal tractor region of a flexible tractor assembly having a plurality of longitudinally-parallel (non-woven/braided) filaments or strips in which the distal ends of the filaments or strips are connected to each other by a distal connector.

FIG. 28 is an apparatus including a distal tractor region of a flexible tractor assembly having a plurality of longitudinally-parallel (non-woven/braided) filaments or strips in which the distal ends of the filaments or strips are connected to each other by a distal connector.

Figure 29:
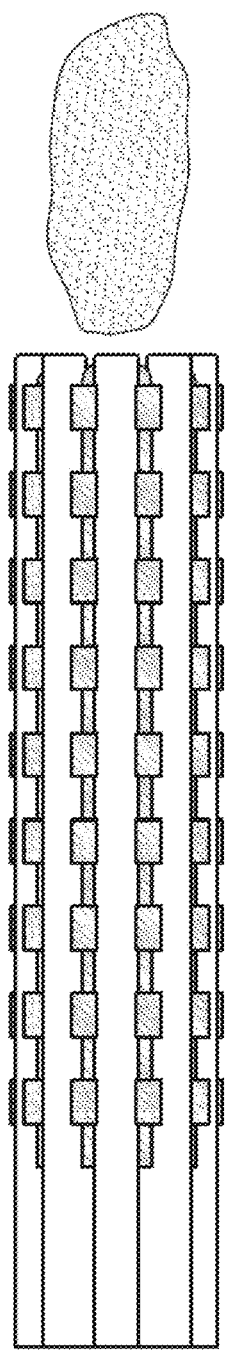
FIG. 29 shows a distal tractor region of a flexible tractor assembly in an apparatus in which the longitudinally-parallel (non-woven/braided) filaments or strips include grabbing elements.

FIG. 29 shows a distal tractor region of a flexible tractor assembly in an apparatus in which the longitudinally-parallel (non-woven/braided) filaments or strips include grabbing elements.

Figure 30A:
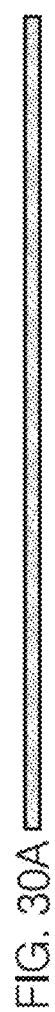
FIGS. 30A-30C illustrate example of filaments/strips with grabbing elements. Grabbing elements (and/or filaments including them) may be used as part of any of the variations described herein, including woven or braided distal tractor regions.
Figure 30B:
Figure 30C:

FIGS. 30A-30C illustrate example of filaments/strips with grabbing elements. Grabbing elements (and/or filaments including them) may be used as part of any of the variations described herein, including woven or braided distal tractor regions. Other options for filaments/strips with grabbing elements may include braided strips, mesh/woven strips, and micro-coils.

Figure 31:
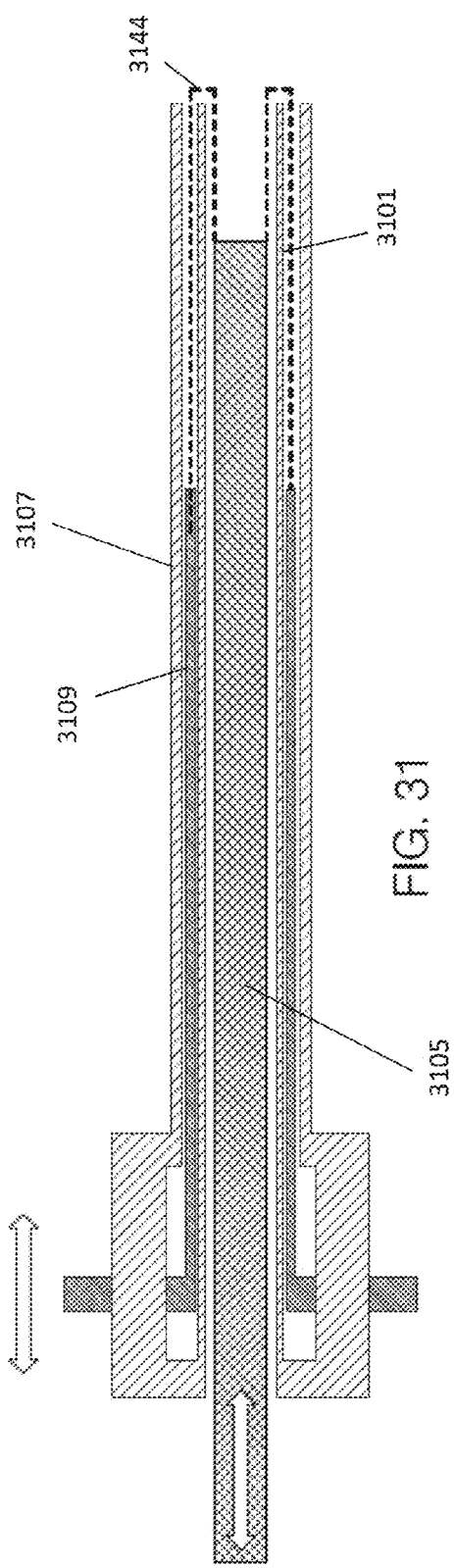
FIG. 31 illustrates a variation in which the distal tractor region is adapted to be reciprocated (e.g., pushed and pulled) so that the expandable first end region may be draw into and reversed out of the catheter.

In any of these configuration described herein, the apparatus may be adapted to allow reciprocation of the distal tractor region, cycling from outside to inside and back outside of the distal end of the catheter. For example, FIG. 31 illustrates a variation in which the distal tractor region is adapted to be reciprocated (e.g., pushed and pulled) so that the expandable first end region may be draw into and reversed out of the catheter. In this example, the tractor tube (puller) 3105 is attached to the distal tractor region 3144 that may be attached (and in some variations is not attached) to a second catheter 3109 over the inner catheter 3101. The mid-catheter 3109 can be coupled to the puller 3105 and the two reciprocated together so that the braid reciprocated back and forth inside of the catheter 3101. This may help break up a clot, which may be particularly when used with suction.

FIG. 32 illustrates another example of an apparatus as described herein in which the distal-most end 3205 of the flexible first end region of the distal tractor region is non-releasably fixed to the distal end of the outside of the catheter 3201; the rest of the expandable first end region 3209 is sufficiently elastic/flexible to be drawn into the catheter (pulling a clot 3255 with it). The flexible tractor assembly may then be left retracted and the entire apparatus withdrawn. This example may include an optional vacuum 3260.

FIG. 33 is another example of an apparatus in which the puller portion 3305 of the flexible tractor assembly is formed of the same material as the distal tractor region 3344 but may be laminated or otherwise reinforced to have less flexibility/stretchability than the distal tractor region.

Figure 35A:
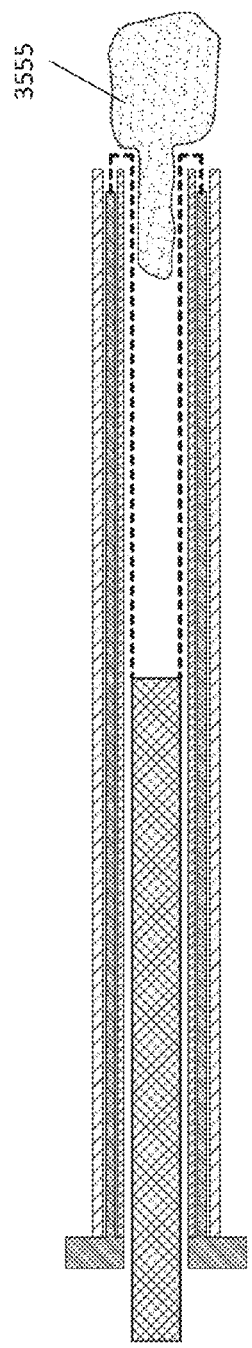
FIGS. 35A-35C illustrate operation of an apparatus as shown in FIG. 34 in which the clot is drawn into the catheter by withdrawing the expandable first end region of the distal tractor region into the catheter (e.g., pulling on the puller region of the tractor assembly) which compresses the clot (FIGS. 35A-35B); releasing the tractor assembly and/or pushing it distally may further break up the clot and release it from the distal tractor region so that it may be suctioned up proximally with a manual or powered vacuum source (FIG. 35C).
Figure 35B:
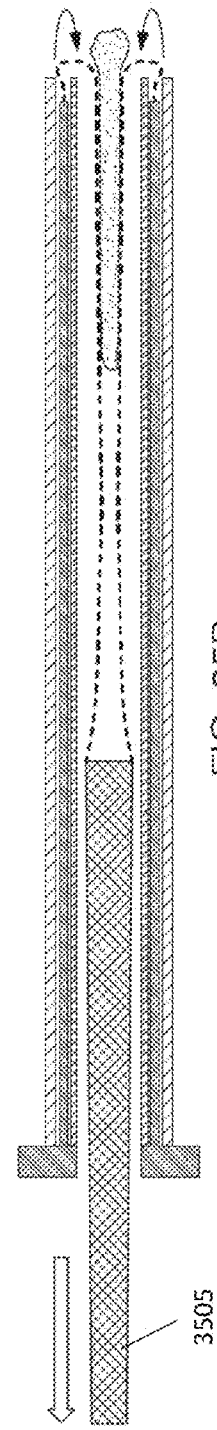
Figure 35C:
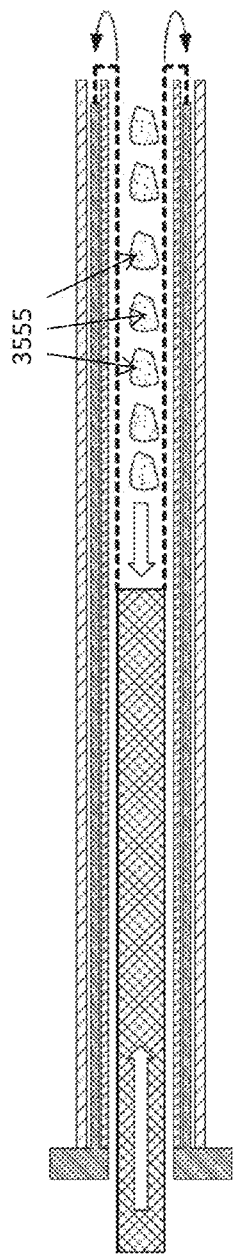

FIG. 34 illustrates another example in which the distal tractor region 3444 is adapted to compress the clot 3455 when draw into the catheter 3401. FIGS. 35A-35C illustrate operation of an apparatus as shown in FIG. 34 in which the clot 3455 is drawn into the catheter by withdrawing the expandable first end region of the distal tractor region into the catheter (e.g., pulling on the puller region 3505 of the tractor assembly) which compresses the clot (FIGS. 35A-35B); releasing the tractor assembly and/or pushing it distally may further break up the clot and release it from the distal tractor region so that it may be sectioned up proximally (FIG. 35C).

Figure 36:
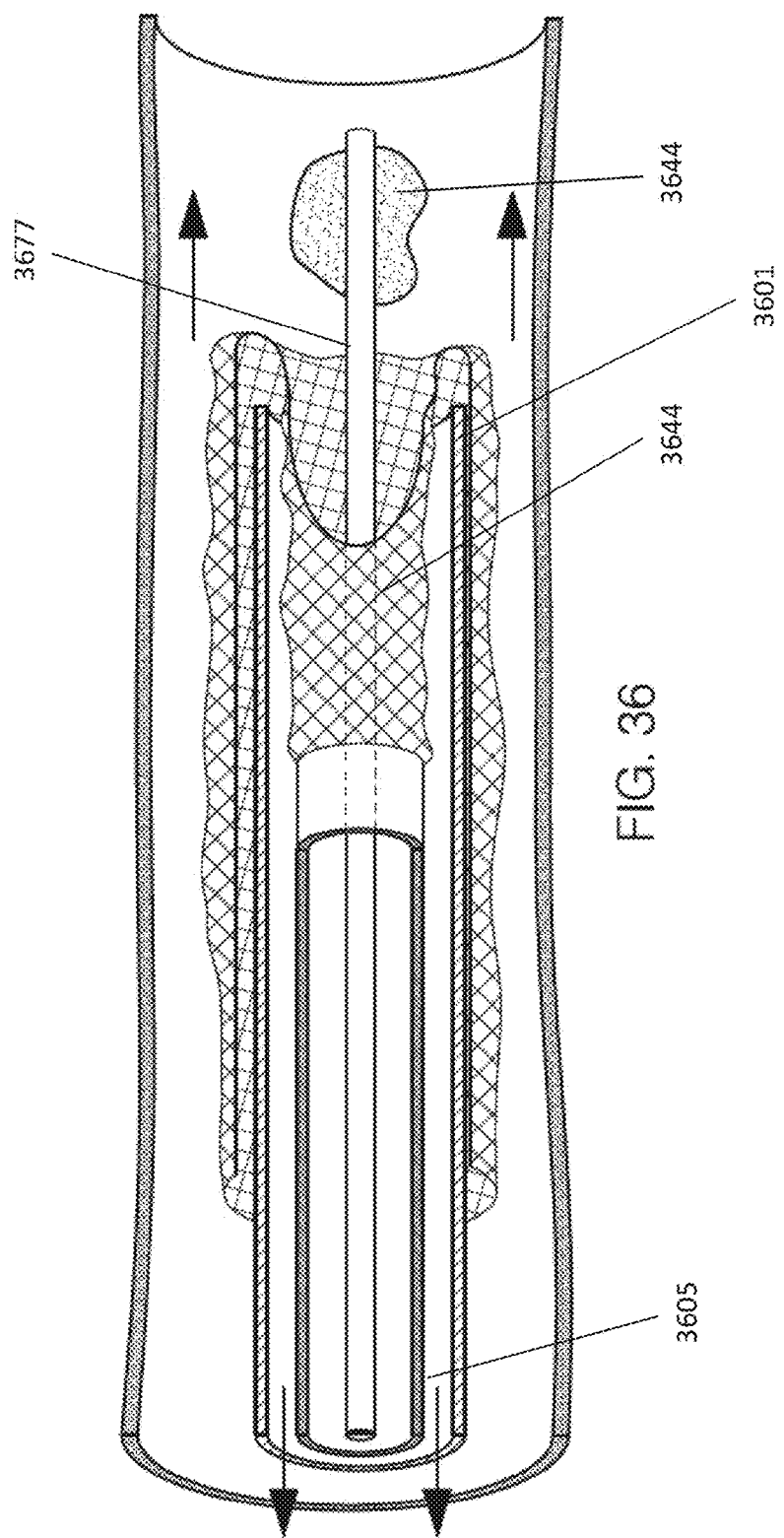
FIG. 36 illustrates an example of an apparatus and method of use in which drawing the flexible tractor assembly proximally may advance the apparatus distally through the body (e.g., vessel) over a guidewire, which may be treated to engage the distal tractor region.

FIG. 36 illustrates an example of an apparatus and method of use in which drawing the flexible tractor assembly proximally may advance the apparatus distally through the body (e.g., vessel) over a guidewire, which may be treated to engage the distal tractor region. In this example, the apparatus may be configured to pull the inner tractor tube (catheter 3605) which has the mesh forming the distal tractor region 3644 attached to its distal end and inverting over the distal end of the catheter 3601. Pulling the flexible tractor tube 3605 makes the braid roll over the opening of the catheter 3601. The mesh/braid forming the distal tractor region (e.g., the first end region of the distal tractor region) is constructed to collapse in diameter when tensile loads are applied to this structure and lock/grab onto inner wire (guidewire 3677). This inner guidewire may have a tacky, rough or knobby surface aid mesh/braid grabbing onto wire. As the mesh/braid grabs onto the guidewire, the tractor tube, as a reactionary force, will be driven forward in the vessel. Alternatively the user will be able to easily advance outer catheter 3601 forward through vessel while pulling back on the tractor tube.

Figure 37A:
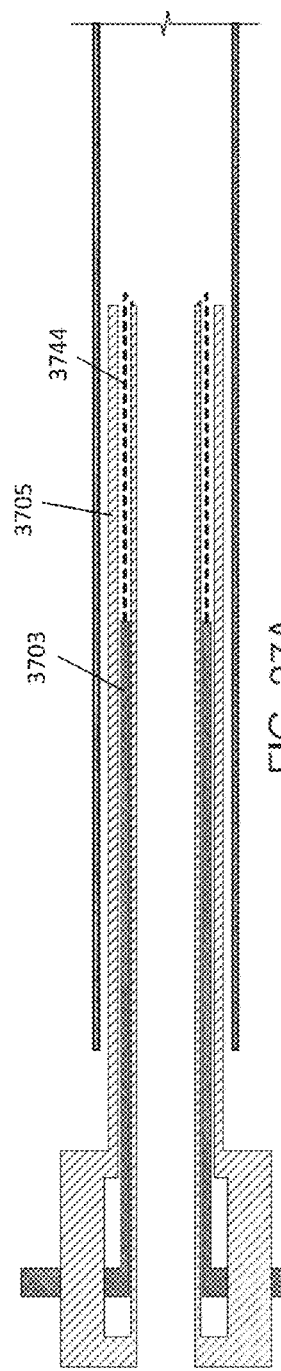
FIGS. 37A-37C illustrate an apparatus and method of use in which drawing the flexible tractor assembly proximally may advance the apparatus distally.
Figure 37B:
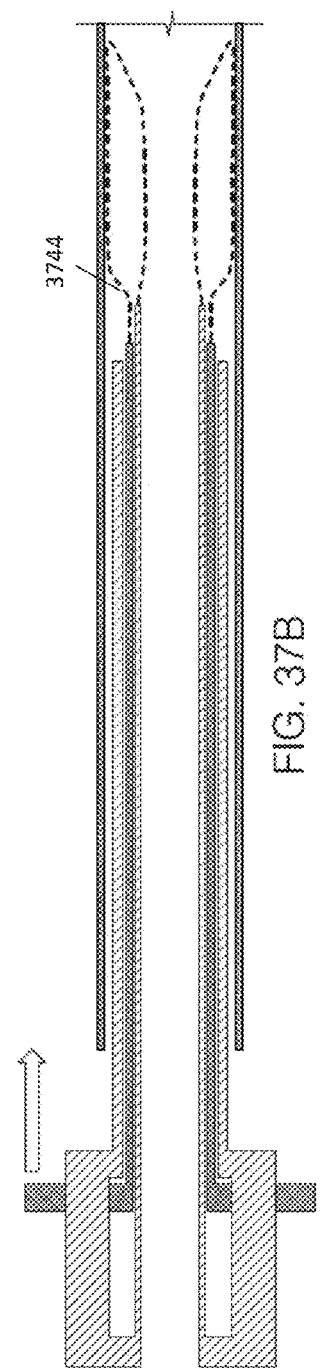
Figure 37C:
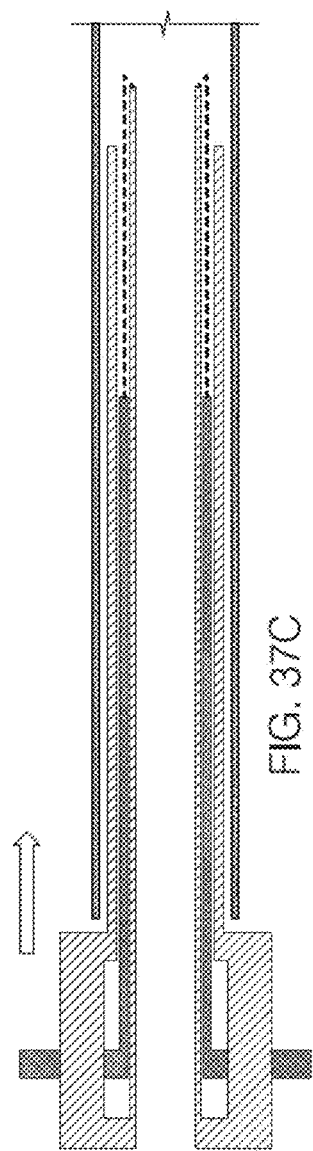

FIGS. 37A-37C illustrate another apparatus and method of use in which drawing the flexible tractor assembly proximally may advance the apparatus distally. In FIG. 37A, the distal tractor region 3744 is attached to a middle catheter 3703 (an optional outer catheter 3705 may be included) and the opposite end of the distal tractor region 3744 is bonded to the distal end of the inner catheter 3701 within the inner diameter of this catheter. In FIG. 37B the inner catheter is advanced distally, expanding the distal tractor region both laterally and forward. As shown in FIG. 37C, the outer and inner catheters may then be pushed distally to move the apparatus more distally.

In some variations the distal and flexible tractor region may be held pre-loaded outside of the catheter, e.g., in a roll or bundle, over the distal end region of the catheter, so that it can be gradually pulled out of the external storage region and rolled and inverted over the distal end of the catheter. An example of one such variation is shown in FIGS. 38A and 38B. this exemplary apparatus may be used to remove material from within a vessel as shown in FIG. 38B, and may be referred to as an "infinite" tractor mechanism because a large amount (e.g., greater than 50 cm, greater than 60 cm, greater than 70 cm, greater than 80 cm, greater than 90 cm, greater than 100 cm, greater than 150 cm, 200 cm, greater than 300 cm, greater than 400 cm, greater than 500 cm, etc.) of tractor material (e.g., mesh) may be stored in an external holding region, wound-up but dispensable over an extended use.

In FIG. 38A, the apparatus may include the catheter (inner catheter) 3811 and the distal tractor region 3806 is formed of a mesh that is rolled up 3803 in a housing region 3813 proximal to the distal end of the catheter. The clot 3805 may be drawn into the catheter by pulling the distal tractor region proximally within the catheter. Because a great deal of distal tractor region may be stored and withdrawn proximally, this variation may be useful for very long procedures or where there is a lot of material to be removed.

This variation may allow a user to unroll a long length of mesh, which may be advantageous for more rigid tools, such as, for example, a rigid hypotube during surgery, for example, removing fat in a liposuction procedure, removing clot in an intracerebral hemorrhage or a larger peripheral vascular clot.

As mentioned above, in any of the variations described herein, the distal tractor member may be a woven (e.g., knit) or braided mesh material. The mesh may be a knit material, including, for example a weft knit, circular knit, warp braid knit, and/or braid knit.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of performing a mechanical thrombectomy to remove a clot from a blood vessel, the method comprising:
    advancing a distal end of a catheter through the blood vessel towards the clot;
    exposing a distal tractor region of a tube that is within the catheter from the distal end of the catheter, wherein the distal tractor region comprises an expandable first end region and a less expandable second end region proximal to the expandable first end region;
    allowing the expandable first end region to expand within the blood vessel;
    positioning the distal end of the catheter so that a distal end region of the catheter is between the less expandable second end region and the expandable first end region of the distal tractor region while the expandable first end region is doubled over the less expandable second end region; and
    drawing the clot into the catheter by rolling the expandable first end region over the distal end of the catheter so that the expandable first end region inverts as the expandable first end region is pulled into the catheter.

2. The method of claim 1, wherein positioning comprises distally advancing the distal end of the catheter so that the distal end region of the catheter is between the less expandable second end region and the expandable first end region of the distal tractor region.

3. The method of claim 1, further comprising advancing a guidewire within the blood vessel to the clot, wherein advancing the distal end of the catheter comprises advancing the catheter over the guidewire through the blood vessel until the distal end of the catheter is proximate to the clot.

4. The method of claim 1, further comprising advancing a guidewire within the blood vessel to the clot, wherein advancing the distal end of the catheter comprises advancing the catheter over the guidewire through the blood vessel until the distal end of the catheter is proximate to the clot, further wherein drawing the clot into the catheter comprises advancing the catheter towards the clot over the guidewire while rolling the expandable first end region over the distal end of the catheter.

5. The method of claim 1, wherein drawing the clot into the catheter comprises withdrawing the tube proximally.

6. The method of claim 1, wherein drawing the clot into the catheter comprises withdrawing the tube proximally while advancing the catheter distally.

7. The method of claim 1, wherein drawing the clot into the catheter comprises withdrawing the tube proximally while advancing the catheter distally, wherein the tube is withdrawn at a different rate than the catheter is advanced.

8. The method of claim 1, wherein allowing the expandable first end region to expand within the blood vessel comprises allowing a biasing element in the expandable first end region to expand so that the distal tractor region makes contact with an intima of the blood vessel.

9. The method of claim 1, wherein exposing the distal tractor region of the tube that is within the catheter from the distal end of the catheter comprises pushing the distal tractor region out of the distal end of the catheter.

10. The method of claim 1, wherein exposing the distal tractor region of the tube that is within the catheter out of the distal end of the catheter comprises pulling the catheter proximally.

11. The method of claim 1, wherein exposing the distal tractor region of the tube that is within the catheter from the distal end of the catheter comprises pushing the distal tractor region out of the distal end of the catheter to expose the expandable first end region already inverted over the less expandable second end region.

12. The method of claim 1, wherein exposing the distal tractor region of the tube that is within the catheter from the distal end of the catheter comprises extending the expandable first end region out of the distal end of the catheter so that the expandable first end region inverts over the distal end of the catheter as the expandable first end region is extended.

13. The method of claim 1, wherein exposing the distal tractor region of the tube comprises exposing at least 5 mm of the expandable first end region and at least 5 mm of the less expandable second end region.

14. The method of claim 1, wherein exposing the distal tractor region comprises exposing at least 1 cm of the expandable first end region inverted over at least 1 cm of the less expandable second end region.

15. The method of claim 1, wherein the expandable first end region comprises one or more of: a woven material, a mesh braided material, a knitted material, or a film material with multiple openings therethrough.

16. The method of claim 1, further comprising applying a vacuum.

17. A method of performing a mechanical thrombectomy to remove a clot from a blood vessel, the method comprising:
    advancing a distal end of a catheter through the blood vessel towards the clot;
    exposing a distal tractor region of a tube that is within the catheter from the distal end of the catheter, wherein the distal tractor region comprises an expandable first end region and a less expandable second end region proximal to the expandable first end region and configured so that the expandable first end region is inverted over the less expandable second end region;
    allowing the expandable first end region to expand within the blood vessel so that the distal end region of the catheter is between the less expandable second end region and the expandable first end region of the distal tractor region; and
    drawing the clot into the catheter by advancing the catheter distally and withdrawing the tube proximally within the catheter so that the expandable first end region rolls over the distal end of the catheter and inverts as the expandable first end region is pulled into the catheter.

18. The method of claim 17, wherein the expandable first end region is inverted over the less expandable second end region before exposing the distal tractor region.

19. The method of claim 17, wherein the exposing the distal tractor region comprises inverting the expandable distal end region over the less expandable second end region as the distal tractor region is exposed.

20. The method of claim 17, further comprising, before exposing the distal tractor region, advancing a guidewire within the blood vessel to the clot and advancing the catheter over the guidewire through the blood vessel until a distal end of the catheter is proximate to the clot.

21. The method of claim 17, further comprising, before exposing the distal tractor region, advancing a guidewire within the blood vessel to the clot and advancing the catheter over the guidewire through the blood vessel until a distal end of the catheter is proximate to the clot and leaving the guidewire in place while drawing the clot into the catheter.

22. The method of claim 17, wherein exposing the distal tractor region of the tube that is within the catheter from the distal end of the catheter comprises pushing the distal tractor region out of the distal end of the catheter.

23. The method of claim 17, wherein exposing the distal tractor region of the tube that is within the catheter out of the distal end of the catheter comprises pulling the catheter proximally.

24. The method of claim 17, wherein exposing the distal tractor region of the tube comprises exposing at least 5 mm of the expandable first end region and at least 5 mm of the less expandable second end region.

25. The method of claim 17, wherein the expandable first end region of the distal tractor region comprises a mesh that is coupled adjacent to the less expandable second end region.

26. The method of claim 17, wherein the expandable first end region comprises one or more of: a woven material, a mesh braided material, or a film material with multiple openings therethrough.

27. A method of performing a mechanical thrombectomy to remove a clot from a blood vessel, the method comprising:
   advancing a distal end of a catheter through the blood vessel towards the clot;
   exposing a distal tractor region of a tube that is within the catheter out of the distal end of the catheter, wherein the distal tractor region comprises an expandable first end region and a less expandable second end region, wherein exposing comprises extending the expandable first end region out of the distal end of the catheter so that the expandable first end region inverts over the distal end of the catheter as the expandable first end region is extended;
   allowing the expandable first end region to expand within the blood vessel as it is extended out of the distal end of the catheter so that a distal end region of the catheter is between the less expandable second end region and the expandable first end region; and
   drawing the clot into the catheter by withdrawing the tube proximally within the catheter so that the expandable distal end region rolls over the distal end of the catheter, collapses, and inverts as the expandable distal end region is pulled into the catheter.

* * * * *